US011639936B2

(12) United States Patent
Loken et al.

(10) Patent No.: US 11,639,936 B2
(45) Date of Patent: May 2, 2023

(54) SYSTEM, METHOD, AND ARTICLE FOR DETECTING ABNORMAL CELLS USING MULTI-DIMENSIONAL ANALYSIS

(71) Applicant: Hematologics, Inc., Seattle, WA (US)

(72) Inventors: Michael R. Loken, Mercer Island, WA (US); Andrew P. Voigt, Seattle, WA (US)

(73) Assignee: Hematologics, Inc., Seattle, WA (US)

( * ) Notice: Subject to any disclaimer, the term of this patent is extended or adjusted under 35 U.S.C. 154(b) by 993 days.

(21) Appl. No.: 16/334,657

(22) PCT Filed: Sep. 19, 2017

(86) PCT No.: PCT/US2017/052311
§ 371 (c)(1),
(2) Date: Mar. 19, 2019

(87) PCT Pub. No.: WO2018/053528
PCT Pub. Date: Mar. 22, 2018

(65) Prior Publication Data
US 2020/0158734 A1 May 21, 2020

Related U.S. Application Data

(60) Provisional application No. 62/396,621, filed on Sep. 19, 2016.

(51) Int. Cl.
G01N 33/48       (2006.01)
G01N 33/574      (2006.01)
G16B 40/00       (2019.01)
G16B 20/00       (2019.01)
G06F 17/18       (2006.01)
G16B 40/30       (2019.01)
G16B 40/20       (2019.01)

(52) U.S. Cl.
CPC ....... G01N 33/57492 (2013.01); G06F 17/18 (2013.01); G16B 20/00 (2019.02); G16B 40/00 (2019.02); G16B 40/20 (2019.02); G16B 40/30 (2019.02); G01N 2333/70589 (2013.01); G01N 2333/70596 (2013.01)

(58) Field of Classification Search
None
See application file for complete search history.

(56) References Cited

U.S. PATENT DOCUMENTS

| 5,795,727 | A | 8/1998 | Bierre et al. | |
|---|---|---|---|---|
| 7,542,959 | B2 | 6/2009 | Barnhill et al. | |
| 8,630,833 | B2 * | 1/2014 | Loken | G06K 9/6254 703/11 |
| 9,880,155 | B2 * | 1/2018 | Loken | G01N 15/1456 |
| 2006/0263833 | A1 * | 11/2006 | Loken | G06V 20/698 702/19 |
| 2007/0112585 | A1 | 5/2007 | Breiter et al. | |
| 2009/0109432 | A1 | 4/2009 | Olson et al. | |
| 2011/0090500 | A1 | 4/2011 | Hu et al. | |
| 2014/0129152 | A1 | 5/2014 | Beer et al. | |
| 2014/0221247 | A1 | 8/2014 | Loken et al. | |
| 2016/0169786 | A1 * | 6/2016 | Albitar | G06K 9/6269 702/19 |
| 2016/0291036 | A1 | 10/2016 | O'Bryant | |
| 2017/0285035 | A1 | 10/2017 | Dittamore | |

FOREIGN PATENT DOCUMENTS

| EP | 0 559 208 B1 | 9/1993 |
|---|---|---|
| WO | 2011/148371 A1 | 12/2011 |
| WO | 2016/093048 A1 | 6/2016 |

OTHER PUBLICATIONS

Cortes, Corinna, and Vladimir Vapnik. "Support-vector networks." Machine learning 20.3 (1995): 273-297.*
Rezaeiadef, Abbas, et al. "Leukemia markers expression of peripheral blood vs. bone marrow blasts using flow cytometry." Signature 9.8 (2003): 362.*
Fiser, K. et al., "Detection and Monitoring of Normal and Leukemic Cell Populations with Hierarchical Clustering of Flow Cytometry Data", Wiley Online Library, 2011, p. 25-34.
Voigt, A. et al., "Consistent Quantitative Gene Product Expression: #1. Automated Identification of Regenerating Bone Marrow Cell Populations Using Support Vector Machines", Wiley Online Library, 2016, p. 978-986.
Voigt et al., "Consistent Quantitative Gene Product Expression: #1 Automated Identification of Regenerating Bone Marrow Cell Populations Using Support Vector Machines," *Cytometry Part A* 89A:978-986, 2016.
Civin et al., "Cell Surface Antigens on Human Marrow Cells: Dissection of Hematopoietic Development Using Monoclonal Antibodies and Multiparameter Flow Cytometry," *Concise Review International Journal of Cell Cloning*, 5:267-288, 1987.
Civin et al., "Cell Surface Antigens on Human Marrow Cells: Dissection of Hematopoietic Development Using Monoclonal Antibodies and Multiparameter Flow Cytometry," *Concise Reviews in Clinical and Experimental Hematology*, edited by Martin J. Murphy, Jr., pp. 149-159, 1992.
Coustan-Smith et al., "Clinical Importance of Minimal Residual Disease in Childhood Acute Lymphoblastic Leukemia," *Blood* 96:2691-2696, Oct. 15, 2000.

(Continued)

*Primary Examiner* — Anna Skibinsky
(74) *Attorney, Agent, or Firm* — Seed Intellectual Property Law Group LLP

(57) ABSTRACT

A normal set of cells is characterized using flow cytometry. A centroid and radius are defined for a set of clusters in an n-dimensional space corresponding to a normal maturation for a cell lineage in the normal set of cells. A test set of cells is characterized using flow cytometry and the characterization is compared to the defined set of clusters. Support Vector Machine (SVM) subroutines are employed to identify reference populations of interest by generating multidimensional boundary definitions. These boundary definitions may be used to identify reference populations to use in defining or refining a centroid line or a radius or radii defining a set of normal clusters, and to characterize and compare a test set of cells to the defined set of normal clusters.

34 Claims, 70 Drawing Sheets

(56) References Cited

OTHER PUBLICATIONS

Dash et al., "'1+1>2': Merging Distance and Density Based Clustering," *Proceedings of the IEEE 7th International Conference on Database Systems for Advanced Applications (DASFAA '01)* J Hong Kong, China, Apr. 18-21, 2001, pp. 32-39.
Daszykowski et al., "Looking for natural patterns in data Part 1. Density-based approach," *Chemometrics and Intelligent Laboratory Systems* 56:83-92, 2001.
Ester et al., A Density-Based Algorithm for Discovering Clusters in Large Spatial Databases with Noise, *Proceedings of 2nd International Conference on Knowledge Discovery and Data Mining*, 1996.
Forgy, E., "Cluster Analysis of Multivariate Data: Efficiency vs. Interpretability of Classifications," *Biometrics*, 27:768-769, 1965.
Herzenberg et al., "Monoclonal Antibodies and the FACS: Complementary Tools for Immunobiology and Medicine," *Immunology Today* 21(8):3 83-90, Aug. 2000.
Hulett et al., "Cell Sorting: Automated Separation of Mammalian Cells as a Function of Intracellular Fluorescence," *Science* 166(3906):747-749, Nov. 1969.
Hulett et al., "Development and Application of a Rapid Cell Sorter," *Clin. Chem.* 19(8):813-816, 1973.
Hurwitz et al., Asynchronous Antigen Expression in B Lineage Acute Lymphoblastic Leukemia, *Blood* 72:299-307, Jul. 1998.
International Search Report and Written Opinion, dated Nov. 24, 2017 for International Application No. PCT/US17/52311, 13 pages.
International Search Report, dated Nov. 2, 2006, for International Application No. PCT/US2006/005778, 6 pages.
Judd et al., "Large-Scale Parallel Data Clustering," *IEEE Transactions on Pattern Analysis and Machine Intelligence* 20(8):871-876, Aug. 1998.
Kachel et al., "Eight-Parameter PC-AT Based Flow Cytometric Data System," *Cytometry* 11:805-812, 1990.
LeBein et al., "Multiparameter Flow Cytometric Analysis of Human Fetal Bone Marrow B Cells," *Leukemia* 4:354-358, May 1990.
Lin et al., "A Principal Component Clustering Approach to Object-Oriented Motion Segmentation and Estimation," *Journal of VLSI Signal Processing* 17:163-187, 1997.
Loken et al., "Analysis of Cell Populations with a Fluorescence-Activated Cell Sorter," *Ann. N.Y. Acad. of Sci.* 254:163-171, 1975.
Loken et al., "Cell Discrimination by Multiangle Light Scattering," *The Journal of Histochemistry and Cytochemistry* 24(1):284-291, 1976.
Loken et al., "Characterization of Erythroid, Lymphoid and Monomyeloid Lineages in Normal Human Bone Marrow," *Flow Cytometry in Hematology*, Laerum OD, and Bjerksnes R. (eds.), Academic Press, New York, 1992, pp. 31-42.
Loken et al., "Flow Cytometric Analysis of Human Bone Marrow. I. Normal Erythroid Development," *Blood* 69(1):255-263, Jan. 1987.
Loken et al., "Flow Cytometric Analysis of Human Bone Marrow: II. Normal B Lymphocyte Development," *Blood* 70(5): 1316-1324, Nov. 1987.
Loken et al., "Normal Antigen Expression in Hematopoiesis: Basis for Interpreting Leukemia Phenotypes," *Immunophenotyping*, Carleton Stewart and Janel K. A. Nicholson (eds.), Wiley-Liss, Inc., New York, 2000, pp. 133-160.
Lucio et al., Flow Cytometric Analysis of Normal B Cell Differentiation: A Frame of Reference for the Detection of Minimal Residual Disease in Precursor-B-ALL, *Leukemia* 13:419-427, 1999.
National Institute of Health, "Protein Reviews from the Web—Index of Information Available from Prow," URL= http://mpr.nci.nih.gov/RPOW/, retrieved Feb. 6, 2008.
Nickolayev et al., "Real-Time Statistical Clustering for Event Trace Reduction," *The International Journal of Supercomputer Applications and High Performance Computing* 11(2):144-159, 1997.
Press et al. (eds.), Numerical Recipes In C: The Art of Scientific Computing, Cambridge University Press, Cambridge, NY, 1992, pp. 591-606.
Reading et al., "Expression of Unusual Immunophenotype Combinations in Acute Myelogenous Leukemia," *Blood* 81(11):3083-3090, Jun. 1993.
Robinson et al., "Current Protocols in Cytometry," John Wiley & Sons, NY, NY, Eds. 1997—current. Cover Page and Table of Contents only.
Roederer et al., "8 Color, 10-Parameter Flow Cytometry to Elucidate Complex Leukocyte Heterogeneity," *Cytometry* 29.328-339, 1997.
San Miguel et al., "Early Immunophenotypical Evaluation of Minimal Residual Disease in Acute Myeloid Leukemia Identifies Different Patient Risk Groups and may Contribute to Postinduction Treatment Stratification," *Blood* 98(6): 746-1751, Sep. 2001.
Sheikholeslami et al., "WaveCluster: A Multi-Resolution Clustering Approach for Very Large Spatial Databases," *Proceedings of the 24th VLDB Conference*, New York, USA, 1998, pp. 428-439.
Shulman et al., The Biologic Significance of Rare Peripheral Blasts after Hematopoietic Cell Transplantation is Predicted by Multidimensional Flow Cytometry, *Am. J. Clin. Path.* 112:513-523, 1999.
Sievers et al., "Immunophenotypic Evidence of Leukemia after Induction Therapy Predicts Relapse: Results from a Prospective Children's Cancer Group Study of 252 Patients with Acute Myeloid Leukemia," *Blood* 101(9): 3398-3406, May 2003.
Slater, et al., "On Locating a Facility to Service Areas within a Network," *Operations Research* 29(3):523-531, 1981.
Stockinger, H., et al., *Current Protocols in Immunology*, John Wiley & Sons, Inc., 2003, "Appendix 4A—Monoclonal Antibodies to Human Cell Surface Antigens," A.4A.1-A.4A.49.
Stockinger, H., et al., *Current Protocols in Immunology*, John Wiley & Sons, Inc., 2003, "Appendix 4B—Monoclonal Antibodies to Mouse Cell-Surface Antigens," A.4B.1-A.4B.25.
Stockinger, H., et al., *Current Protocols in Immunology*, John Wiley & Sons, Inc., 2003, "Appendix 4C—Monoclonal Antibodies to Rat Leukocyte Surface Antigens, MHC Antigens, and Immunoglobulins," A.4C.1-A.4C.12.
Tattersall et al., "Packed hyper-ellipsoid classifiers," *Electronics Letters* 30(5):427-428, 1994.
Terstappen et al., "Flow Cytometric Characterization of Acute Myeloid Leukemia, Part II. Phenotypic Heterogeneity at Diagnosis," *Leukemia* 6:70-80, 1992.
Terstappen et al., Myeloid Cell Differentiation in Normal Bone Marrow and Acute Myeloid Leukemia Assessed by Multi-Dimensional Flow Cytometry, *Analytical Cellular Pathology* 2.229-240, 1990.
Tyree et al., "The Use of Linked Line Segments for Cluster Representation and Data Reductions," *Pattern Recognition Letters* 20(1):21-29, 1999.
Verwer et al., "Automatic Lineage Assignment of Acute Leukemias by Flow Cytometry," *Cytometry* 14:862-875, 1993.
Weir et al., A Limited Antibody Panel can Distinguish B-Precursor Acute Lymphoblastic Leukemia from Normal B Precursors with Four Color Flow Cytometry:Implications for Residual Disease Detection, *Leukemia* 13:558-567, 1999.
Wells et al., "Multidimensional Flow Cytometry of Marrow Can Differentiate Leukemic From Normal Lymphoblasts and Myeloblasts After Chemotherapy and Bone Marrow Transplantation," *Am. J. Clin. Path.* 110:84-94, 1998.
Wells et al., "Myeloid and Monocytic Dyspoiesis as Determined by Flow Cytometric Scoring in Myelodysplastic Syndrome Correlates with the IPSS and with Outcome After Hematopoietic Stem Cell Transplantation," *Blood* 102(1):394-403, Jul. 2003.
Wells et al., "Occult B Cell Malignancies Can Be Detected By Three-Color Flow Cytometry in Patients with Cytopenias," *Leukemia* 12:2015-2023, 1998.

\* cited by examiner

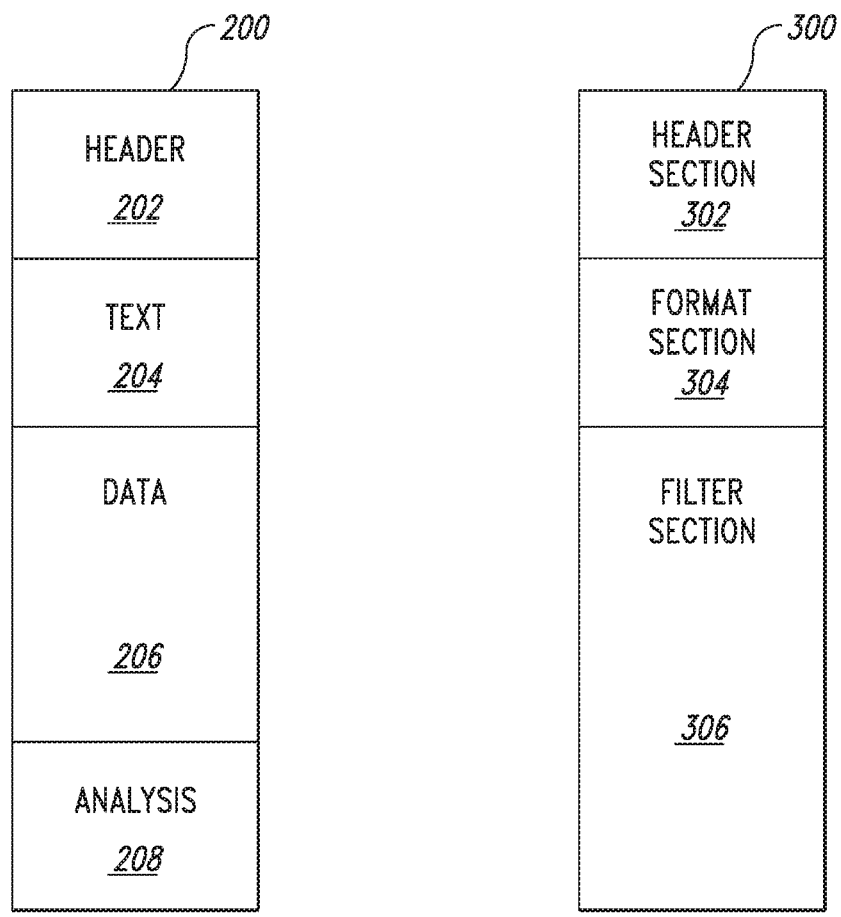

| | |
|---|---|
| FSC | 1.3 |
| SSC | 1.2 |
| FITC | 0.4 |
| PE | 0.3 |
| CD45 | 2.8 |
| CD34 | 0.5 |

| | |
|---|---|
| FSC | 1.2 |
| SSC | 1.4 |
| FITC | 0.1 |
| PE | 0.6 |
| CD45 | 2.6 |
| CD34 | 0.2 |

| | Standard Reference Mean | Test Patient Reference Population Mean | Normalization Vector |
|---|---|---|---|
| FSC | 1.3 | 1.2 | 0.1 |
| SCC | 1.2 | 1.4 | -0.2 |
| FITC | 0.4 | 0.1 | 0.3 |
| PE | 0.3 | 0.6 | -0.3 |
| CD45 | 2.8 | 2.6 | 0.2 |
| CD34 | 0.5 | 0.2 | 0.3 |

| | Unnormalized intensity of Cell #1 | Normalization Vector | Normalized Intensity for Cell #1 |
|---|---|---|---|
| FSC | 1.5 | 0.1 | 1.6 |
| SSC | 1.0 | -0.2 | 0.8 |
| FITC | 0.2 | 0.3 | 0.5 |
| PE | 0.5 | -0.3 | 0.2 |
| CD45 | 3.1 | 0.2 | 3.3 |
| CD34 | 0.2 | 0.3 | 0.5 |

FIG. 39

|  | FSC distance | SSC distance | CD20 distance | CD10 distance | CD45 distance | CD19 distance | Cluster |
|---|---|---|---|---|---|---|---|
| Cell 1 | -0.1 | 1.3 | -1.8 | 1.2 | 0.3 | 1.4 | 1 |
| Cell 2 | -0.7 | 1.9 | -0.9 | 0.8 | -0.1 | 1.2 | 1 |
| Cell 3 | -0.5 | 1.1 | 0.6 | 0.1 | 0.1 | 0.7 | 2 |
| ... | ... | ... | ... | ... | ... | ... | ... |
| Cell n | ... | ... | ... | ... | ... | ... | ... |

*FIG. 42*

(sd = $\sigma$)

| Cluster No. | FSC St.D | SSC St.D | CD20 St.D | CD10 St.D | CD45 St.D | CD19 St.D |
|---|---|---|---|---|---|---|
| 1 | 0.30 | 0.16 | 0.27 | 0.27 | 0.28 | 0.22 |
| 2 | 0.15 | 0.14 | 0.16 | 0.2 | 0.17 | 0.19 |
| 3 | 0.23 | 0.15 | 0.09 | 0.21 | 0.17 | 0.2 |
| ... | ... | ... | ... | ... | ... | ... |
| 10 | 0.26 | 0.18 | 0.25 | 0.16 | 0.17 | 0.24 |

*FIG. 43*

Means (corresponding to standard deviations)
(Mean = $\mu$)

| class | FSC mean | SSC mean | CD20 mean | CD10 mean | CD45 mean | CD19 mean |
|---|---|---|---|---|---|---|
| 1 | 0.02 | 0 | 0.01 | 0.01 | -0.08 | -0.05 |
| 2 | -0.05 | -0.03 | -0.1 | -0.04 | 0 | 0 |
| 3 | -0.06 | -0.02 | 0.02 | 0.01 | 0 | 0.01 |
| ... | ... | ... | ... | ... | ... | ... |
| 10 | -0.13 | -0.1 | -0.07 | -0.13 | -0.01 | 0.03 |

*FIG. 43A*

|   | FSC St. D. (scaled) | SSC St. D. (scaled) | CD20 St. D. (scaled) | CD10 St. D. (scaled) | CD45 St. D. (scaled) | CD19 St. D. (scaled) | Euclidian Distance St. D |
|---|---|---|---|---|---|---|---|
| 1 | 1 | 1 | 1 | 1 | 1 | 1 | 1.02 |
| 2 | 1 | 1 | 1 | 1 | 1 | 1 | 0.98 |
| 3 | 1 | 1 | 1 | 1 | 1 | 1 | 1.17 |
| ... | ... | ... | ... | ... | ... | ... | ... |
| 10 | 1 | 1 | 1 | 1 | 1 | 1 | 1.05 |

(Radius of each cluster)

*FIG. 45*

|   | FSC mean (scaled) | SSC mean (scaled) | CD20 mean (scaled) | CD10 mean (scaled) | CD45 mean (scaled) | CD19 mean (scaled) | Euclidian Distance mean |
|---|---|---|---|---|---|---|---|
| 1 | 0 | 0 | 0 | 0 | 0 | 0 | 2.22 |
| 2 | 0 | 0 | 0 | 0 | 0 | 0 | 2.23 |
| 3 | 0 | 0 | 0 | 0 | 0 | 0 | 2.15 |
| ... | ... | ... | ... | ... | ... | ... | ... |
| 10 | 0 | 0 | 0 | 0 | 0 | 0 | 2.20 |

(Mean of each cluster)

*FIG. 45A*

|        | FSC dist | SSC dist | CD20 dist | CD10 dist | CD45 dist | CD19 dist | Cluster No. |
|--------|----------|----------|-----------|-----------|-----------|-----------|-------------|
| Cell 1 | -0.02    | -0.04    | 0.22      | -0.2      | -0.18     | -0.27     | 1           |
| Cell 2 | -0.13    | 0.14     | 0.13      | 0         | -0.09     | 0.07      | 1           |
| Cell 3 | -0.14    | 0.12     | -0.10     | -0.32     | 0.15      | -0.62     | 6           |
| ...    | ...      | ...      | ...       | ...       | ...       | ...       | ...         |
| Cell n | ...      | ...      | ...       | ...       | ...       | ...       | ...         |

*FIG. 47*

|           | Cluster 1 Euc Dist | Cluster 2 Euc Dist | Cluster 3 Euc Dist | ... | Cluster 10 Euc Dist |
|-----------|--------------------|--------------------|--------------------|-----|---------------------|
| Patient 1 | 2.7                | 2.5                | 2.3                | ... | 2.2                 |
| Patient 2 | 2.6                | 2.7                | 2.6                | ... | 2.1                 |
| Patient 3 | 3.2                | 2.5                | 2.2                | ... | 2.9                 |
| ...       | ...                | ...                | ...                | ... | ...                 |
| Patient n | ...                | ...                | ...                | ... | ...                 |

(Distance Matrix)

*FIG. 48*

|           | Cluster 1 percentage | Cluster 2 percentage | Cluster 3 percentage | ... | Cluster 10 percentage |
|-----------|----------------------|----------------------|----------------------|-----|-----------------------|
| Patient 1 | 11%                  | 8%                   | 20%                  | ... | 6%                    |
| Patient 2 | 10%                  | 7%                   | 16%                  | ... | 8%                    |
| Patient 3 | 8%                   | 14%                  | 26%                  | ... | 6%                    |
| ...       | ...                  | ...                  | ...                  | ... | ...                   |
| Patient n | ...                  | ...                  | ...                  | ... | ...                   |

(Frequency Matrix)

*FIG. 49*

|  | Cluster 1 | Cluster 2 | Cluster 3 | ... | Cluster 10 |
|---|---|---|---|---|---|
| Mean Euc. Distance | 2.95 | 2.98 | 3.04 | ... | 4.41 |
| St. D. Euc. Distance | 0.48 | 0.57 | 0.75 | ... | 2.35 |

(Normal Position Matrix)

FIG. 50

|  | Cluster 1 | Cluster 2 | Cluster 3 | ... | Cluster 10 |
|---|---|---|---|---|---|
| Percentage | 10% | 13% | 16% | ... | 7% |

(Normal Percent Matrix)

FIG. 51

|        | FSC dist | SSC dist | CD20 dist | CD10 dist | CD45 dist | CD19 dist | Cluster No. |
|--------|----------|----------|-----------|-----------|-----------|-----------|-------------|
| Cell 1 | -0.02    | -0.04    | 0.22      | -0.2      | -0.18     | -0.27     | 1           |
| Cell 2 | -0.13    | 0.14     | 0.13      | 0         | -0.09     | 0.07      | 1           |
| Cell 3 | -0.14    | 0.12     | -0.10     | -0.32     | 0.15      | -0.62     | 6           |
| ...    | ...      | ...      | ...       | ...       | ...       | ...       | ...         |
| Cell n | ...      | ...      | ...       | ...       | ...       | ...       | ...         |

FIG. 53

|              | Cluster 1 | Cluster 2 | Cluster 3 | ... | Cluster 10 |
|--------------|-----------|-----------|-----------|-----|------------|
| Test Patient | 4.8       | 10.7      | 7.2       | ... | 9.6        |

(Test Patient Distance Matrix)

FIG. 54

|              | Cluster 1 | Cluster 2 | Cluster 3 | ... | Cluster 10 |
|--------------|-----------|-----------|-----------|-----|------------|
| Test Patient | 25%       | 17%       | 18%       | ... | 0%         |

(Test Patient Frequency Matrix)

FIG. 55

| | FSC dist | SSC dist | CD20 dist | CD10 dist | CD45 dist | CD19 dist | Cluster No. |
|---|---|---|---|---|---|---|---|
| Cell 1 | -0.02 | -0.04 | 0.22 | -0.2 | -0.18 | -0.27 | 1 |
| Cell 2 | -0.13 | 0.14 | 0.13 | 0 | -0.09 | 0.07 | 1 |
| Cell 3 | -0.14 | 0.12 | -0.10 | -0.32 | 0.15 | -0.62 | 6 |
| ... | ... | ... | ... | ... | ... | ... | ... |
| Cell n | ... | ... | ... | ... | ... | ... | ... |

*FIG. 59*

| | FSC St. D. (scaled) | SSC St. D. (scaled) | CD20 St. D. (scaled) | CD10 St. D. (scaled) | CD45 St. D. (scaled) | CD19 St. D. (scaled) | Euclidian Distance St. D |
|---|---|---|---|---|---|---|---|
| 1 | 1 | 1 | 1 | 1 | 1 | 1 | 1.02 |
| 2 | 1 | 1 | 1 | 1 | 1 | 1 | 0.98 |
| 3 | 1 | 1 | 1 | 1 | 1 | 1 | 1.17 |
| ... | ... | ... | ... | ... | ... | ... | ... |
| 10 | 1 | 1 | 1 | 1 | 1 | 1 | 1.05 |

*FIG. 60*

|       | FSC (scaled) | SSC (scaled) | CD20 (scaled) | CD10 (scaled) | CD45 (scaled) | CD19 (scaled) | Euc. Dist. | Cluster | Sub. Vector | Subtract Cell? |
|---|---|---|---|---|---|---|---|---|---|---|
| Cell 1 | 0.63 | 0.78 | 0.15 | -0.19 | 0.31 | -0.03 | 1.07 | 1 | 4.26 | Yes |
| Cell 2 | 5.84 | 2.69 | 1.59 | 2.46 | 0.55 | 0.96 | 7.15 | 1 | 4.19 | No |
| Cell 3 | 2.25 | 1.46 | -1.81 | -2.63 | -1.52 | 1.82 | 4.79 | 3 | 4.49 | No |
| ... | ... | ... | ... | ... | ... | ... | ... | ... | ... | ... |
| Cell n | ... | ... | ... | ... | ... | ... | ... | ... | ... | ... |

*FIG. 63*

|    | FSC St. D. (scaled) | SSC St. D. (scaled) | CD20 St. D. (scaled) | CD10 St. D. (scaled) | CD45 St. D. (scaled) | CD19 St. D. (scaled) | Euclidian Distance St. D |
|---|---|---|---|---|---|---|---|
| 1 | 1 | 1 | 1 | 1 | 1 | 1 | 1.02 |
| 2 | 1 | 1 | 1 | 1 | 1 | 1 | 0.98 |
| 3 | 1 | 1 | 1 | 1 | 1 | 1 | 1.17 |
| ... | ... | ... | ... | ... | ... | ... | ... |
| 10 | 1 | 1 | 1 | 1 | 1 | 1 | 1.05 |

*FIG. 60A*

| Radius Table | Selected Radius Mean (From Figure 45A) | Selected Radius St. D (From Figure 45) | Multiplication Factor | Subtraction Vector |
|---|---|---|---|---|
| Cluster 1 | 0 | 1 | 2 | 2 |
| Cluster 2 | 0 | 1 | 2 | 2 |
| Cluster 3 | 0 | 1 | 2 | 2 |
| ... | ... | ... | ... | ... |

*FIG. 61A*

| Radius Table | Selected Radius Mean | Selected Radius St. D | Multiplication Factor | Subtraction Vector |
|---|---|---|---|---|
| Cluster 1 | 2.22 | 1.02 | 2 | 4.26 |
| Cluster 2 | 2.23 | 0.98 | 2 | 4.19 |
| Cluster 3 | 2.15 | 1.17 | 2 | 4.49 |
| ... | ... | ... | ... | ... |

From Figure 45A · From Figure 45 · Selected radius mean + (multiplication factor × selected radius St. D)

*FIG. 61*

| | FSC (scaled) | SSC (scaled) | CD20 (scaled) | CD10 (scaled) | CD45 (scaled) | CD19 (scaled) | Euclidian Distance | Cluster | Sub. Vector |
|---|---|---|---|---|---|---|---|---|---|
| Cell 1 | 0.63 | 0.78 | 0.15 | -0.19 | 0.31 | -0.03 | 1.07 | 1 | 4.26 |
| Cell 2 | 5.84 | 2.69 | 1.59 | 2.46 | 9.55 | 0.96 | 7.15 | 1 | 4.19 |
| Cell 3 | 2.25 | 1.46 | -1.81 | -2.63 | -1.52 | 1.82 | 4.79 | 3 | 4.49 |
| ... | ... | ... | ... | ... | ... | ... | ... | ... | ... |
| Cell n | ... | ... | ... | ... | ... | ... | ... | ... | ... |

*FIG. 62*

|        | FSC (scaled) | SSC (scaled) | CD20 (scaled) | CD10 (scaled) | CD45 (scaled) | CD19 (scaled) | Euclidian Distance | Cluster | Sub. Vector |
|--------|------|------|-------|-------|-------|-------|-----------|---------|------|
| Cell 1 | 0.63 | 0.78 | 0.15  | -0.19 | 0.31  | -0.03 | 1.07      | 1       | 2    |
| Cell 2 | 5.84 | 2.69 | 1.59  | 2.46  | 0.55  | 0.96  | 7.15      | 1       | 2    |
| Cell 3 | 2.25 | 1.46 | -1.81 | -2.63 | -1.52 | 1.82  | 4.79      | 3       | 2    |
| ...    | ...  | ...  | ...   | ...   | ...   | ...   | ...       | ...     | ...  |
| Cell n | ...  | ...  | ...   | ...   | ...   | ...   | ...       | ...     | ...  |

*FIG. 62A*

|        | FSC (scaled) | SSC (scaled) | CD20 (scaled) | CD10 (scaled) | CD45 (scaled) | CD19 (scaled) | Euc. Dist. | Cluster | Sub. Vector | Subtract Cell? |
|--------|------|------|-------|-------|-------|-------|------|---------|------|-----|
| Cell 1 | 0.63 | 0.78 | 0.15  | -0.19 | 0.31  | -0.03 | 1.07 | 1       | 2    | Yes |
| Cell 2 | 5.84 | 2.69 | 1.59  | 2.46  | 0.55  | 0.96  | 7.15 | 1       | 2    | No  |
| Cell 3 | 2.25 | 1.46 | -1.81 | -2.63 | -1.52 | 1.82  | 4.79 | 3       | 2    | No  |
| ...    | ...  | ...  | ...   | ...   | ...   | ...   | ...  | ...     | ...  | ... |
| Cell n | ...  | ...  | ...   | ...   | ...   | ...   | ...  | ...     | ...  | ... |

*FIG. 63A*

SYSTEM, METHOD, AND ARTICLE FOR DETECTING ABNORMAL CELLS USING MULTI-DIMENSIONAL ANALYSIS

CROSS REFERENCE TO RELATED APPLICATION

This application claims the benefit under 35 U.S.C. § 119(e) to U.S. Provisional Application No. 62/396,621 filed on Sep. 19, 2016, which application is incorporated by reference herein in its entirety.

BACKGROUND

Technical Field

This disclosure is directed to multi-dimensional analysis of measured cell characteristics and in particular to a system, method and article for detecting abnormal cells in a test set of cells using multi-dimensional analysis of cell characteristics measured using flow cytometry.

Description of the Related Art

One method for characterizing heterogeneous cell populations is by flow cytometry, originally developed by Herzenberg and co-workers (Science. 1969 166(906):747-9; *J Histochem Cytochem.* 1976 24(1):284-91; *Clin Chem.* 1973 19(8):813-6; Ann. N.Y. Acad. of Sci. 1975 254:163-171). Using this technology, cells are labeled with antibodies conjugated to dyes. Flow cytometry can routinely detect 3, 4 or more immunofluorescent markers simultaneously in a quantitative manner. By combining multiple immunofluorescent labels with the light scattering properties of the cells it is possible to distinguish not only between cells of different lineages but between cells at various stages of maturation within those lineages. This is determined based on expression patterns of unique cell surface antigens (See for example, Loken M R, et al., in Flow Cytometry in Hematology. Laerum O D, Bjerksnes R. eds. Academic Press, New York, pp 31-42, 1992; Civin C I, et al., in "Concise Reviews in Clinical and Experimental Hematology" Martin J. Murphy ed. AlphaMed Press, Dayton Ohio, 1992, pp 149-159). Populations identified by the flow cytometer can then be isolated using the cell sorting electronics available on the instrument.

Multi-parameter flow cytometry is currently used to detect a variety of leukemias. However, current techniques require that time consuming data analysis be performed by a professional, namely someone well versed in both flow cytometry and hematopathology, such as a doctor. There is a long learning process required to educate a professional to make the distinction between normal and abnormal cell populations. In addition, when flow cytometry is used to monitor a patient's response to therapy, conventional techniques require the use of patient-specific panels for detecting residual disease.

Accordingly, there remains a need in the art for technology to improve accuracy of detection and simplify data analysis. The present disclosure may fulfill this and other needs.

BRIEF SUMMARY

In one embodiment a normal set of cells is characterized using flow cytometry. A centroid and radius are defined for a set of clusters in an n-dimensional space corresponding to a normal maturation for a cell lineage in the normal set of cells. A test set of cells is characterized using flow cytometry and the characterization is compared to the set of clusters. This approach facilitates the detection of low levels of tumor cells based on their phenotypic differences from their normal counterparts as assessed by an analysis of complex data from normal and abnormal cell populations.

In one aspect, an embodiment comprises a method of diagnosing cancer in a test set of biological cells in an n-dimensional space, the method comprising: exposing each cell in a normal set of biological cells to a plurality of four or more reagents using a first protocol; measuring a corresponding plurality of fluorescence intensities of each cell in the normal set of biological cells using a second protocol; mapping each cell in the normal set of biological cells to a corresponding point in an n-dimensional space based at least in part on the measured plurality of fluorescence intensities of the cell in the normal set of biological cells, wherein the corresponding points form a normal set of points; defining a set of normal clusters in the n-dimensional space by defining a centroid line and radius based on the mapping of the normal set of points in the n-dimensional space, wherein each cluster in the set of normal clusters corresponds to a maturation level within a cell lineage; exposing each cell in a test set of biological cells to the plurality of reagents using the first protocol; measuring a corresponding plurality of fluorescence intensities of each cell in the test set of biological cells using the second protocol; mapping each cell in the test cell of biological cells to a corresponding point in an n-dimensional space based at least in part on the measured plurality of fluorescence intensities of the cell in the test set of biological cells, wherein the corresponding points form a test set of points; and comparing the test set of points to the set of normal clusters.

In one aspect, a method comprises exposing a cell to a plurality of any number of reagents. Some instruments are capable of producing nine or more colors. The use of increased reagents and colors facilitates the characterization of cells.

In another aspect, an embodiment comprises a method of characterizing a test set of biological cells in an n-dimensional space, the method comprising: mapping each cell in a normal set of biological cells to a corresponding point in an n-dimensional space using a first protocol, wherein the corresponding points form a normal set of points; defining a centroid and radius for a set of normal clusters in the n-dimensional space based on the mapping of the normal set of points in the n-dimensional space, wherein a cluster corresponds to a maturation level within a cell lineage; mapping each cell in a test set of biological cells to a corresponding point in the n-dimensional space using the first protocol, the corresponding points forming a test set of points; and comparing the test set of points to the set of normal clusters.

In another aspect, an embodiment comprises a method of diagnosing a test set of biological cells, the method comprising: mapping each cell in the test set of biological cells to a corresponding point in an n-dimensional space using a defined protocol, the corresponding points forming a test set of points; and comparing the test set of points to a defined set of normal clusters in the n-dimensional space, wherein a cluster in the defined set of normal clusters corresponds to a maturation level within a cell lineage and a cluster is defined by a centroid and radius.

In another aspect an embodiment comprises a method of characterizing a test set of biological cells, the method comprising: mapping each cell in the test set of biological cells to a corresponding point in an n-dimensional space using a defined protocol, the corresponding points forming a test set of points; representing the test set of points in a Cartesian coordinate display comprising a first axis corresponding to a cell maturation within a cell lineage and a second axis corresponding to a frequency of occurrence; and representing in the Cartesian coordinate display a set of normal clusters in the n-dimensional space, wherein a cluster is defined by a centroid and a radius and corresponds to a cell maturation level within a cell lineage.

In another aspect an embodiment comprises a method of characterizing a normal cell lineage in an n-dimensional space, the method comprising: exposing each cell in a normal set of biological cells to a plurality of reagents using a first protocol; measuring a corresponding plurality of characteristics of each cell in the normal set of biological cells using a second protocol; mapping each cell in the normal set of biological cells to a corresponding point in an n-dimensional space based at least in part on the measured plurality of characteristics of the cell in the normal set of biological cells, wherein the corresponding points form a normal set of points; and defining a centroid and radius for a set of clusters based on the mapping of the normal set of points in the n-dimensional space, wherein each cluster corresponds to a maturation level within the normal cell lineage.

In another aspect an embodiment comprises a computer readable media storing instructions for causing a diagnostic system to facilitate a detection of cancerous cells in a test set of biological cells by: retrieving a first set of data comprising indications of a plurality of three or more fluorescence intensities for each cell in a normal set of biological cells measured using a defined protocol; mapping each cell in the normal set of biological cells to a corresponding point in an n-dimensional space based at least in part on the first set of data, wherein the corresponding points form a normal set of points; defining a centroid line and radius for a set of normal clusters in the n-dimensional space based on the mapping of the normal set of points in the n-dimensional space, wherein a cluster corresponds to a maturation level within a cell lineage; retrieving a second set of data comprising indications of a corresponding plurality of fluorescence intensities for each cell in a test set of biological cells measured using the defined protocol; mapping each cell in the test cell of biological cells to a corresponding point in an n-dimensional space based at least in part on the second set of data, wherein the corresponding points form a test set of points; and comparing the test set of points to the set of normal clusters.

In another aspect an embodiment comprises a computer readable media storing instructions for causing a diagnostic system to facilitate a detection of cancerous cells in a set of biological cells by: retrieving a first set of data; defining a centroid line and radius for a set of normal clusters in an n-dimensional space based on the first set of data, wherein a cluster in the set of normal clusters corresponds to a normal maturation level within a cell lineage; retrieving a second set of data; and comparing the second set of data to the set of normal clusters.

In another aspect an embodiment comprises a computer readable media storing instructions for causing a control system to facilitate a diagnosis of cells in a test set of biological cells by: receiving a first set of data corresponding to a plurality of fluorescence intensities for a normal set of biological cells measured using a defined protocol; defining a set of normal clusters in a multi-dimensional space based on the first set of data, wherein a cluster is defined by a centroid line and radius and corresponds to a cell maturation level within a cell lineage; receiving a second set of data corresponding to indications of a corresponding plurality of fluorescence intensities for each cell in a test set of biological cells measured using the defined protocol; and comparing the second set of data to the defined set of normal clusters.

In another aspect an embodiment comprises a computer readable media containing a data structure for use in characterizing a test set of biological cells, the data structure comprising: a header section; a text section; and a data section, wherein the text section contains information regarding the data section and the data section contains information to define a centroid and radius for a set of normal clusters and wherein a cluster in the normal set of clusters corresponds to a normal maturation level within a cell lineage. In another aspect an embodiment of a diagnostic system comprises: a controller; a memory; a data interface; a control interface; and a graphics engine, wherein the diagnostic system is configured to compare a test set of data to a set of normal clusters in an n-dimensional space defined by a centroid and radius, and wherein a cluster in the set of normal clusters corresponds to a normal maturation level within a cell lineage.

In another aspect an embodiment of a system for diagnosing a test set of cells comprises: means for defining a set of normal clusters corresponding to a normal cell lineage; and means for comparing the test set of cells to the set of normal clusters.

BRIEF DESCRIPTION OF THE DRAWINGS

FIG. 2 is a schematic diagram of a data structure suitable for storing data related to a set of biological cells.

FIG. 3 is a schematic diagram of a data structure suitable for storing information related to processing of data contained in the data structure illustrated in FIG. 2.

FIGS. 4A to 9A and 4B to 9B are illustrations of multi-dimensional data projected into pseudo two-dimensional displays generated by a system, such as the system illustrated in FIG. 1.

FIGS. 12A to 17A and 12B to 17B are illustrations of multi-dimensional data projected into pseudo two-dimensional displays generated by a system, such as the system illustrated in FIG. 1.

FIG. 39 illustrates application of a normalization vector to normalize intensities of a test patient data set.

FIG. 42 is an illustration, in the form of a float array, of parameter distance values between cells (data points) of a data set and corresponding tangential intersection points between the cells (data points) and a centroid line defining a set of normal clusters.

FIG. 43 is an illustration, in the form of a float array, of standard deviations of parameters in clusters for combined normal patient data sets.

FIG. 43A is an illustration, in the form of a float array, of mean distances between a cell and the cell's tangential intersection point with the centroid line.

FIG. 45 is an illustration, in the form of a float array, of scaled standard deviations in clusters for combined normal patient data sets.

FIG. 45A is an illustration, in the form of a float array, of a standardized mean distances of clusters for combined normal patient data sets.

FIG. 47 is an illustration, in the form of a float array, of parameter distance values between cells (data points) of a data set and corresponding tangential intersection points between the cells (data points) and a centroid line defining a set of normal clusters, including Euclidean distances and cluster numbers.

FIG. 48 is an illustration, in the form of a float array, of a mean distance matrix of cells (data points) in clusters for normal patient data sets.

FIG. 49 is an illustration, in the form of a float array, of a frequency matrix of cells (data points) in clusters for normal patient data sets.

FIG. 50 is an illustration, in the form of a float array, of a normal position matrix of a combined set of cells (data points) of normal patients.

FIG. 51 is an illustration, in the form of a float array, of a normal percent matrix of cells (data points) in clusters of a combined set of cells (data points) of normal patients.

FIG. 53 is an illustration, in the form of a float array, of parameter distance values between cells (data points) of a test patient data set and corresponding tangential intersection points between the cells (data points) and a centroid line defining a set of normal clusters, including Euclidean distances and cluster numbers.

FIG. 54 is an illustration, in the form of a float array, of a mean distance matrix of cells (data points) of clusters of a test patient data set.

FIG. 55 is an illustration, in the form of a float array, of a frequency matrix of cells (data points) in clusters for a test patient data set.

FIG. 59 is an illustration, in the form of a float array, of parameter distance values between cells (data points) of a test patient data set and corresponding tangential intersection points between the cells (data points) and a centroid line defining a set of normal clusters, including Euclidean distances and cluster numbers.

FIGS. 60 and 60A are illustrations, in the form of float arrays, of normal radius tables of a combined set of normal clusters.

FIGS. 61, 61A, 62 and 62A are illustrations, in the form of float arrays, of information to use to filter cells (data points) to represent in an image of a test patient data set.

FIGS. 63 and 63A are illustrations, in the form of float arrays, of cells to include in (or exclude from) an image representing a test patient data set.

DETAILED DESCRIPTION

Figure 1:
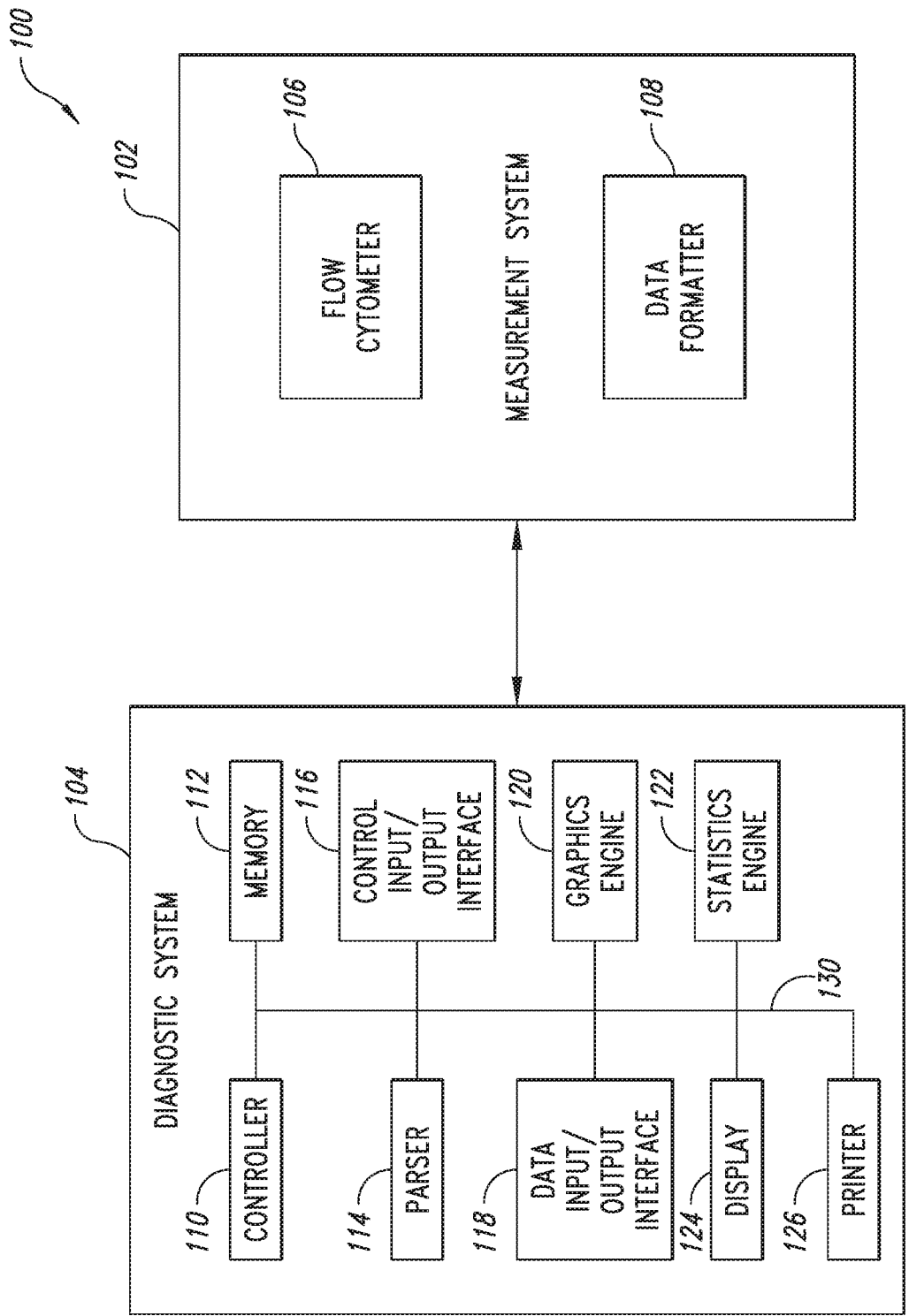
FIG. 1 is a functional block diagram of a system implementing an embodiment of a method of diagnosing a test set of cells.
Figure 4A:
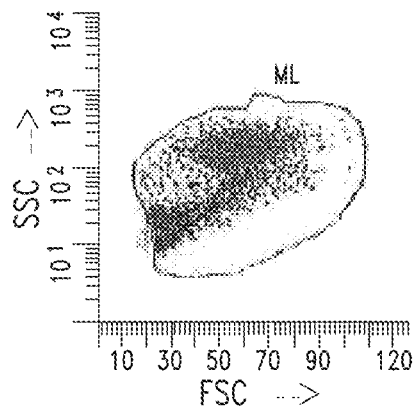

In the following description, certain details are set forth in order to provide a thorough understanding of various embodiments of devices, systems, methods and articles. However, one of skill in the art will understand that other embodiments may be practiced without these details. In other instances, well-known structures and methods associated with, for example, flow cytometers, controllers, etc., such as power supplies, transistors, memory, logic gates, buses, etc., have not been shown or described in detail in some figures to avoid unnecessarily obscuring descriptions of the embodiments.

Unless the context requires otherwise, throughout the specification and claims which follow, the word "comprise" and variations thereof, such as "comprising," and "comprises," are to be construed in an open, inclusive sense, that is, as "including, but not limited to."

Reference throughout this specification to "one embodiment," or "an embodiment" means that a particular feature, structure or characteristic described in connection with the embodiment is included in at least one embodiment. Thus, the appearances of the phrases "in one embodiment," or "in an embodiment" in various places throughout this specification are not necessarily referring to the same embodiment, or to all embodiments. Furthermore, the particular features, structures, or characteristics may be combined in any suitable manner in one or more embodiments to obtain further embodiments.

The headings are provided for convenience only, and do not interpret the scope or meaning of this disclosure.

The sizes and relative positions of elements in the drawings are not necessarily drawn to scale. For example, the shapes of various elements and angles are not drawn to scale, and some of these elements are enlarged and positioned to improve drawing legibility. Further, the particular shapes of the elements as drawn are not necessarily intended to convey any information regarding the actual shape of particular elements, and have been selected solely for ease of recognition in the drawings.

Gene products can be identified on the cell surface or in the cytoplasm of cells using specific monoclonal antibodies. Flow cytometry can be used to detect multiple immunofluorescent markers simultaneously in a quantitative manner.

The technique of immunofluorescent staining is well known and can be carried out according to any of a variety of protocols, such as those described in Current Protocols in Cytometry (John Wiley & Sons, NY, NY, Eds. J. Paul Robinson, et al.). Generally, a biological sample, such as peripheral blood, bone marrow, lymph node tissue, cord blood, thymus tissue, tissue from a site of infection, spleen tissue, tumor tissue, and the like, is collected from a subject and cells are isolated therefrom using techniques known in the art. In one embodiment, blood is collected from a subject and any mature erythrocytes are lysed using a buffer, such as buffered $NH_4Cl$. The remaining leukocytes are washed and then incubated with antibodies (e.g., monoclonal antibodies) conjugated to any of a variety of dyes (fluorophores) known in the art (see for example, http colon double slash www dot glenspectra dot co dot uk/glen/filters/fffluorpn dot htm or http colon double slash cellscience dot bio-rad dot com/ fluorescence/fluorophoradata dot htm). Representative dyes in this context include, but are not limited to, FITC (Fluorescein Isothiocyante), R-phycoerythrin (PE), Allophycocyanin (APC), Cy7®, and Texas Red.

A wide variety of antibodies known in the art, and specific antibodies generated using techniques well known in the art, are useful in the context of the presently disclosed embodiments. Generally, the antibodies for use in the methods described herein are specific for a cell marker of interest, such as any of the CD cell surface markers (see for example the CD index at httpcolon double slash www dot ncbi dot nlm dot nih dot gov/PROW/guide/45277084 dot html; or Current Protocols in Immunology, John Wiley & Sons, NY, NY), cytokines, adhesion proteins, developmental cell surface markers, tumor antigens, or other proteins expressed by a cell population of interest. An antibody specific for virtually any protein expressed by a cell is useful in the context of the present disclosure. Illustrative antibodies include, but are not limited to antibodies that specifically bind to CD3, CD33, CD34, CD8, CD4, CD56, CD19, CD14, CD15, CD16, CD13, CD38, CD71, CD11 b, HLA-DR, glycophorin, CD45, CD20, CD5, CD7, CD2, CD10 and TdT.

After a period of incubation with a dye-conjugated antibody, typically about 20 minutes in the dark (incubation times and conditions may vary according to particular protocols), the leukocytes are washed with buffered saline and resuspended in buffered saline containing protein for introduction into a flow cytometer.

The flow cytometer analyzes the heterogeneous cell population one cell at a time and can classify the cells based on the binding of the immunofluorescent monoclonal antibody and the light scattering properties of each cell (see, for example, Immunol Today. 2000 21(8):383-90). Fluorescence detection is accomplished using photomultiplier tubes; the number of detectors (channels) determines the number of optical parameters the instrument can simultaneously examine while bandpass filters ensure that only the intended wavelengths are collected. Thus, flow cytometry can routinely detect multiple immunofluorescent markers in a quantitative manner and can measure other parameters such as forward light scatter (which is an indication of cell size) and right angle light scatter (which is an indication of cell granularity). Accordingly, a wide variety of cell populations can be differentiated and sorted using immunofluorescence and flow cytometry.

For example, by combining 4 colors of immunofluorescence with the physical parameters of forward light scatter (measure of cell size) and right angle light scatter (measure of cell granularity), a six dimensional data space can be generated wherein specific cell populations found in normal blood or bone marrow are restricted to small portions of the data space. As would be recognized by the skilled artisan after reviewing the specification, more or less than 4 colors of immunofluorescent markers could also be used. Excitation of fluorophores is not limited to light in the visible spectrum; several dyes, such as the Indo series (for measuring intracellular calcium) and the Hoechst series (for cell-cycle analyses) are excitable in the ultraviolet range. Thus, some instruments currently available in the art are configured with ultraviolet-emitting sources, such as the four-laser, 10-color Becton Dickinson LSR II. Further, using a commercially available fluorescence activated cell sorter, such as the FACSVANTAGE™ (Becton Dickinson, San Jose, Calif.), the EPICS® ALTRA™ (Beckman Coulter, Fullerton, Calif.) or the MOFLO® sorter (DakoCytomation, Inc., Carpinteria, Calif.) cell populations can also be sorted into purified fractions. Gene expression observed during the development of blood cells from hematopoietic stem cells to mature cells found in blood is a highly regulated process. See Civin C I, Loken M R: *Cell Surface Antigens on Human Marrow Cells: Dissection of Hematopoietic Development Using Monoclonal Antibodies and Multiparameter Flow Cytometry*, Intl J. Cell Cloning 5:1-16 (1987), which is incorporated herein by reference in its entirety. Thus, specific, tightly controlled expression of genes occurs within not only different lineages of blood cells but also during different stages of maturation within those lineages. See Loken, M R, Terstappen L W M M, Civin C I, Fackler, M J: *Flow Cytometry Characterization of Erythroid, Lymphoid and Monomyeloid Lineages in Normal Human Bone Marrow*, Flow Cytometry in Hematology, Laerum O D, Bjerksnes R. eds., Academic Press, New York, pp. 31-42 (1992), which is incorporated herein by reference in its entirety. Not only do these gene products appear and/or disappear at precise stages of maturation, but the amounts of these glycoproteins are regulated within very tight limits in normal cells. It has been shown that these antigenic relationships are established early in fetal development and are constant throughout adult life on blood cells that are undergoing constant turnover and replenishment. See LeBein T W, Wormann B, Villablanca J G, Law C L, Shah V O, Loken M R: *Multiparameter Flow Cytometric Analysis of Human Fetal Bone Marrow B Cells*, Leukemia 4:354-358 (1990), which is incorporated herein be reference in its entirety. These patterns and relationships of gene expression during maturation of normal cells are maintained following chemotherapy or even bone marrow transplantation. See Wells D A, Sale G E, Shulman H E, Myerson D, Bryant E, Gooley T, Loken M R: *Multidimensional Flow Cytometry of Marrow Can Differentiate Leukemic Lymphoblasts From Normal Lymphoblasts and Myeloblasts Following Chemotherapy and/or Bone Marrow Transplant*, Am. J. Clin. Path. 110:84-94 (1998), which is incorporated herein by reference in its entirety. Therefore, there is a very tightly coordinated regulation of multiple genes during normal development of blood cells both in terms of timing of expression as well as regulation of amounts of gene products expressed on the cell surfaces.

A comparison of normal antigen expression to neoplastic processes indicates that regulation of gene expression is disrupted in neoplastic cells. This disruption gives rise to different antigenic relationships than those observed during normal maturation of cells. See Hurwitz, C A, Loken M R, Graham M L, Karp J E, Borowitz M J, Pullen D J, Civin C I: *Asynchronous Antigen Expression in B Lineage Acute Lymphoblastic Leukemia*, Blood, 72:299-307 (1998). These are not new antigens, but are those normally expressed gene products that have lost the coordinated regulation found in normal cells. Both acute lymphoblastic leukemia ("ALL") and acute myeloblastic leukemia ("AML") express antigens abnormally. See Terstappen L W M M, Loken M R: *Myeloid Cell Differentiation in Normal Bone Marrow and Acute Myeloid Leukemia Assessed by Multi-Dimensional Flow Cytometry*, Anal. Cell Path. 2:229-240 (1990), which is incorporated herein by reference in its entirety. The types of abnormalities include:

(1) Lineage infidelity, defined as the expression of non-lineage antigens;
 (2) Antigenic asynchrony, e.g., the expression on mature cells of antigens that normally appear on immature cells;
 (3) Antigenic absence; and
 (4) Quantitative abnormalities.

See Terstappen L W M M, Konemann S, Safford M, Loken M R, Zurlutter K, Buchner Th, Hiddemann W, Wormann B: *Flow Cytometric Characterization of Acute Myeloid Leukemia, Part II. Phenotypic Heterogeneity at Diagnosis*, Leukemia 6:70-80 (1991), which is incorporated herein by reference in its entirety.

Not only are phenotypes of leukemic cells different from normal, the relationships between antigens are different from one case to the next, suggesting that each leukemic transformation causes a loss of coordinated gene regulation resulting in a unique phenotypic pattern for each leukemia. In 120 pediatric ALL cases and 86 adult AML cases each detailed phenotype was different from normal and from each other. See Id.; Hurwitz, supra. Thus, neoplastic transformation affects primary DNA sequence (genotype) and the regulation of normal genes so that they are inappropriately expressed at the wrong time during development, expressed in the wrong amounts, and/or are expressed in context with other genes that are not observed in normal cells (phenotype). The loss of coordinated gene regulation appears to be a hallmark of neoplastic transformation that results in abnormal phenotypes where each leukemic clone is different from normal and is different from other leukemias of the same type.

It should be noted that embodiments are not limited to the analysis of leukemic cells (e.g., acute and chronic lymphocytic leukemias (ALL, CLL) and acute and chronic myelogenous leukemia (AML, CML)) and other hematopoietic and lymphoid neoplastic cells. Embodiments can be applied to analysis of any of a variety of malignancies, e.g., lymphoma, myeloma or pre malignancies such as myelodysplasia, and other disorders, including any of a variety of hematologic disorders.

Flow cytometry can be adopted to use this phenotypic difference from normal to aid in the diagnosis of leukemia as well as in monitoring response to therapy. Flow cytometry has been used in hematopathology to phenotype the tumor, e.g., differentiating AML from ALL. However, conventional approaches require that the cells of interest form a predominant portion of the total cells examined and that the expected disease process be known before the analysis is performed, such as when a morphologic examination identifies a leukemic cell population of uncertain subtype. The focus on neoplastic cells can extend to residual disease detection. However, conventional residual disease detection techniques employing flow cytometry require a patient specific reagent panel to identify the specific phenotype observed at diagnosis. See Reading C I, Estey E H, Huh Y O, Claxton D F, Sanchez G, Terstappen L W, O'Brien M C, Baron S, Deisseroth A B, *Expression of Unusual Immunophenotype Combinations in Acute Myelogenous Leukemia*, Blood 81:3083-3090 (1993), which is incorporated herein by reference in its entirety. Such patient specific panels have been used to detect residual ALL and AML down to levels of 0.03-0.05%. See Coustan-Smith E, Sancho J, Hancock M L, Boyett J M, Behm F G, Raimondi S C, Sandlund J T, Rivera G K, Rubnitz J E, Ribeiro R C, Pui C H, Campana D, *Clinical Importance of Minimal Residual Disease in Childhood Acute Lymphoplastic Leukemia*, Blood 96:2691-2696 (2001); San Miguel J F, Vidriales M B, Lopez-Berges C, Diaz-Mediavilla J, Gutierrez N, Canizo C, Ramos F, Calmunitia M J, Perez J, Gonzalez M, Orfao A, *Early Immunophenotypical Evaluation of Minimal Residual Disease in Acute Myeloid Leukemia Identifies Different Patient Risk Groups and may Contribute to Postinduction Treatment Stratification*, Blood 98:1746-1751 (2002), which are incorporated herein by reference in their entirety.

Conventional detection of residual disease using patient specific reagent panels, however, suffers from the following limitations:

1. A diagnostic specimen with an aberrant phenotype is required in order to construct a panel. In 25% of cases an aberrant phenotype may not be identifiable. See Vidriales, supra.

2. Processing time is substantial because a technician must examine prior analysis for the particular patient in order to determine the reagent combination to use in each case.

3. The phenotype of a leukemic cell population that is different than the originally diagnosed phenotype may not be detected. For example, the phenotype may change from diagnosis to relapse as a result of clonal evolution or an outgrowth of a minor chemotherapy resistant subclone. See San Miguel, supra.

4. Unexpected or unanticipated abnormalities, such as secondary myelodysplasia or abnormalities in other lineages may be overlooked.

The assessment of residual disease using patient specific panels can work well in a controlled environment, such as a research study where there is access to all sequential specimens and there is high compliance in obtaining specimens at specific times in therapy. In clinical practice, however, a flow cytometry laboratory may be asked to perform residual disease analysis when the laboratory did not perform the initial diagnosis. A detailed immunophenotype is often unavailable or incomplete.

Residual disease detection can also be performed using standardized panels and difference from normal as the tumor specific marker. Coordinated gene expression is so precise that a divergence of ½ a decade in antigen expression is sufficient for the discrimination between normal and aberrant neoplastic cells. In such an approach, specific reagent panels are used for each suspected lineage, for example, B lineage ALL; T lineage ALL; AML; B lineage non-Hodgkins lymphoma ("B-NHL") and T lineage NHL ("T-NHL"), as well as MDS and myeloma. Tumor populations can be identified by first identifying patterns expected of normal cells, then focusing on cells that do not match the patterns expected of normal cells. This approach of detecting residual disease has been used by the Fred Hutchinson Cancer Research Center for several years and has been successful in predicting outcomes in hematopoietic neoplasms. For example:

1. In hematopoietic stem cell transplants for ALL, flow cytometry was shown to be more sensitive and more specific than morphology, cytogenetics, or the two technologies combined, in predicting relapse for 120 patients. See Wells, D A, supra.

2. In pediatric AML flow cytometric detection of residual disease was the best predictor of outcome in 252 patients studied. Sievers, E. L., Lange, B. J., Alonzo, T. A., Gerbing, R. B., Bernstein, I. D., Smith, F. O., Arceci, R. J., Woods, W. G., Loken, M. R., *Immunophenotypic evidence of leukemia after induction therapy predicts relapse: results from a prospective Children's Cancer Group study of 252 patients with acute myeloid leukemia*, Blood 101: 3398-3406 (2003). Patients with detectable tumor at any time during therapy were 4 times more likely to relapse and 3 times more likely to die than those patients in whom no tumor was detected.

3. In hematopoietic stem cell transplants flow cytometry is able to distinguish between normal regenerating blasts and recurrent tumor based on aberrant antigen expression. See Shulman H, Wells D, Gooley T, Myerson D, Bryant E, Loken M., *The biologic significance of rare peripheral blasts after hematopoietic cell transplant is predicted by multidimensional flow cytometry*, Am J Clin Path 112:513-523 (1999). Patients can exhibit 20% normal blasts in the blood or may have up to 50% regenerating blasts in the marrow without detection of neoplastic cells.

The detection of abnormal phenotypes of small populations of cells in blood or bone marrow extends the utility of flow cytometry to other applications beyond simply phenotyping leukemias. Flow cytometry has been used to show that a significant proportion (10%) of patients with a diagnosis of myelodysplasia have been misdiagnosed and have lymphoid, not myeloid abnormalities. See Wells D A, Hall M C, Shulman H E, Loken M R, *Occult B cell malignancies can be detected by three-color flow cytometry in patients with cytopenias*, Leukemia 12:2015-2023 (1998). Flow cytometry has also allowed the development of a scoring system to stratify patients with myelodysplasia based on the degree of abnormalities detected among the maturing myeloid cells. See Wells, D., Benesch, M, Loken, M., Vallejo, C., Myerson, D., Leisenring, W., Deeg, H., *Myeloid and monocytic dyspoiesis as determined by flow cytometric scoring in myelodysplastic syndrome correlates with the IPSS and with outcome after hematopoietic stem cell transplantation*, Blood 102: 394-403 (2003). The patients with myeloid cells that exhibited more aberrancies in gene expression as evidenced by abnormal immunophenotype, had a higher relapse rate and death post stem cell transplant as compared to patients with fewer detectable abnormalities. There was also a high correlation with the International Prognostic Scoring System (IPSS). In addition, a high flow cytometric score divided the Intermediate I group of patients in the IPSS system into statistically significant groups based on relapse post stem cell transplant.

There are several advantages of tumor detection based on difference from normal.

1. The technique does not require a diagnostic specimen for creation of a specific panel.

2. The approach allows for rapid processing of specimens in a high volume laboratory with identical panels being used for different patients.

3. The results are not affected by a change in phenotype following therapy.

4. Proper standardized panel selection permits the detection of unexpected or unanticipated findings that are the result of hematologic abnormalities.

Conventional distinction between normal and abnormal cell populations does have significant limitations. Data analysis conventionally must be performed by a professional (MD or PhD well versed in both flow cytometry and hematopathology) and not by a technician, since various clinical situations may indicate if abnormalities observed are normal or abnormal. There is a long learning process required to educate a professional to make the distinction between normal and abnormal cell populations. A well-trained hematopathologist may take 6 months to a year to learn the techniques. Currently, the assessment of normal against abnormal by the professional is based on experience with all the inherent difficulties of a subjective analysis, similar to the training in diagnostic microscopy. It is difficult to extend the analysis to other sites and maintain the same sensitivity and specificity. In difficult cases two or more professionals must come to a consensus for a final diagnosis.

For example, Weir, et al. describe a normal "template" resulting from four-color flow cytometric analysis of normal B cell precursors against which tumor samples can be compared. See Weir, E. G., et al., Leukemia (1999) 13:558-567. However, unlike the present disclosure, this template is a specific, fixed set of geometric regions drawn around the displayed dot plot events, which are then used as the boundaries of normal. As noted by Weir, et al., isolated events of uncertain nature present in normal samples that fall outside the template-defined boundaries of normal present a serious problem that has yet to be resolved with their method, particularly in the setting of minimal residual disease detection. Additionally, as with other prior methods, analysis by a highly trained individual is required to compare patient samples against the template.

In addition, the populations identified by multiple monoclonal antibodies in normal bone marrow are not distinct spherical clouds in multi-dimensional space. Rather, the data can be described as a series of tubes or snakes that change in size and position as lineages of cells traverse from immature to mature forms traveling from head to tail in the multi-dimensional data space. Thus, cluster analysis programs that treat data as spherical clouds, produce results with the limitations described above.

In contrast, the embodiments described further herein provide a method for determining, among other things, a centroid line and radius of one or more clusters of events corresponding to a normal cell maturation lineage. In this manner, statistical analysis can be used to determine whether an event represents an abnormal event (i.e., cancer).

Normal bone marrow is comprised of multiple lineages each undergoing continuous, steady state maturation. By first assessing normal cells, a statistical measure of what constitutes normal and what constitutes abnormal can be defined. This definition then becomes the standard for analysis. Automating the identification of which cells are within the expected, defined positions of normal will facilitate the teaching of new professionals and technicians as to what is phenotypically abnormal. It will also permit the standardization of analysis at multiple sites providing consistency between analysts in identifying abnormal populations.

Automating the identification of abnormal cells also allows for increased sensitivity. Current manual evaluation is performed using three antibodies in combination with forward and right angle light scatter collecting 10,000 events for each tube. A panel consists of between seven and fourteen different tubes each with a different combination of antibodies. Using this current system, tumors can be detected with specificity approaching 100%. See Am. J. Clin. Path. 110:84-94, supra; Blood 98:1746-1751, supra; Blood 101:3398-3406, supra. It is possible for a single professional to analyze and report between 20-30 such cases in a single day. Increasing sensitivity is a limitation under conventional approaches because the professional must spend more time analyzing each case. Automating the identification of abnormal cells will permit larger data sets (counting more cells) and application of more antibodies, without increasing the time an analyst must spend on each specimen.

The statistical analysis can be used to identify more subtle changes to hematopoietic abnormalities. This is especially important for analysis of Myelodysplastic Syndrome ("MDS"), where abnormalities are observed in the more mature cells rather than just the immature blasts. Statistical analysis will identify bulges in the tubes or shifts in the centroid line that may denote the abnormal regulation of cells. It may also define regulatory points and rates of progression through the developmental process, enabling a better understanding of the loss of coordinated gene regulation observed during neoplastic transformation.

FIG. 1 is a functional block diagram of a system 100 implementing an embodiment of a system for detecting abnormal cells using multi-dimensional analysis. The system 100 comprises a measurement system 102 and a diagnostic system 104.

The measurement system 102 measures characteristics of cells in a sample of cells, and as illustrated comprises a flow cytometer 106 and a data formatter 108. More than one flow cytometer 106 may be employed, although usually the measurements for a particular sample would be taken with one instrument. For example, as discussed in more detail below, measurements from a normal set of cells may be taken with one flow cytometer, while measurements from a test set of cells may be taken with another flow cytometer. Other measurement devices may be employed in the measurement system 102, such as a microscope (e.g., high throughput microscopy). The measurement system 102 may contain a separate data formatter 108 to format the data collected by the measurement system 102. Alternatively, the data formatter 108 may be part of another component of the system 100, such as the flow cytometer 106 or the diagnostic system 104. The data formatter 108 may, for example, format data collected by a flow cytometer 106 into Flow Cytometry Standard FCS 2.0 format or another data file format. The measurement system 102 may comprise additional components, such as controllers, memories, discrete circuitry and hardware, and various combinations thereof.

The diagnostic system 104 analyzes data received from the measurement system 102, as discussed in more detail below. In the embodiment illustrated in FIG. 1, the diagnostic system 104 comprises a controller 110, a memory 112, a parser 114, a control input/output interface 116, a data input/output interface 118, a graphics engine 120, a statistics engine 122, a display 124, a printer 126 and a diagnostic system bus 130. The diagnostic system bus 130 may include a power bus, control bus, and status signal bus in addition to a data bus. For the sake of clarity, however, the various diagnostic system buses are illustrated in FIG. 1 as the diagnostic system bus 130.

The diagnostic system 104 may be physically remote from the measurement system 102. The measurement system 102 may be coupled to the diagnostic system 104 via one or more communication links, such as the Internet, an extranet, and/or an intranet or other local or wide area networks. Similarly, components of the diagnostic system 104 may be physically remote from one another and may be coupled together via communication links, such as the Internet, an extranet, and/or an intranet or other local or wide area networks. There may be one or more diagnostic systems each coupleable to one or more measurement systems. The communication links may be wired, wireless, or various combinations thereof.

The diagnostic system 104 may be implemented in a variety of ways, including as separate subsystems. The diagnostic system 104 may be implemented as a digital signal processor (DSP), an application-specific integrated circuit (ASIC), or the like, or as a series of instructions stored in a memory, such as the memory 112 and executed by a controller, such as the controller 110. Thus, software modifications to existing hardware may allow the implementation of the diagnostic system 104. Various subsystems, such as the parser 114 and the control input/output interface 116, are identified as separate blocks in the functional block diagram of FIG. 1 because they perform specific functions that will be described in more detail below. These subsystems may not be discrete units but may be functions of a software routine, which will probably, but not necessarily, be separately callable and hence identifiable elements. Any suitable software or combinations of software may be used to implement the diagnostic system 104, including, for example, WinList and/or Java implemented with a Java Run Time Environment or a 3-D Java Run Time Environment.

While the illustrated embodiment denotes a single controller 110, other embodiments may comprise multiple controllers. The memory 112 may comprise, for example, registers, read only memory ("ROM"), random access memory ("RAM"), flash memory and/or electronically erasable read programmable read only memory ("EEPROM"), and may provide instructions and data for use by the diagnostic system 104.

The diagnostic system 104 may comprise additional components, such as controllers, memories, discrete circuitry and hardware, and various combinations thereof.

An embodiment is described herein with respect to a study that was conducted of the B lymphoid lineage. Where appropriate, references to FIG. 1 are incorporated into the description of the study. Embodiments described herein can be applied to study, characterize and diagnose other normal and diseased lineages, such as erythroid, T lymphoid and others, including those with multiple lineages, such as the myeloid lineages (see Shulman H, 1999, supra; Wells D A, 1998, supra; and Loken M R and Wells D A, *Normal Antigen Expression in Hematopoiesis: Basis for Interpreting Leukemia Phenotypes*, in *Immunophenotyping*, Eds Carleton Stewart and Janel K. A. Nicholson, 2000, Wiley-Liss, Inc.).

The B lymphocyte lineage is a single lineage and is well defined into 4 stages of development within the bone marrow with multiple antigenic differences between stages that have been well characterized. The entire B lineage is identified by the expression of a single antigen, CD19, permitting the detection of all 4 stages of B lineage cells. The earliest B lineage cells (Stage I) are identified by the expression of CD34, high levels of CD10 and low levels of CD45. During Stage II, CD34 is lost, CD10 intensity is reduced by a factor of 2, CD45 intensity increases and CD20 begins to be expressed. Once CD20 reaches a maximum, there is a further increase in CD45 with a loss of CD10 denoting Stage III. The final stage (IV) of B lymphoid development is characterized by the absence of CD10, expression of CD22 and high levels of CD45.

As would be understood by the skilled artisan, other cell lineages that can be characterized using the methods described herein may comprise multiple lineages or branched lineages and lineages may be defined into varying numbers of stages of development. For example, the myeloid lineage includes, among others, the erythroid and the granulocyte-monocyte lineage. The granulocyte-monocyte lineage branches into the monocyte and the neutrophil lineages.

Neutrophils can be divided into five identifiable stages. Stage I myeloblasts identified by the expression of CD34 also exhibit HLA-DR, CD13, and CD33 at high levels but do not express CD11b, CD15, and CD16. These myeloblasts are intermediate in size by forward light scatter (FSC) but have low side scatter (SSC). The progression to stage II is denoted by the loss of CD34 and HLA-DR, acquisition of high levels of CD15, a dramatic increase in SSC expression, without expression of CD11b (see Loken M R and Wells D A, 2000, supra). Stage II is accompanied by a slight decrease in CD33. Stage III of neutrophil development is marked by the acquisition of intermediate levels of CD11b, loss of CD13, and a decrease in SSC related to the appearance of secondary granules. Stage IV is noted by the correlated increase in CD13 and CD16 with a further slight decrease in CD33 expression. Stage V corresponds to the mature neutrophil found in peripheral blood. This cell has maximal amounts of CD16, CD13, and CD45 with an increase in density.

The monocyte lineage has three detectable stages based on the expression of cell surface antigens. Monocytic development has two stages of maturation after the myeloblast stage (indistinguishable from stage I of neutrophil development). These cells retain HLA-DR throughout their development, in contrast to the neutrophils that rapidly lose this antigen at the promyelocyte stage. The maturation of monocytes (stage II) is first identified by the rapid appearance of CD11b while maintaining intermediate levels of CD45. Stage II of monocyte development is accompanied by increases in CD13 and CD33 expression with low expression of CD15. Stage III of development is defined by a coordinated increase in both CD45 and CD14 (see Loken M R and Wells D A, 2000, supra).

Erythroid cells have only two stages (see Loken M, 1992, supra). Commitment to this lineage is identified by the loss of CD45 and increase in CD71, stage I. The expression of glycophorin and the appearance of hemoglobin mark the second stage. The final steps of maturation of the erythroid cells are observed by the loss of the nucleus, a decrease in CD71, and subsequent loss of RNA in the reticulocytes (see Loken, M R, Shah V O, Dattilio K L, Civin C I (1987) *Flow cytometric analysis of human bone marrow. I. Normal erythroid development. Blood* 69:255-263).

As described in Loken M R and Wells D A, 2000, supra, T-lymphoid cells can be divided into four stages of development in the thymus by the pattern of reactivity of 10 antigens (CD1a, CD2, CD3, CD4, CD5, CD7, CD8, CD10, CD34, and CD45). Three stages are clearly defined by multiple antigenic differences while the fourth is distinguished by size.

Thus, as would be understood by the skilled artisan upon reading the present description, the methods described herein using the B-lymphoid lineage as an example, can be used to characterize in an n-dimensional space other cell lineages such as those described herein and known in the art. In the embodiment described herein with respect to the B lymphoid lineage, all four stages of B cell development were identified using two reagent tubes with four colors:

Tube 1: CD20 FITC, CD10 PE, CD45 PerCP and CD19 APC.

Tube 2: CD22 FITC, CD34 PE, CD45 PerCP and CD19 APC.

The redundancy of markers (CD19 and CD45) in both tubes allows for comparison of data between the different tubes. In the study, data sets were collected with 200,000 events on a FACS Calibur flow cytometer (Becton Dickinson, San Jose, Calif.). The procedures for sample preparation are standard and followed a fixed protocol. See Am. J. Clin. Path. 110:84-94, supra. List mode data from two phenotypically normal patients was collected in FCS format for analysis. Clusters identified by someone well versed in both flow cytometry and hematopathology, such as a doctor, were compared to those clusters identified by the diagnostic system 104 using clustering algorithms. Visual centers of the clusters identified by the professional were compared to those generated by the diagnostic system 104. The process is iterative, in that the user revised the identified clusters based on the results from the clustering algorithms and ran additional clustering algorithms using the revised cluster definitions.

A four-color analysis of a set of normal bone marrow B lymphoid cells in tube 1 was performed. Specimens were collected to obtain 200,000 events for analysis. The cells were placed in a tube and stained with the reagents CD20-fluorescein (FITC), CD10 phycoerythrin (PE), CD45 peridinin chlorophyll protein (PerCP), and CD19 allophycocyanin (APC). Characteristics of the exposed cells were measured using flow cytometry (see flow cytometer 106 of FIG. 1). A system, such as the system 100 illustrated in FIG. 1, measures and analyzes the sample using a combination of the data received from the measurements and input from a user, such as a professional or a technician, as discussed in more detail below.

The publicly available Flow Cytometry Standard FCS 2.0 specification may be employed to store the measured characteristics of the cells in the samples. Other data formats and data structures may be employed, for example an FCS 1.0 or FCS 3.0 format may be employed. An example data structure 200 for storing a data set is illustrated in FIG. 2. With reference to FIGS. 1 and 2, the parser 114 parsed the header section 202, text section 204, data section 206 and analysis section 208 and collected information, including a parameter name, a total number of data points and data type details. The header section 202 describes the location of the other sections in the data structure 200. The header section 202 contains offset information of starting and ending points for the text 204, data 206 and analysis 208 sections. The text section 204 contains a series of ASCII encoded keyword-value pairs that describe various aspects of the data structure 200. For example, $TOT/5000/ is a keyword-value pair indicating that the total number of events in the file is 5000 and $PAR gives Total parameter number. The data section 206 contains raw data. Such data is usually in one of three modes (list, correlated or uncorrelated) described in the text section 204, by, for example, a $MODE keyword value. The data may be written to the data section 206, for example, in one of four formats (binary, floating point, double precision floating point or ASCII) described by a $DATATYPE keyword value. One common form of data storage is list mode storage in the form of binary integers ($DATATYPE/I/ $MODE/L/). The $PnB set of keywords may specify the bit width for the storage of each parameter. The PnR set of keywords may specify the channel number range for each parameter. For example, $PnB/16/ $PnR/1024/, where n is an integer, may specify a 16-bit field for parameter n and a range for the values of parameter n from 0 to 1023, which corresponds to 10 bits. The analysis section 208 is an optional segment that, when present, may contain the results of data processing. The analysis can also be performed off-line, after the data has been collected and stored in a data structure, such as the data structure 200. In the test study, an analysis section 208 was not used. An analysis section 208, however, could be used to store information defining a centroid line and radius for a data set.

The data offsets of FCS 2.0 format are given in a properties file. An example properties file 300 is illustrated in FIG. 3. The properties file contains a header section 302, which contains information about how to read the properties file 300, a format section 304, which contains information about the format of the data structure 200, and a filter section 306, which contains information the parser 114 can use to filter data stored in the data structure 200. The parser 114 uses the information extracted from the properties file 300 to parse the loaded data structure 200. The properties file 300 can be readily modified to permit the use of various data file formats, such as various Flow Cytometry Standard formats.

The system 100 may use fluorescence intensity corresponding to CD19 as an initial gate. Thus all 200,000 cells in a 200,000-cell event list need not be assessed, only the CD19 positive cells (which include all B lineage cells) may be assessed. This enhances the statistics by increasing the number of B lineage cells to be analyzed without increasing the computational time required to distinguish the B lymphoid cells from the majority of other cells in the marrow. Without such a gate on the cells of interest, it may take computational times of 6-8 hours to identify clusters in the 200,000-cell event list. The proportion of immature B lymphoid cells (Stages I-III) averages less than 2% of all nucleated cells in a normal bone marrow. See Loken, M. R., Shah, V. O., Dattilo, K. L., Civin, C. L., *Flow Cytometry Analysis of Human Bone Marrow: II. Normal B Lymphoid Development*, Blood 70:1316 (1987). Therefore, by increasing the total counts to 200,000, and gating on the relatively infrequent CD19 positive cells, the cells of interest are analyzed while maintaining the entire data set and avoiding artifacts introduced by electronic gating for CD19 during data collection. In alternative embodiments, however, electronic gating for CD19 during data collection may be employed.

The populations of interest from an example normal data set collected as described above with respect to tube 1 are illustrated in FIGS. 4A to 9A as a series of four-color analysis displays, which were generated using WinList. The populations of interest can also be displayed in other ways, such as corresponding four-shade analysis displays, which are illustrated in FIG. 4B to 9B. FIGS. 4A to 9A and 4B to 9B are collectively referred to herein as FIGS. 4 to 9.

Figure 5A:
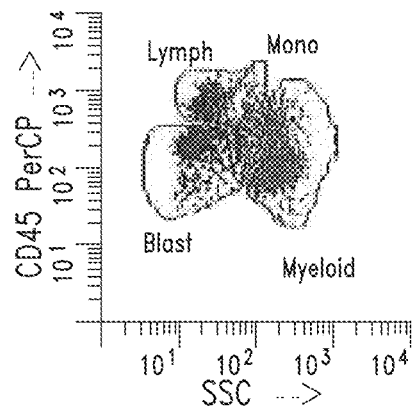
Figure 6A:
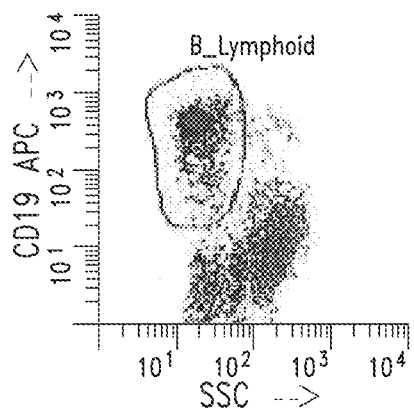
Figure 5B:
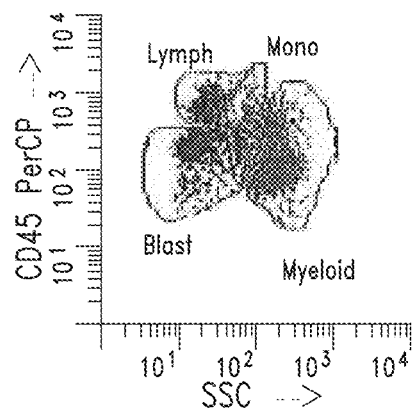
Figure 6B:
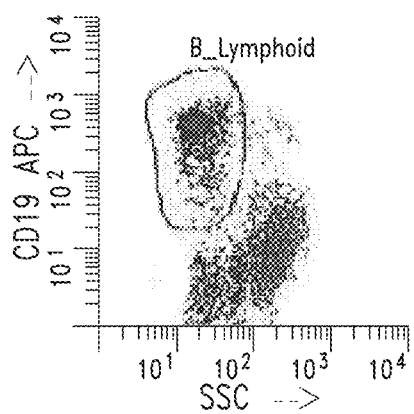

Clusters of events are initially identified in multiple 2 by 2 display projections of the 6 dimensional data (4 color and 2 light scatter parameters). The displays may be, for example, representations of the data in a Cartesian coordinate system. The display projections may be generated by the graphics engine 120 illustrated in FIG. 1. A user, such as someone well versed in both flow cytometry and hematopathology, identifies an ML region in a 2 by 2 display projection in a coordinate system with a horizontal axis corresponding to a forward light scatter and a vertical axis corresponding to side light scatter, as illustrated in FIG. 4. The ML region corresponds to nucleated cells. The user identifies lymphoid, monocyte, myeloid and blast regions in a 2 by 2 display projection in a coordinate system, such as a Cartesian coordinate system with a horizontal axis corresponding to a side light scatter and a vertical axis corresponding to a fluorescence intensity level for CD45, as illustrated in FIG. 5. The user identifies the B lymphoid cells in a 2 by 2 display projection in a coordinate system with a horizontal axis corresponding to side light scatter and a vertical axis corresponding to a fluorescence intensity level for CD19, as illustrated in FIG. 6.

Figure 7A:
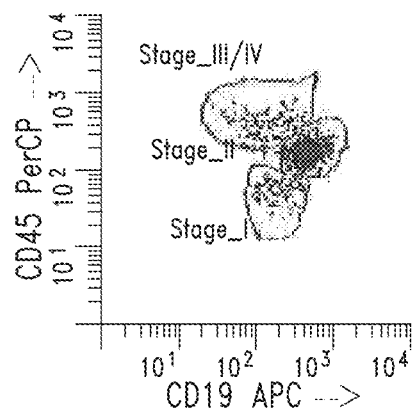
Figure 8A:
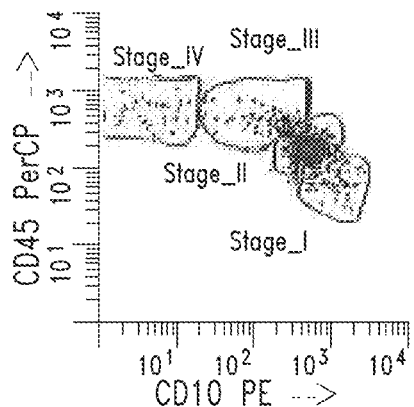
Figure 9A:
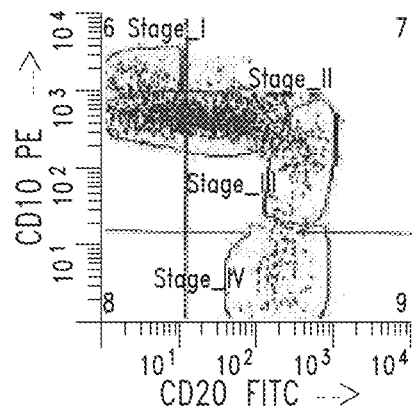
Figure 4B:
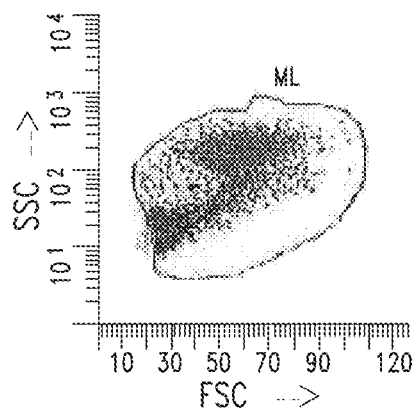
Figure 7B:
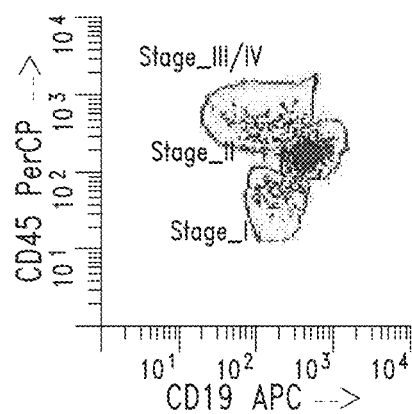
Figure 8B:
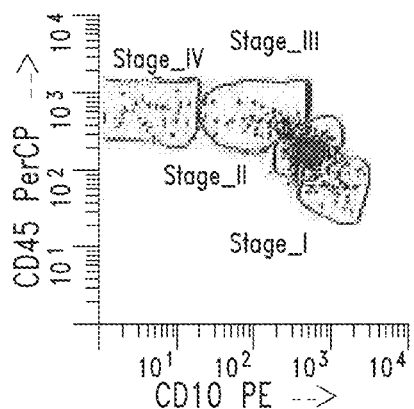
Figure 9B:
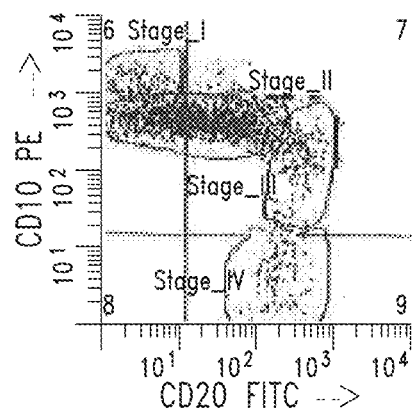

The user identifies a Stage I cluster, a Stage II cluster and a Stage III/IV cluster in a 2 by 2 display projection in a coordinate system with a horizontal axis corresponding to a fluorescence intensity level for CD19 and a vertical axis corresponding to a fluorescence intensity level for CD45, as illustrated in FIG. 7. The stages correspond to maturation levels for the B lymphoid cells. The user identifies a Stage I cluster, a Stage II cluster, a Stage III cluster and a Stage IV cluster in a 2 by 2 display projection in a coordinate system with a horizontal axis corresponding to a fluorescence intensity level for CD10 and a vertical axis corresponding to a fluorescence intensity level for CD45, as illustrated in FIG. 8. The user identifies a Stage I cluster, a Stage II cluster, a Stage III cluster and a Stage IV cluster in a 2 by 2 display projection in a coordinate system with horizontal axis corresponding to a fluorescence intensity level for CD20 and a vertical axis corresponding to a fluorescence intensity level for CD10, as illustrated in FIG. 9.

Based on the user's assessment of FIGS. 4-9, the accessed cells are assigned to an initial cluster. This results in a seven dimensional normal data set, the dimensions corresponding to: a forward light scatter; a side light scatter; a CD19 fluorescence intensity level; a CD45 fluorescence intensity level; a CD20 fluorescence intensity level; a CD10 fluorescence intensity level; and a cluster, corresponding to a stage of maturation within the B cell population. A color is assigned to each cluster identification and the data is mapped in a six dimensional space. The data is displayed by a diagnostic system, such as the diagnostic system 104 illustrated in FIG. 1, in a rotatable pseudo three-dimensional graphic display with color-coding based on cluster identification.

Figure 10A:
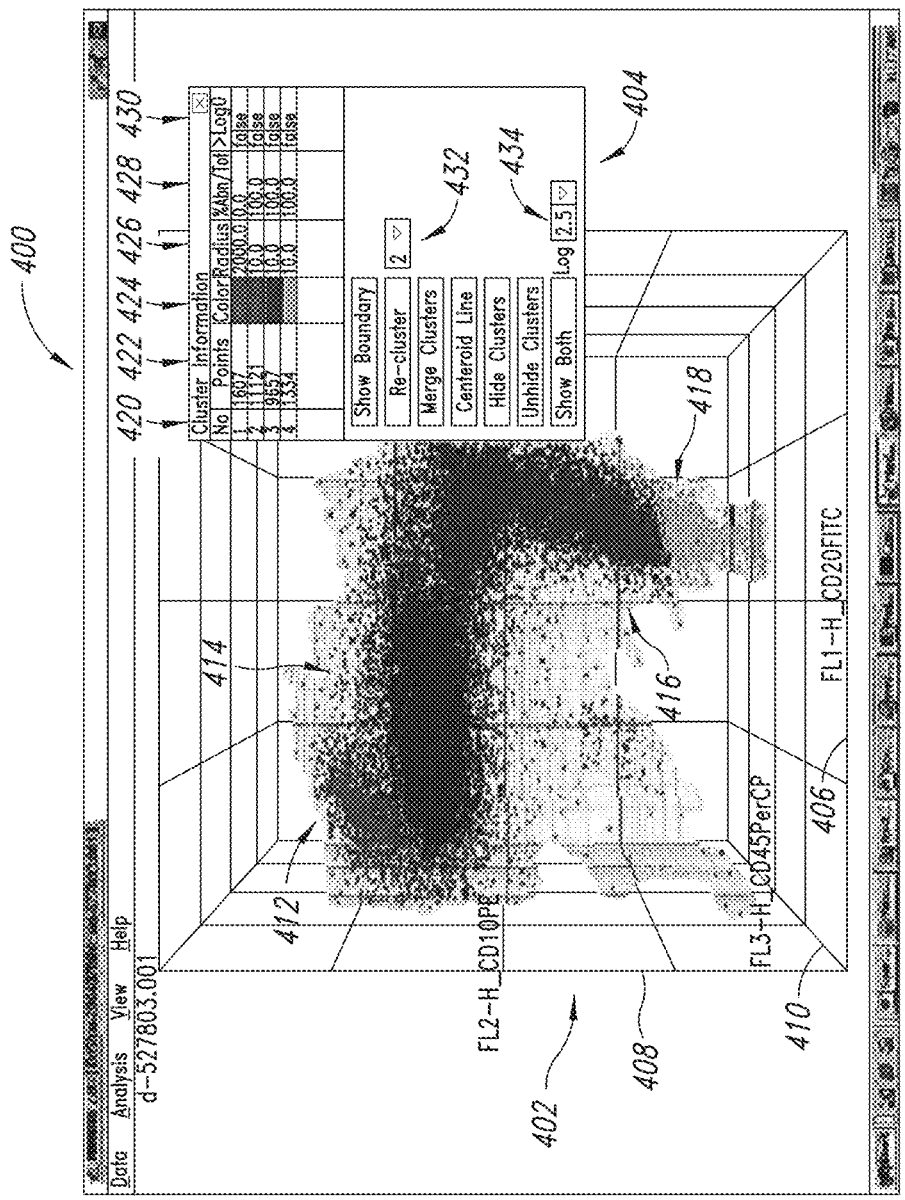
FIGS. 10A and 10B are illustrations of multi-dimensional data projected into pseudo three-dimensional displays generated by a system, such as the system illustrated in FIG. 1.
Figure 10B:
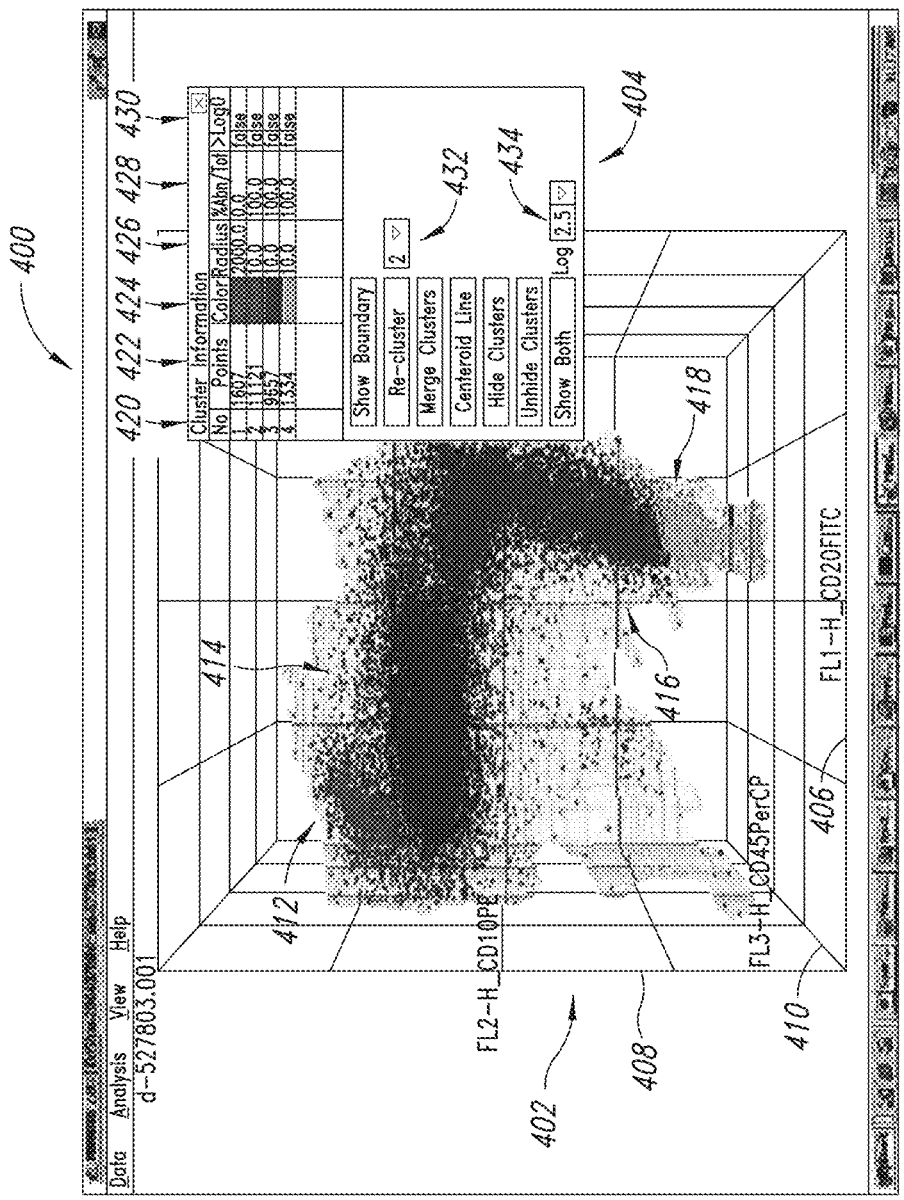

The diagnostic system 104 maps the normal data set to a three-axis coordinate system, such as a Cartesian coordinate system, and displays the data for viewing by the user. Each axis corresponds to one of the dimensions of the data set, with color indicating the cluster to which a particular cell is assigned. The data set can also be represented in a tabular display or in a combined display. FIGS. 10A and 10B (collectively FIG. 10) illustrate example displays 400 combining a pseudo 3-dimensional graphic representation 402 with a tabular representation 404. FIG. 10A is a color display and FIG. 10B is a corresponding shaded display.

The graphic representation 402 comprises an x-axis 406 corresponding to a fluorescence intensity for CD20, a y-axis 408 corresponding to a fluorescence intensity for CD10, and a z-axis 410 corresponding to a fluorescence intensity for CD45. Data in a first cluster 412 is assigned the color red and corresponds to a Stage I maturation level. Data in a second cluster 414 is assigned the color green and corresponds to a Stage II maturation level. Data in a third cluster 416 is assigned the color blue and corresponds to a Stage III maturation level. Data in a fourth cluster 418 is assigned the color yellow and corresponds to a Stage IV maturation level.

The tabular representation 404 comprises a first column 420 indicating a cluster number, a second column 422 indicating a number of points in the cluster, a third column 424 indicating the color or shade assigned to the cluster, a fourth column 426 indicating a radius of the cluster, a sixth column 428 indicating a percentage of abnormal events or points in the total set of events or points and a seventh column 430 indicating whether a logarithmic distance between the centroid point for a cluster and a statistical centroid point for the cluster is greater than a threshold value. The display 400 as illustrated may be an interactive computer display. The user can update information used to generate the display 400 using data entry fields 432, 434. As illustrated the threshold value is set at 2.5 in field 434.

Figure 11A:
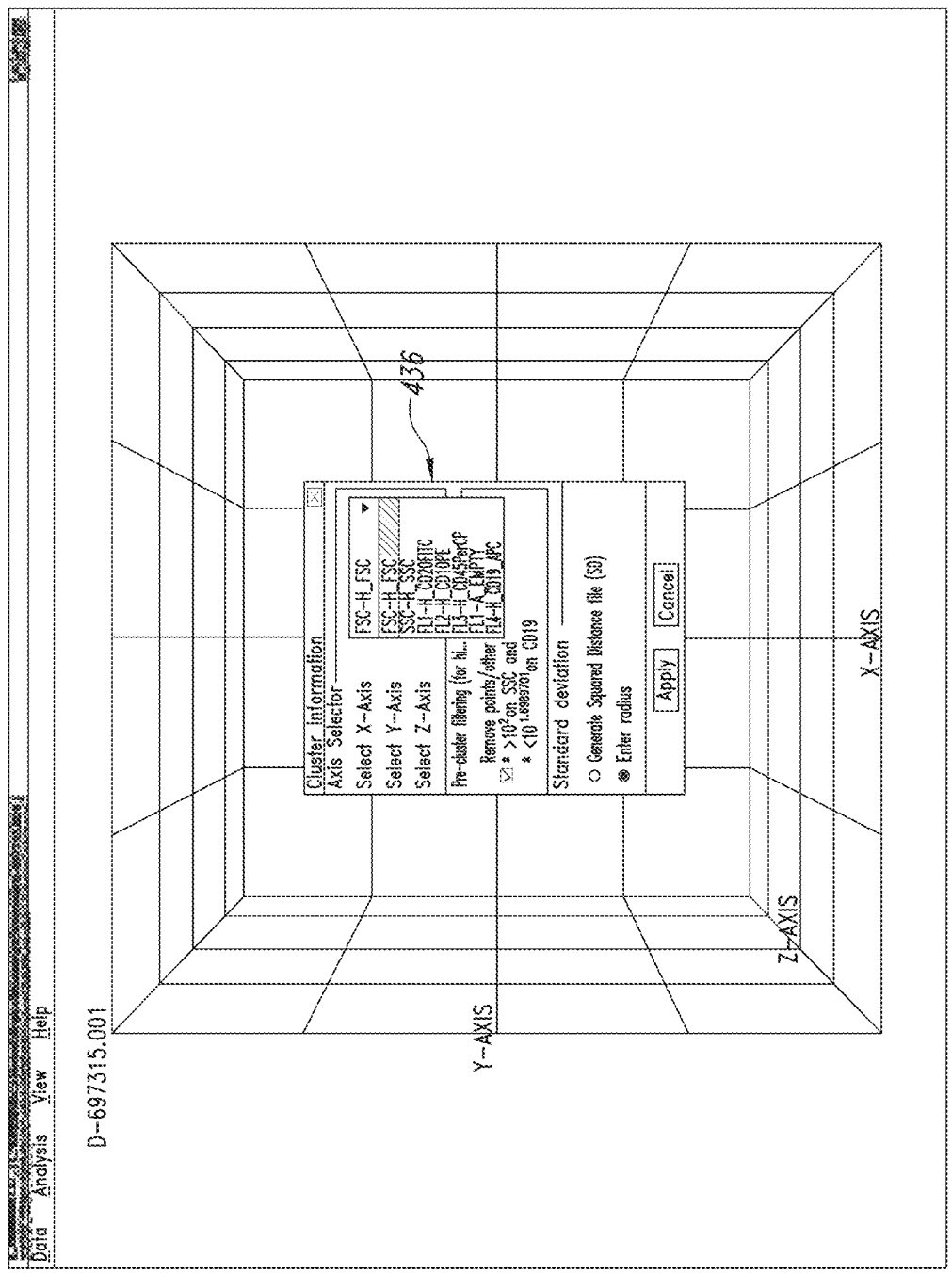
FIGS. 11A and 11B illustrate a menu of a graphical user interface generated by a system, such as the system illustrated in FIG. 1.
Figure 11B:
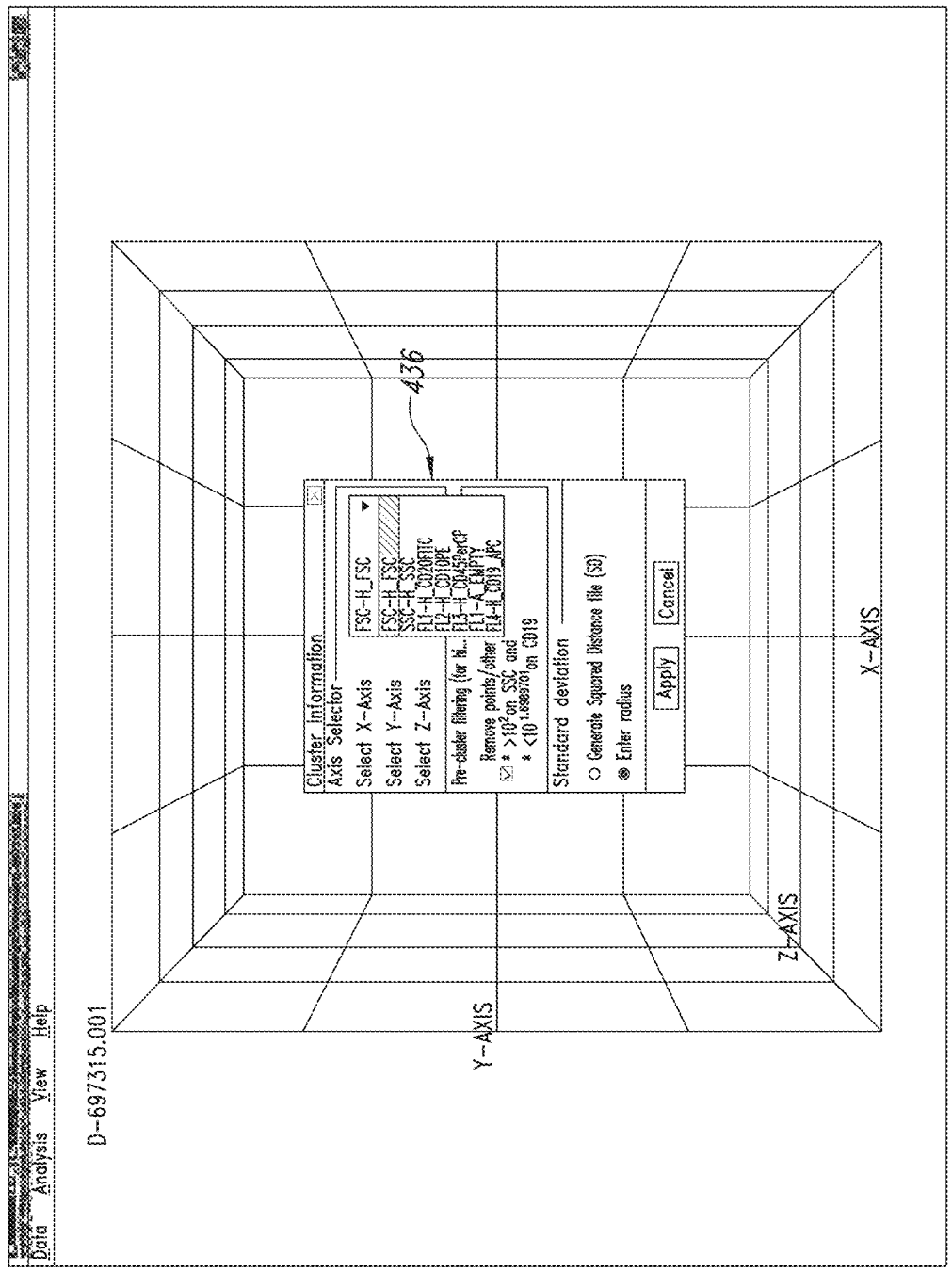

The diagnostic system 104 permits user selection of the three axes to which to map the data using a menu of a graphical user interface (GUI). FIGS. 11A and 11B illustrate an example menu 436 that can be employed by a diagnostic system, such as the diagnostic system 104 illustrated in FIG. 1. The diagnostic system 104 also permits user selection of other settings through menus. For example, menu selections may be included for: selecting between different stored filtering parameters, editing stored filtering parameters; and specifying new filtering parameter. For example, high-resolution data may be filtered to exclude data with a side scatter parameter corresponding to more that $10^2$ and a CD19 parameter corresponding to less than 10 to the 1.6989701. Menu selections also permit selection of a plane in the coordinate system on which to filter. Multiple filter criteria may be employed and the filter criteria can be greater than or less than specified thresholds. The menu system also allows selection of a specific cluster on which to apply various filter criteria. This allows the user to view various pseudo three-dimensional displays of the normal data set to assist the user in selecting initial data for use by the diagnostic system 104 in defining a centroid line and radius for the normal data set. The diagnostic system 104 also permits menu selection of a standard deviation method or fixed value and rotation of a displayed image. The diagnostic system 104 may also display cluster boundaries for a data set based on a selected centroid and radius.

The normal data set may also comprise separate data files corresponding to separate samples. For example, the user can examine and manipulate a data set comprising cells drawn from a single individual and a single tube, or the user can combine samples drawn from a plurality of individuals and/or tubes into a single normal data set. If a sample drawn from an individual is deemed to be abnormal, the sample can be excluded from the normal set of data.

Referring to the study, in the example B lymphoid data set from tube 1, the value n is equal to six. Each n-dimensional point is mapped to the n-dimensional space, which can be represented in a float array by n+1 float parameters. Table 1 illustrates the float array for an example six dimensional B lymphoid data set, where $P_1PR_1$ is the value of the first parameter for the first point, $P_2PR_1$ is the value of the first parameter for the second point, ... $P_nPR_1$ is the value of the first parameter for the nth point, etc., with a seventh parameter added for a cluster to which a point is assigned, $P_nC\#$. The float array can be generalized for any number of dimensions. The diagnostic system 104 performs one or more selected clustering algorithms on the normal data set in n-dimensional space, refining the assignment of the points to a cluster.

TABLE 1

Float Array for Six Dimensional Data Set

| $P_1PR_1$ | $P_1PR_2$ | $P_1PR_3$ | $P_1PR_4$ | $P_1PR_5$ | $P_1PR_6$ | $P_1C\#$ |
|---|---|---|---|---|---|---|
| $P_2PR_1$ | $P_2PR_2$ | $P_2PR_3$ | $P_2PR_4$ | $P_2PR_5$ | $P_2PR_6$ | $P_2C\#$ |
| $P_3PR_1$ | $P_3PR_2$ | $P_3PR_3$ | $P_3PR_4$ | $P_3PR_5$ | $P_3PR_6$ | $P_3C\#$ |
| ... | ... | ... | ... | ... | ... | ... |
| $P_nPR_1$ | $P_nPR_2$ | $P_nPR_3$ | $P_nPR_4$ | $P_nPR_5$ | $P_nPR_6$ | $P_nC\#$ |

The diagnostic system 104 allows the user to cluster the data using a selected clustering algorithm. For example, the user can specify a number of clusters, k, and use a K-means algorithm to cluster the data. For example, the diagnostic system 104 may divide the data into k clusters and assign a center to each cluster. The center can be assigned randomly to one of the points or entered based on observations by the user. The distance between two points in the n-dimensional space may be defined as follows:

$$D(P_1,P_2)=SQRT[(K_1(P_1PR_1-P_2PR_1))^2+ (K_2(P_1PR_2-P_2PR_2))^2+(K_3(P_1PR_3-P_2PR_3))^2+ \ldots +(K_n(P_1PR_n-P_2PR_n))^2]$$

Equation 1 where $D(P_1, P_2)$ is the distance between two points in the n-dimensional space and $P_1PR_1$ is the value of the first parameter for the first point, $P_2PR_1$ is the value of the first parameter for the second point, ... $P_nPR_1$ is the value of the first parameter for the nth point, etc., and $K_1, K_2, K_3, \ldots K_n$ are weighting constants. In the study, the weighting constants were set equal to one. In other words, there was no weighting employed in the study. The centers may be iteratively updated until a convergence criteria is satisfied. In each iteration, each data point is assigned to its closest center, and the centers are recalculated using the mean parameter values of all points belonging to a cluster. Typical convergence criteria used in the study were no (or minimal) reassignment of points to new cluster centers. See Forgy, E, *Cluster Analysis of Multivariate Data: Efficiency vs. Interpretability of Classifications*, Biometrics, 21:768 (1965), for a discussion of k-means clustering.

Another example clustering algorithm is a DBSCAN clustering algorithm. A neighborhood radius, $E_{ps}$, and a threshold number of points in the neighborhood, minPts, are defined and the diagnostic system 104 employs a DBSCAN clustering algorithm. The neighborhood radius and threshold number of points are defined by the user. Density-based Clustering is based on the fact that clusters are of higher density than their surroundings. DBSCAN finds dense clusters automatically for a given density threshold. See Ester, M., Kriegel, H., Sander, J., Xu, X., *A Density-Based Algorithm for Discovering Clusters in Large Spatial Databases with Noise*, In Proceedings of 2d International Conference on KDD (1996), for a discussion of DBSCAN clustering. By definition the density threshold is specified by two parameters: neighborhood radius ($E_{ps}$) and threshold number of points in ∈-neighborhood (minPts). A point 'p' is directly density-reachable from a point 'q', if 'p' is in the ∈-neighborhood of 'q'. A point 'p' is density reachable from 'q', if there is a chain of points 'p$_1$' where i=1 ... n and 'p$_{i+1}$' is directly density-reachable from 'p$_i$', 'q' is 'p$_1$' and 'p' is A point 'p' is density-connected to another point 'q', if there is a point 'o' such that both 'p' and 'q' are density-reachable from 'o'. In the study, the diagnostic system 104 started by bringing in a point to a temporary storage (tempStore, e.g. list) and finding its ∈-neighborhood. If the ∈-neighborhood of a data point contained less than 'minPts' points then it was marked as noise and another point was brought into tempStore. Otherwise, all ∈-neighborhood points were brought into tempStore. The whole process was repeated until all points were considered. In short, DBSCAN clustering groups density-connected points together as a dense cluster and removes points that are not density-connected as noise.

The diagnostic system 104 may also employ, for example, bridge clustering to cluster the data. Bridge clustering combines K-means clustering with DBSCAN clustering. See Dash, M., Liu, H., Xu, X., '1+1>2': *Merging Distance and Density Based Clustering*, Proceedings of the IEEE 7th International Conference on Database Systems for Advanced Applications (DASFAA '01), Apr. 18-21, 2001, Hong Kong, China, for a discussion of bridge-clustering. K-means was performed first followed by density-based clustering over each k-means cluster, and at the end, k-means clusters were refined by removing the noise found in density-based clustering. For effective merging, each data point has the following three columns to store results of clustering: <k-means_ID>, <DBSCAN_ID> and <core/∈-core/non/core>, where:

K-means_ID is the cluster assigned to each point when k-means is run on the data points;

DBSCAN_ID is the cluster assigned to each point when DBSCAN is run on each k-means cluster; and core/E-core/non-core values are assigned based on the following definitions:

Definition 1 (CoreDistance): For each cluster, CoreDistance is half of the distance between its center and its closest cluster center.

Definition 2 (CorePoint): It is not farther from its cluster center by 'CoreDistance–∈'. Core region of a cluster is that inside which each data point is core.

Definition 3 (+∈ CorePoint): Its distance from cluster center is between 'CoreDistance' and 'CoreDistance+∈'.

Definition 4 (–∈ CorePoint): Its distance from cluster center is between 'CoreDistance' and 'CoreDistance∈∈'. For convenience, when +∈ and –∈ core points are considered, together they are denoted as E-core. ∈-core region is that in which each point is E-core.

Definition 5 (Non-core point): It is neither a core nor an E-core point. Non-core region is that in which each point is non-core.

The diagnostic system 104 can also employ wavelet clustering. Wavelet transforms are a special form of Fourier Transforms. See Press, W. H., Flannery, B. P., Teukiosky, S. A., *Numerical Recipes In C: The Art of Scientific Computing*, Ch. 13.10, Cambridge University Press (1992). This technique has been well established in the image processing and data mining areas for pattern and edge recognition. See Sheikholeslami, G., Chatterjee, S., Zhang, A., *WaveCluster: A Multi-Resolution Clustering Approach for Very Large Spatial Databases*, Proceedings of the 24th VLDB Conference, New York, USA, 1998. For example, the standard Daubechies wavelet filtering and the N-Dimensional Discrete Wavelet Transform (NDDFT) may be employed.

Figure 12A:
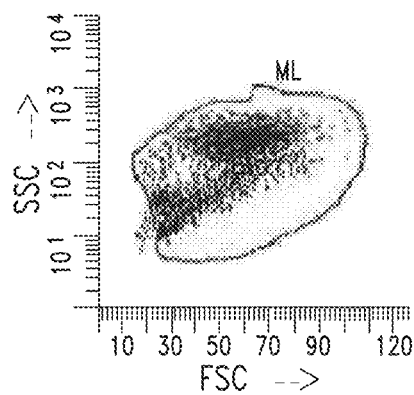
Figure 13A:
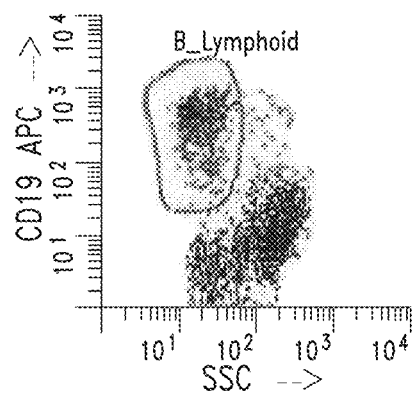
Figure 12B:
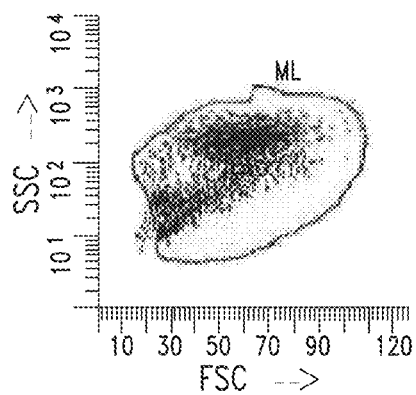
Figure 13B:
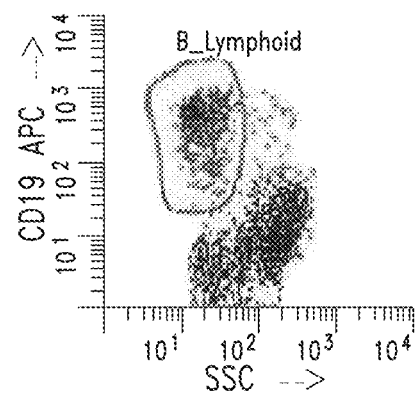

In a similar manner, the same populations (Stages) in a second normal data set are identified in the second tube (CD22, CD34, CD45, CD19), as illustrated in color in FIGS. 12A to 17A and in shading in FIGS. 12B to 17B (collectively referred to herein as FIGS. 12 to 17). The user identifies an ML region in a 2 by 2 display projection in a coordinate system with a horizontal axis corresponding to a forward light scatter and a vertical axis corresponding to side light scatter, as illustrated in FIG. 12. The ML region corresponds to nucleated cells. The user identifies B-lymphoid cells in a 2 by 2 display projection in a coordinate system with a horizontal axis corresponding to side light scatter and a vertical axis corresponding to a fluorescence intensity level for CD19, as illustrated in FIG. 13.

Figure 14A:
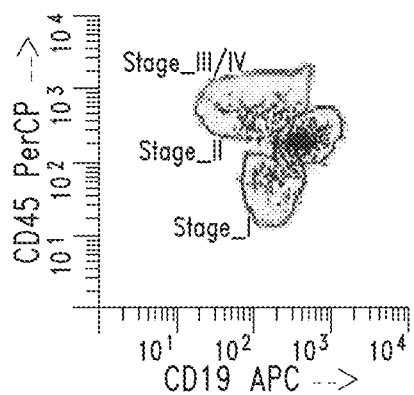
Figure 15A:
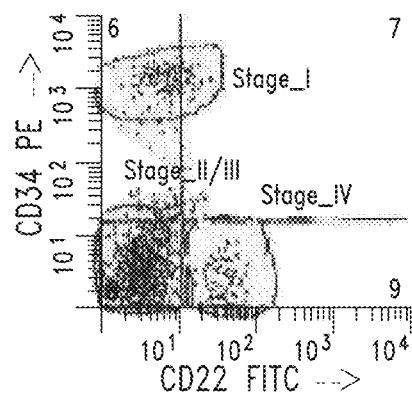
Figure 16A:
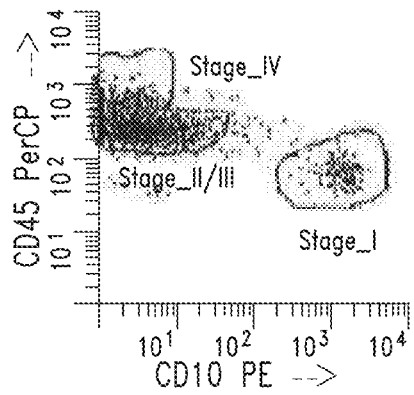
Figure 17A:
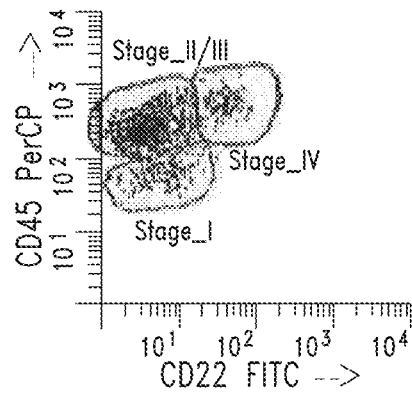
Figure 14B:
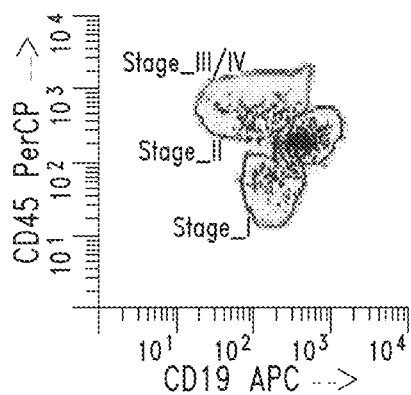
Figure 15B:
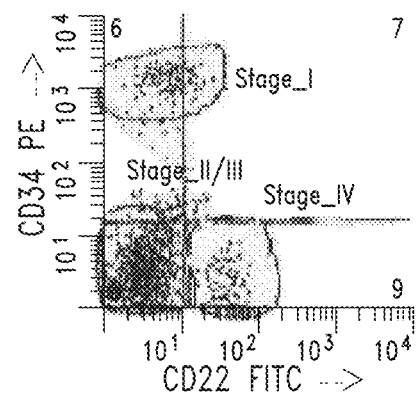
Figure 16B:
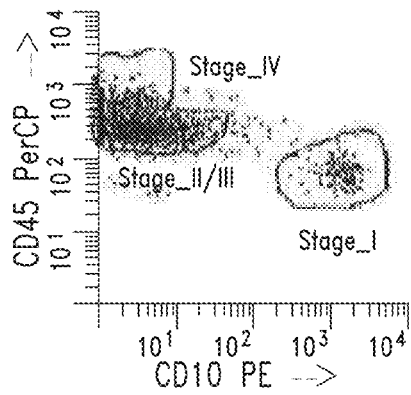
Figure 17B:
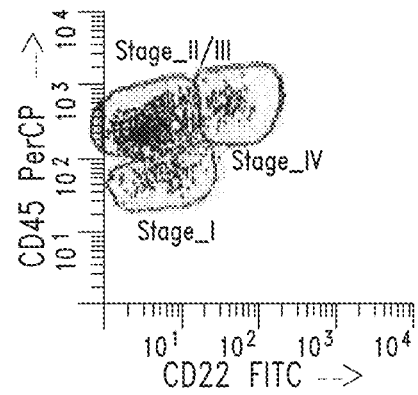

The user identifies a Stage I cluster, a Stage II cluster and a Stage III/IV cluster in a 2 by 2 display projection in a coordinate system with a horizontal axis corresponding to a fluorescence intensity level for CD19 and a vertical axis corresponding to a fluorescence intensity level for CD45, as illustrated in FIG. 14. The stages correspond to maturation levels for the B lymphoid cells. The user identifies a Stage I cluster, a Stage II/III cluster and a Stage IV cluster in a 2 by 2 display projection in a coordinate system with a horizontal axis corresponding to a fluorescence intensity level for CD22 and a vertical axis corresponding to a fluorescence intensity level for CD34, as illustrated in FIG. 15. The user identifies a Stage I cluster, a Stage II/III cluster and a Stage IV cluster in a 2 by 2 display projection in a coordinate system with horizontal axis corresponding to a fluorescence intensity level for CD34 and a vertical axis corresponding to a fluorescence intensity level for CD45, as illustrated in FIG. 16. The user identifies a Stage I cluster, a Stage II/III cluster and a Stage IV cluster in a 2 by 2 display projection in a coordinate system with a horizontal axis corresponding to a fluorescence intensity for CD22 and a vertical axis corresponding to a fluorescence intensity for CD45, as illustrated in FIG. 17. The results from Tube 1 and Tube 2 are combined to produce a single normal data set, as described in more detail below.

Figure 18A:
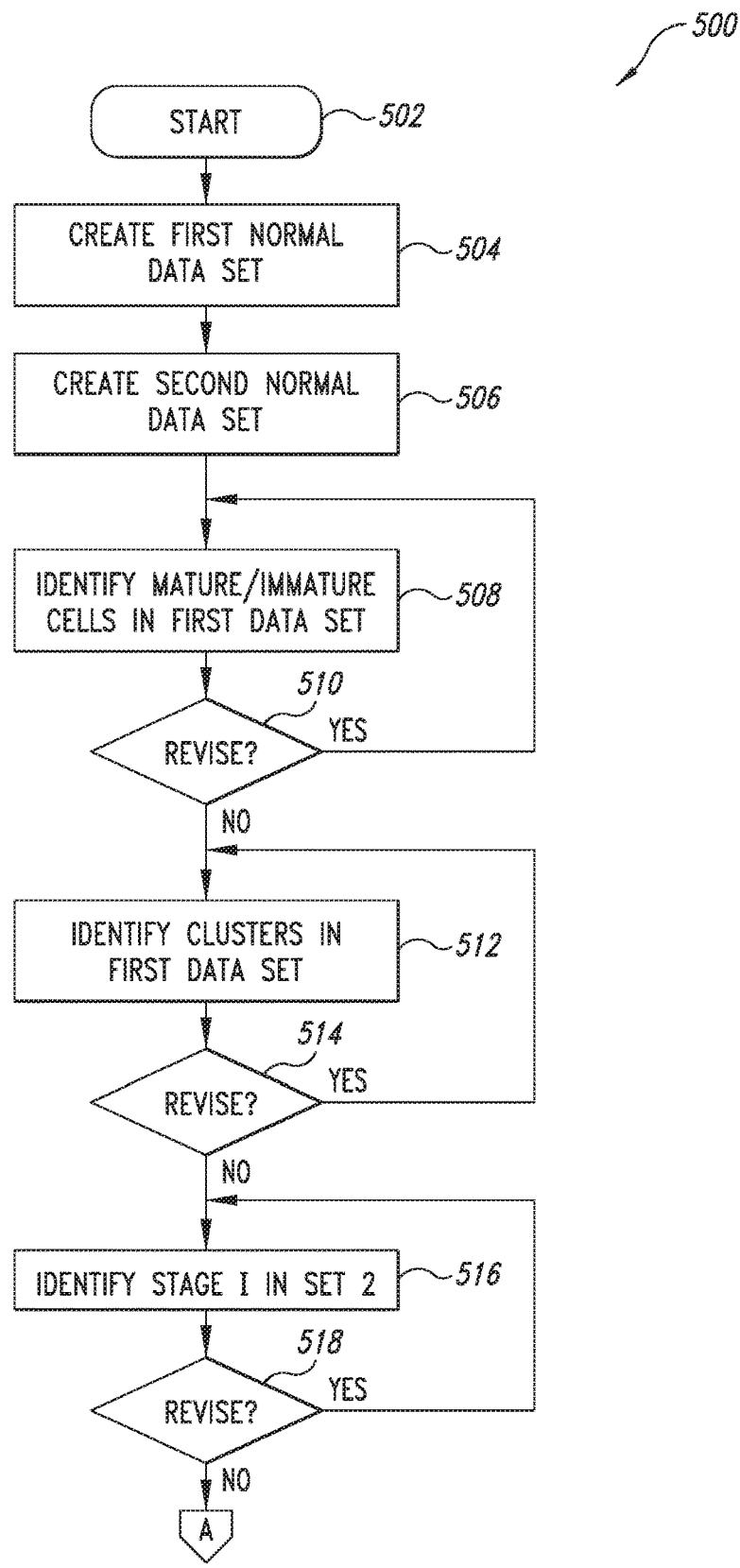
FIGS. 18A to 18C are a flow chart illustrating operation of a system to define a normal centroid and radius for a set of normal clusters corresponding to a normal cell lineage.
Figure 18B:
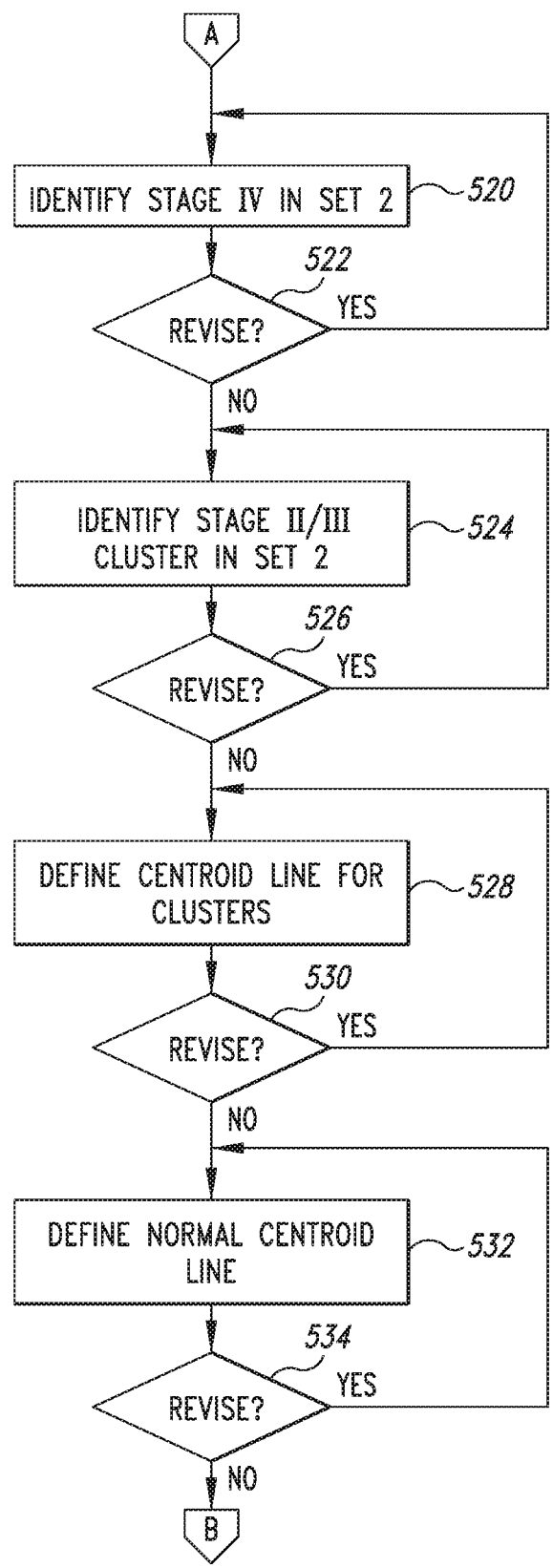
Figure 18C:
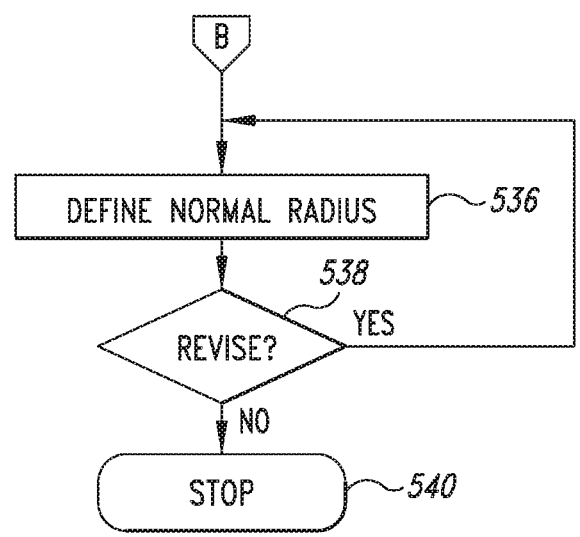

Once the clusters are identified and refined by the user selectively using the clustering software, a centroid line and radius are defined for the normal clusters, where each cluster corresponds to a cell maturation level within a cell lineage. FIGS. 18A to 18C illustrate an embodiment of a subroutine 500 that can be employed to define a normal population of cells, discussed with respect to the system 100 illustrated in FIG. 1 and the B lymphoid cells collected in tubes 1 and 2 as discussed above. The entire process of defining a normal population of cells should be viewed as an iterative one. Other cell lineages, such as a myeloid lineage, may comprise multiple lineages or branched lineages. In such cases, the multiple centroid lines may be defined or a defined centroid line may have branches.

The subroutine 500 starts at 502 and proceeds to 504. At 504, the system 100 filters a data set gathered by measuring characteristics of the cells in tube 1 by gating on CD19 positive cells, creating a first normal data set, and proceeds to 506. At 506, the system 100 filters a data set gathered by measuring characteristics of the cells in tube 2 by gating on CD19 positive cells, creating a second normal data set, and proceeds to 508.

At 508, the system 100 distinguishes between mature and immature cells in the first data set. This can be done by, for example, plotting fluorescence intensities for CD45 against fluorescence intensities for CD19 and clustering the first data set based on input from the user together with automated clustering techniques. The system proceeds to 510, where it determines whether to revise the distinction between the mature and immature cells in the first data set. This decision may be based on the results of automated clustering techniques, statistical analysis of the data, and/or displays of the data set generated based on the distinction, and may be automated and/or based on input from the user. If the system 100 determines the distinction should be revised, the system 100 returns to 508. If the system 100 determines the distinction should not be revised, the system proceeds to 512.

At 512, the system 100 identifies clusters representing Stages I, II, III and IV in the first data set. This can be done by, for example, plotting fluorescence intensities for CD45 against fluorescence intensities for CD10 and CD20 and clustering the data based on input from the user together with automated clustering techniques. The system 100 proceeds to 514, where it determines whether to revise the identification of the clusters in the first data set. This decision may be based on the results of the automated clustering techniques, statistical analysis of the data, and/or displays of the data set generated based on the identification, and may be automated and/or based on input from the user. If the system 100 determines the identification should be revised, the system 100 returns to 512. If the system 100 determines the identification should be accepted, the system proceeds to 516.

At 516, the system 100 identifies a cluster representing Stage I in the second data set. This can be done by, for example, plotting fluorescence intensities for CD34 against fluorescence intensities for CD45 and clustering the data based on input from the user together with automated clustering techniques. The system proceeds to 518, where it determines whether to revise the identification of the Stage I cluster in the second data set. This decision may be based on the results of the automated clustering techniques, statistical analysis of the data, and/or displays of the data set generated based on the identification, and may be automated and/or based on input from the user. If the system 100 determines the identification should be revised, the system 100 returns to 516. If the system 100 determines the identification should be accepted, the system proceeds to 520.

At 520, the system 100 identifies a cluster representing Stage IV in the second data set. This can be done by, for example, plotting fluorescence intensities for CD22 against fluorescence intensities for CD34 and clustering the data based on input from the user together with automated clustering techniques. The system proceeds to 522, where it determines whether to revise the identification of the Stage IV cluster in the second data set. This decision may be based on the results of the automated clustering techniques, statistical analysis of the data, and/or displays of the data set generated based on the identification, and may be automated and/or based on input from the user. If the system 100 determines the identification should be revised, the system 100 returns to 520. If the system 100 determines the identification should be accepted, the system proceeds to 524.

At 524, the system 100 identifies a cluster representing Stages II and III in the second data set. This can be done by, for example, plotting fluorescence intensities for CD34 against fluorescence intensities for CD45 based on input from the user together with automated clustering techniques. The system proceeds to 526, where it determines whether to revise the identification of the Stage II/III cluster in the second data set. This decision may be based on the results of the automated clustering techniques, statistical analysis of the data, and/or displays of the data set generated based on the identification, and may be automated and/or based on input from the user. If the system 100 determines the identification should be revised, the system 100 returns to 524. If the system 100 determines the identification should be accepted, the system proceeds to 528.

At 528, the system 100 defines a centroid line for each cluster identified at acts 512, 516, 520 and 524. A centroid line for a cluster may be fractal and may be determined based on input from the user together with automated clustering techniques. A centroid line for a cluster may be defined by, for example, combining the geometric mean in n-dimensional space with the centroid point determined by the clustering algorithms. The system proceeds to 530, where it determines whether to revise the defined centroid lines for the identified clusters. This decision may be based on the results of automated clustering techniques, statistical analysis of the data, and/or displays of the data set generated based on the identification, and may be automated and/or based on input from the user. If the system 100 determines the identification should be revised, the system 100 returns to 528. If the system 100 determines the identification should be accepted, the system proceeds to 532.

At 532, the system 100 defines a normal centroid line corresponding to a normal maturational lineage based on the combined data sets. This may be done by, for example, joining the defined centroid lines of the identified clusters using geometric bending. The system 100 also may combine input from the user with automated clustering techniques to define the normal centroid line. The distance along this centroid line as compared to the beginning and end is a measure of maturation of those cells for a given lineage as assessed by the specific combination of monoclonal reagents. It should be noted that different antibody combinations may be used to expand certain parts of the maturational process, while other combinations focus on other maturational stages or other lineages.

The system proceeds to 534, where it determines whether to revise the definition of the normal centroid line. This decision may be based on the results of automated clustering techniques, statistical analysis of the data, and/or displays of the data set generated based on the identification, and may be automated and/or based on input from the user. If the system 100 determines the definition should be revised, the system 100 returns to 532. If the system 100 determines the definition should be accepted, the system proceeds to 536.

At 536, the system 100 defines a boundary, or normal radius, around the defined normal centroid line. The normal radius, or boundary, may be a fixed radius, or it may vary. For example, it may be a fixed distance, such as 10, or it may be a function of a position on the defined normal centroid line or in the n-dimensional space. One definition may be employed for a first portion of the defined normal centroid line and a second definition may be employed for other portions of the defined normal centroid line. The normal radius may be determined using statistical algorithms, such as wavelet clustering techniques and/or K-means edge envelope techniques (using density of clusters) and/or be based on input from the user. Smoothing algorithms for defining specific 3-dimensional patterns may also be employed and compared against observations for a statistically determined number of files.

The system 100 proceeds to 538, where it determines whether to revise the defined normal radius. This decision may be based on the results of automated clustering techniques, statistical analysis of the data, and/or displays of the data set generated based on the identification, and may be automated and/or based on input from the user. If the system 100 determines the definition should be revised, the system 100 returns to 536. If the system 100 determines the definition should be accepted, the system proceeds to 540, where the subroutine 500 stops.

In some embodiments a system 100 may perform other acts not shown in FIGS. 18A to 18C, may not perform all of the acts shown in FIGS. 18A to 18C, or may perform the acts of FIGS. 18A to 18C in a different order. For example, the subroutine may be made more iterative. For example, the subroutine 500 may be modified so that the system 100 determines after act 538 whether to revise the defined normal centroid line, and if so, returns to 532. The subroutine 500 may also call other subroutines to perform various functions, such as the subroutine 600 described below with respect to FIG. 19. The subroutine 500 may also return the value of any desired variables, such as data entered by a user.

Figure 19:
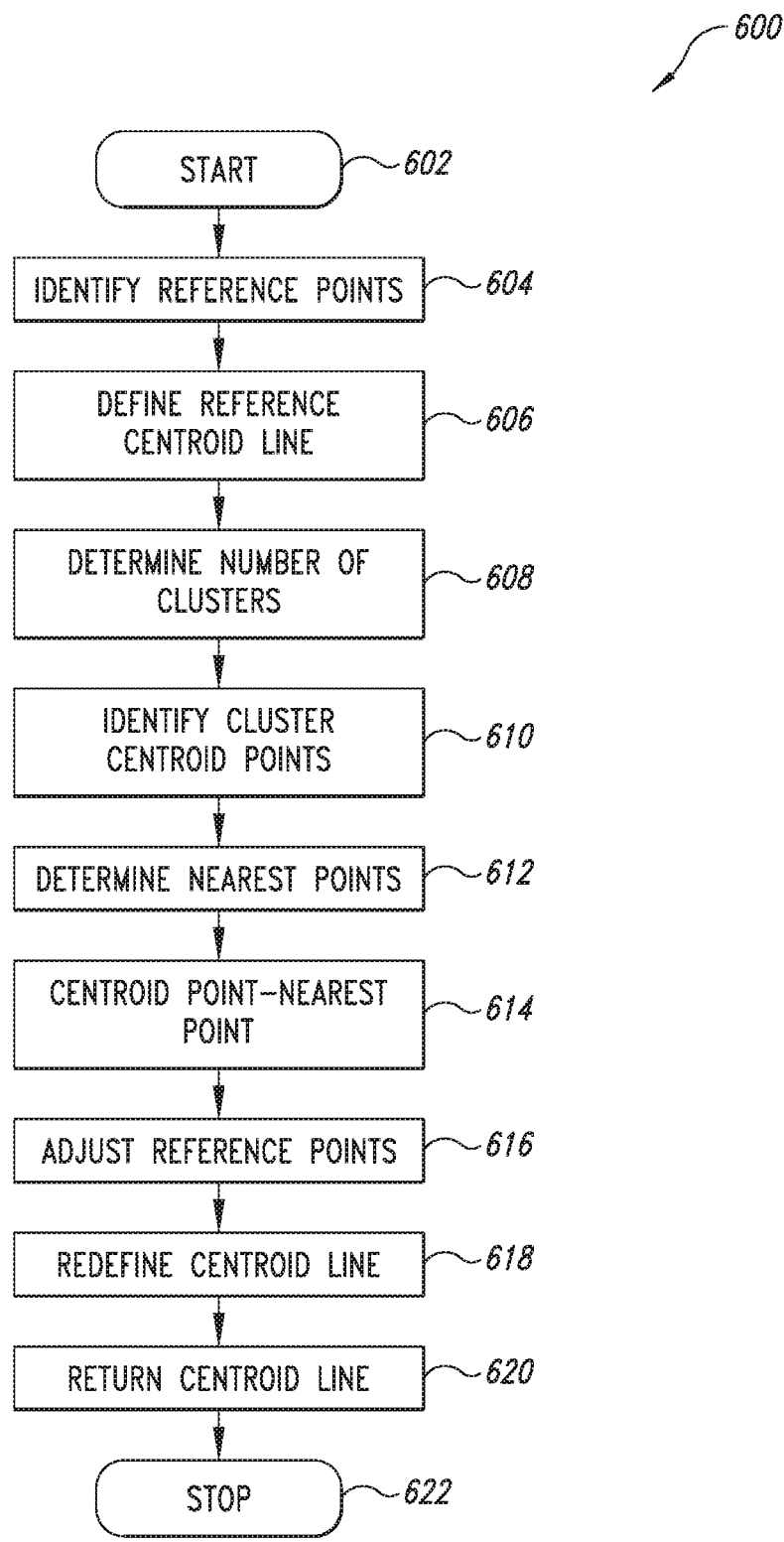
FIG. 19 is a flow chart illustrating operation of a system to define a centroid line for a set of normal clusters corresponding to a normal cell lineage.
Figure 20A:
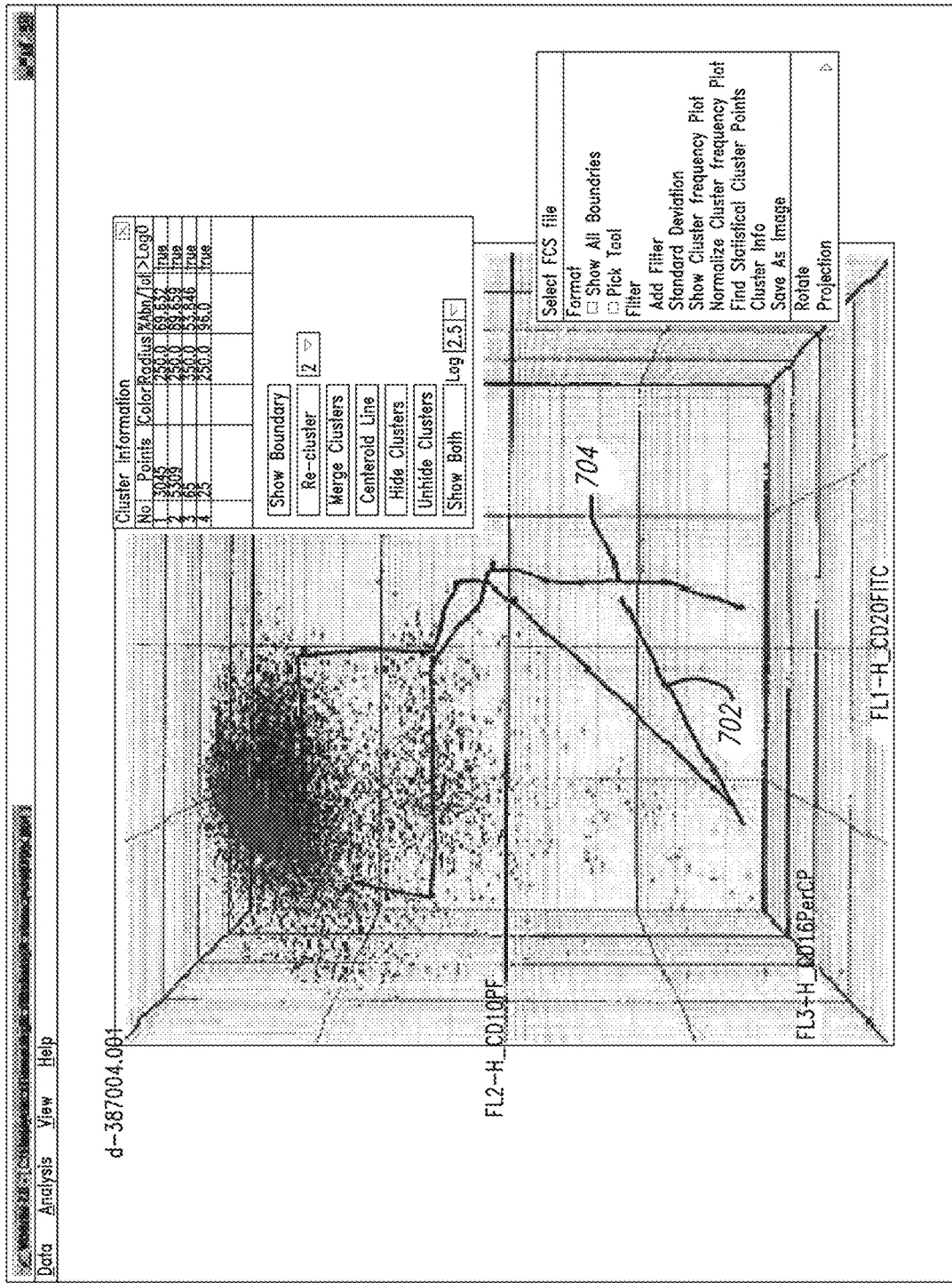
FIGS. 20A and 20B are illustrations of multi-dimensional data projected into pseudo three-dimensional displays generated by a system, such as the system illustrated in FIG. 1.
Figure 20B:
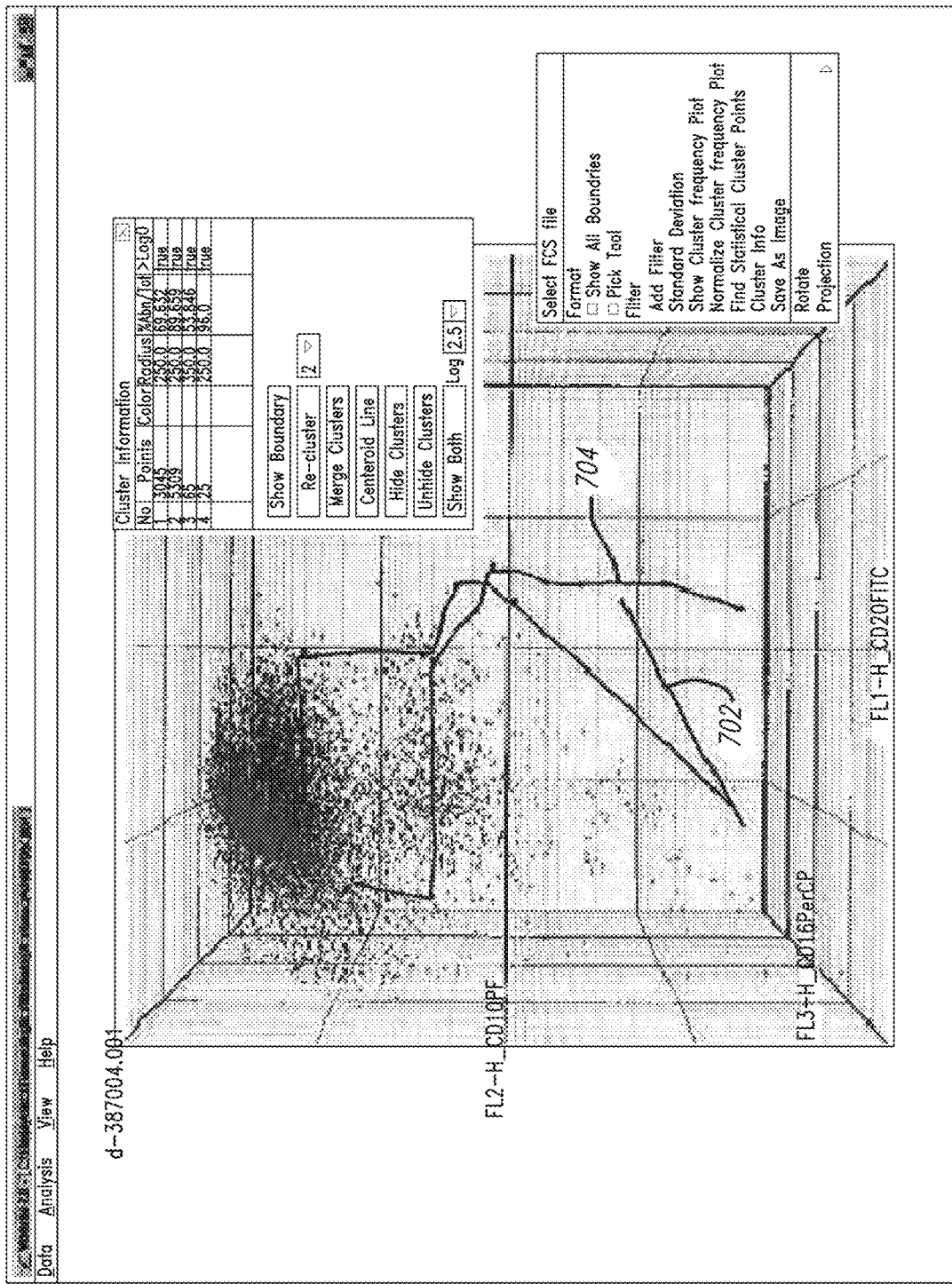

FIG. 19 is a flow diagram for an example subroutine 600 that may be employed by a diagnostic system, such as the diagnostic system 104 illustrated in FIG. 1, to define a normal centroid line for a set of clusters. FIGS. 20A and 20B (collectively FIG. 20) illustrate graphic representations of the data, an initial reference centroid line 702 and a calculated normal centroid line 704 from the study.

The subroutine 600 starts at 602 and proceeds to 604. At 604, the diagnostic system 104 identifies a set of reference points. For example, the diagnostic system 104 may identify ten reference points selected by a user after viewing various representations of the data set. Alternatively, the diagnostic system 104 may identify a number of statistically selected reference points or may combine input from a user with statistical analysis. In the study, the user selected ten reference points after viewing various representations of the data.

The diagnostic system 104 proceeds to 606, where it defines a reference centroid line based on the identified set of reference points. FIG. 20 illustrates an example initial reference centroid line 702 defined based on the ten reference points identified by the user in the study.

The diagnostic system 104 proceeds to 608, where it determines the number of clusters in which to group the data. For example, in the study the diagnostic system 104 grouped the data into four clusters based on input from the user. Alternatively, the number of clusters could be determined statistically (by using, for example, dbscan clustering) or by using input from a user in combination with statistical analysis.

The diagnostic system 104 proceeds to 610, where it identifies centroid points for the corresponding number of clusters. This can be done by assigning each point to a cluster based on user input or statistical algorithms or on a combination thereof. See the discussion of clustering algorithms above. The respective parameter values for all the points assigned to a cluster are added together then the result is divided by the number of points in the cluster to obtain the parameter value for the centroid point. For example, if the diagnostic system 104 determined at act 608 to group the data into four clusters, the diagnostic system 104 would identify four centroid points, each point corresponding to a cluster. Table 2, produced below, illustrates an example calculation of a centroid point for a cluster containing 5 data points in a 3 dimensional space.

TABLE 2

Example Calculation of Centroid Points

|  | X-parameter | Y-parameter | Z-parameter |
| --- | --- | --- | --- |
| Point 1 | 25 | 30 | 400 |
| Point 2 | 30 | 35 | 390 |
| Point 3 | 25 | 35 | 395 |
| Point 4 | 25 | 37 | 390 |
| Point 5 | 20 | 33 | 392 |

The number of points, the number of dimensions and the parameter values for Table 2 were selected for ease of illustration.

The diagnostic system 104 proceeds to 612, where it determines a corresponding nearest point on the reference centroid line for each identified centroid point.

The diagnostic system 104 proceeds to 614 where it calculates the difference between each centroid point and the nearest point on the reference centroid line. In the study this was done using the squared distance formula discussed above, without weighting. See Equation 1.

The diagnostic system proceeds to 616, where it adjusts the reference points based on the centroid points and the nearest reference points. In the study, this was done by adding the difference between the centroid point and the nearest point of a cluster to the reference points in that cluster.

The diagnostic system proceeds to 618, where it redefines the reference centroid line using the adjusted reference points and the centroid points for each cluster. In the study, this was done by connecting centroid lines for each cluster using geometric bending. An example redefined reference centroid line is illustrated in FIG. 20 as line 704. The reference centroid line may be further refined using statistical analysis. For example, statistically insignificant points or points outside a defined radius may be removed from the data set. Calculations made by the diagnostic system 104 while employing the subroutine 600 may be stored for later use. For example, in clustering the data during the study the diagnostic system 104 determined the squared distance between the centroid points and the reference points. This data was stored for use in calculating standard deviation values.

The diagnostic system 104 proceeds to 620 where it returns the redefined centroid line and the value of any desired variables, such as user input. The diagnostic system proceeds to 622, where it stops.

In some embodiments, a system 100 may perform other acts not shown in FIG. 19, may not perform all of the acts shown in FIG. 19, or may perform the acts of FIG. 19 in a different order. For example, the subroutine may be made more iterative. For example, the subroutine 600 may be modified so that the system 100 determines after act 616 whether the number of clusters should be modified, and if so returns to act 608. The subroutine 600 may also call other subroutines to perform various functions.

Figure 21:
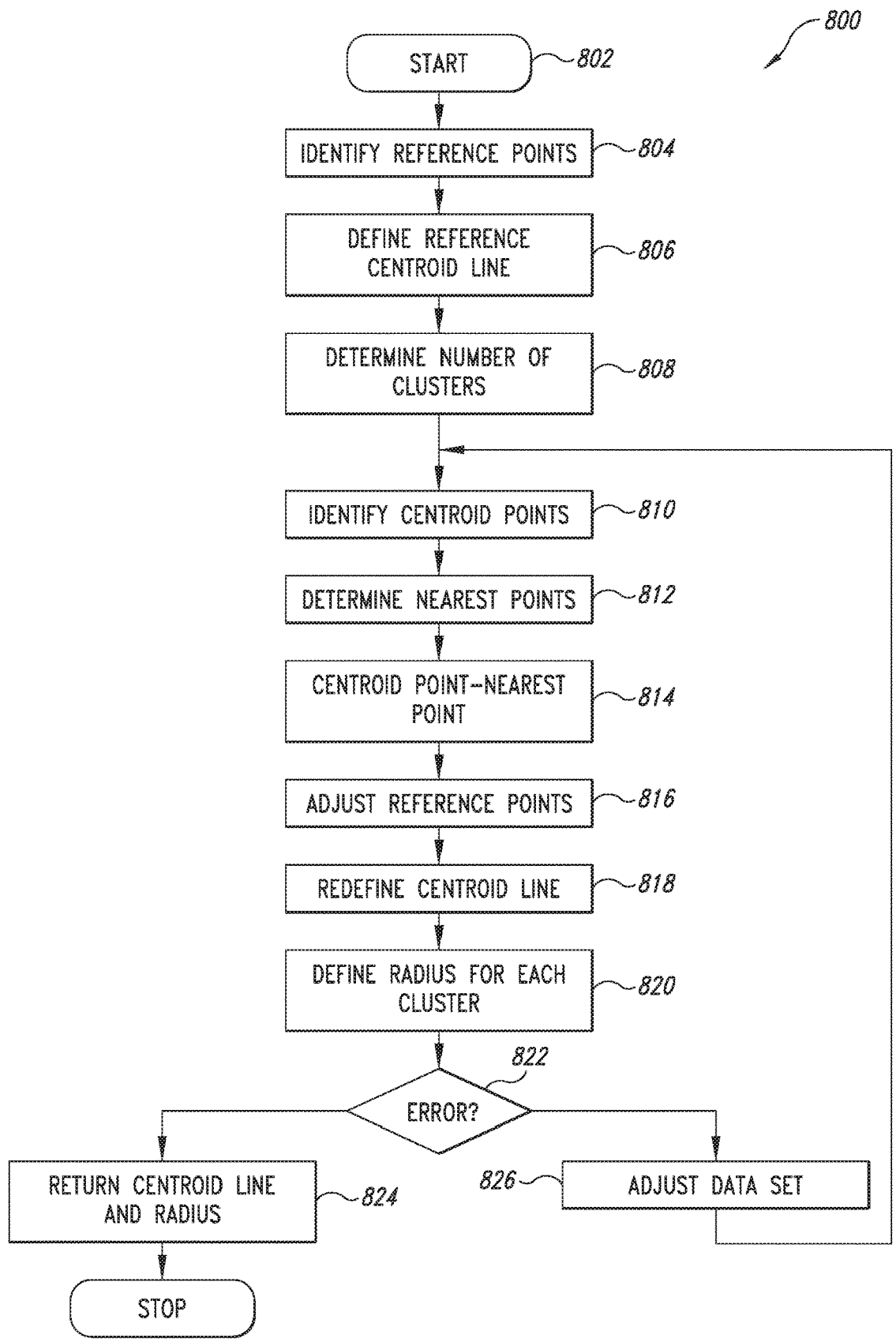
FIG. 21 is a flow chart illustrating operation of a system to define a normal centroid line and radius for a set of normal clusters corresponding to a normal cell lineage.

FIG. 21 is a flow diagram illustrating an example subroutine 800 that may be employed by a diagnostic system, such as the diagnostic system 104 illustrated in FIG. 1, to define a normal centroid line and a normal radius for a set of clusters.

The subroutine 800 starts at 802 and proceeds to 804. At 804, the diagnostic system 104 identifies a set of reference points. For example, the diagnostic system 104 may identify 10 reference points selected by a user after viewing various representations of the data set. Alternatively, the diagnostic system 104 may identify a number of statistically selected reference points or may identify the reference points based on statistical analysis combined with input from a user. In the study, a user selected the reference points after viewing various display representations of the data.

The diagnostic system 104 proceeds to 806, where it defines a reference centroid line based on the identified set of reference points. FIG. 20 illustrates an example initial reference centroid line 702 defined based on ten points identified by the user in the study.

The diagnostic system 104 proceeds to 808, where it determines the number of clusters in which to group the data. For example, in the study the diagnostic system 104 grouped the data into four clusters based on input from the user.

The diagnostic system 104 proceeds to 810, where it identifies centroid points for the corresponding number of clusters. This can be done by assigning each point to a cluster based on user input or statistical algorithms or, as in the study, on a combination thereof. See the discussion of clustering algorithms above. The respective parameter values for all the points assigned to a cluster are added together then the result is divided by the number of points in the cluster to obtain the parameter value for the centroid point. For example, if the diagnostic system 104 determined at act 808 to group the data into four clusters, the diagnostic system 104 would identify four centroid points, each point corresponding to a cluster.

The diagnostic system 104 proceeds to 812, where it determines a corresponding nearest point on the reference centroid line for each identified centroid point.

The diagnostic system 104 proceeds to 814 where it calculates the difference between each centroid point and the nearest point on the reference centroid line. In the study this was done using the squared distance formula discussed above, without weighting. See Equation 1.

The diagnostic system 104 proceeds to 816, where it adjusts the reference points based on the centroid points and the nearest reference points by using input from the user, statistical analysis or a combination thereof. In the study, the difference between the centroid point and the nearest point of a cluster was added to the reference points in that cluster.

The diagnostic system 104 proceeds to 818, where it redefines the reference centroid line using the adjusted reference points and the centroid points for each cluster. In the study, this was done by connecting centroid lines for each cluster using geometric bending, interpolation, etc. For example, two centroid points could be bracketed in the bend, additional secondary points could be added in the gap based on an analysis of the normal patient data set, for example, based on an average for the normal patients. An example redefined reference centroid line is illustrated in FIG. 20 as line 704.

The diagnostic system 104 proceeds to 820, where it defines a radius for the set of clusters. As noted above, the radius may be a function of position on the reference centroid line or in the n-dimensional space. The reference centroid line and radius may form various cluster shapes. For example, spherical clusters, hyperspheres or hyperellipsiods may be defined by the reference centroid line and radius. Clusters may be shaped like sausages or barbells or various other shapes. In the study, the user entered a radius for each cluster in the normal set of clusters, the radius being a distance from a nearest point on the reference centroid line.

The diagnostic system 104 proceeds to 822, where it determines whether an error criteria is satisfied. For example, the diagnostic system 104 may determine whether a statistically insignificant number of points are outside the clusters defined by the reference centroid line and radius. If the error criteria is satisfied, the diagnostic system 104 proceeds to 824, where the subroutine returns the defined centroid line and radius for the data set, as well as any other desired variables. If the error criteria is not satisfied, the diagnostic system 104 proceeds to 826, where it adjusts the data set. For example, the diagnostic system 104 may determine that statistically insignificant points in the data set should be disregarded. The diagnostic system 104 returns to 810, for further processing of the adjusted data set.

Some embodiments of a system 100 may perform other acts not shown in FIG. 21, may not perform all of the acts shown in FIG. 21, or may perform the acts of FIG. 21 in a different order. For example, the subroutine may be made more iterative. The subroutine 800 may also call other subroutines to perform various functions. For example, the subroutine 800 may call a subroutine to determine whether the identified clusters should be reclustered, such as the subroutine 900 illustrated in FIG. 22.

Figure 22:
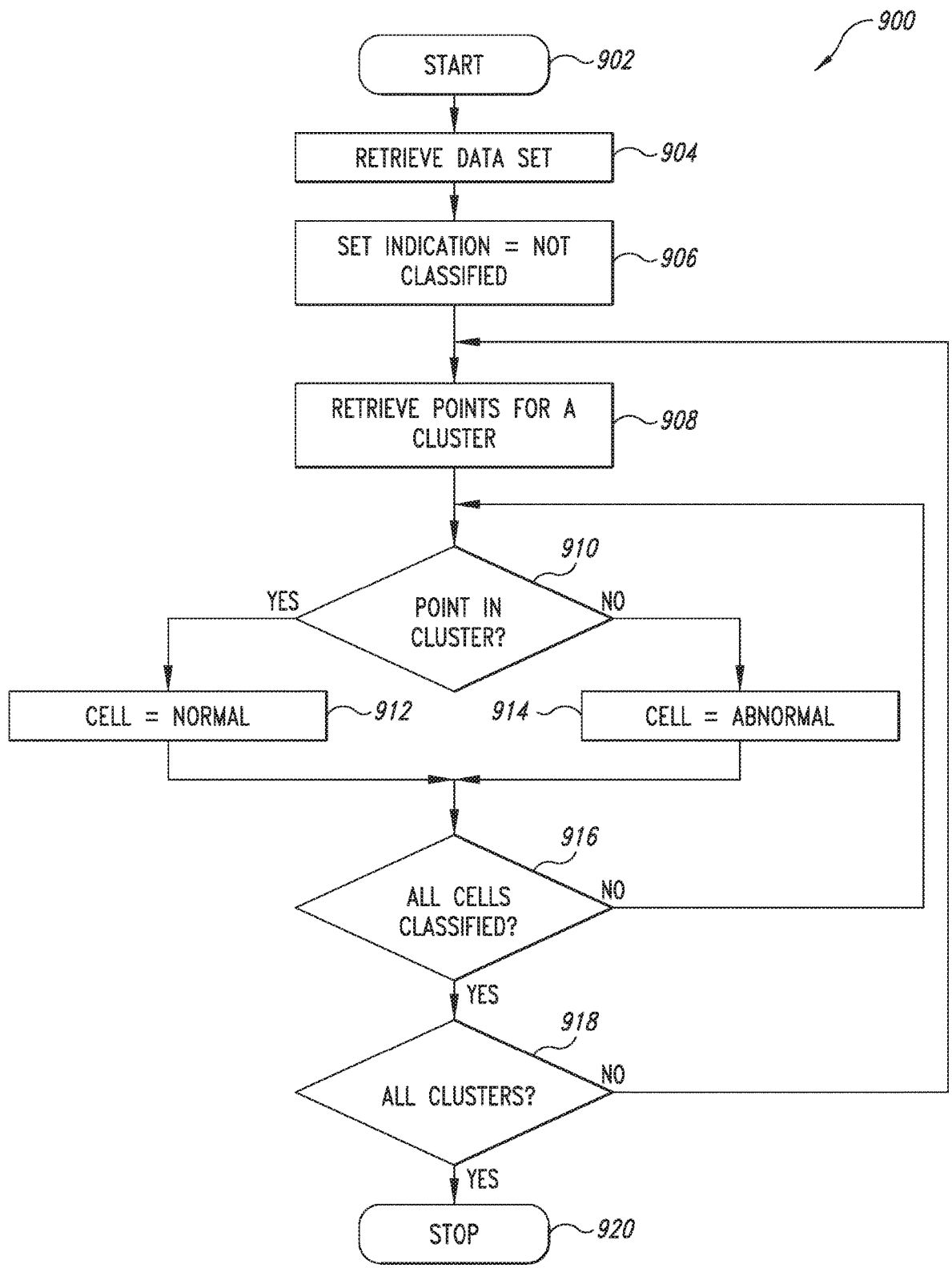
FIG. 22 is a flow chart illustrating operation of a system to determine whether points in a test set of data are contained within a set of normal clusters in an n-dimensional space.

FIG. 22 is a flow diagram illustrating an example subroutine 900 that may be employed by a diagnostic system, such as the diagnostic system 104 illustrated in FIG. 1, to determine whether points in a data set are contained within a set of clusters defined by a centroid line and radius. This information can be used by the diagnostic system 104 to, for example, determine whether a defined set of normal clusters should be redefined because too many cells are classified as abnormal, or to detect abnormal cells in a test set of cells.

The subroutine starts at 902 and proceeds to 904. At 904 the diagnostic system 104 retrieves the data set and proceeds to 906. At 906 the diagnostic system 104 sets a data field associated with each point in the data set to indicate that the subroutine has not yet classified the point and proceeds to 908.

At 908 the diagnostic system 104 retrieves the points associated with a selected cluster from the data set and proceeds to 910. At 910 the diagnostic system 104 determines whether an unclassified point associated with the selected cluster is within the centroid line and radius for the selected cluster. This can be done by, for example, computing the distance between the unclassified point and the nearest point on the centroid line for the cluster, classifying the point as normal if the distance is less than the radius of the cluster at the nearest point on the centroid line, and classifying the point as abnormal if the distance is not less than the radius of the cluster at the nearest point on the centroid line.

If the diagnostic system 104 determines at 910 that the point is within the selected cluster, the diagnostic system 104 proceeds to 912 where it classifies the cell as normal and indicates that the cell has been classified. If the diagnostic system 104 determines at 910 that the point is not within the selected cluster, the diagnostic system 104 proceeds to 914 where it classifies the cell as abnormal and indicates that the cell has been classified. The same data field can be employed to indicate whether a cell is unclassified, is classified as normal, or is classified as abnormal. Alternatively, two or more data fields may be employed to indicate respectively whether a cell has been classified and if so whether the cell is normal or abnormal.

The diagnostic system 104 proceeds from 912 or 914 to 916, where it determines whether all cells associated with the selected cluster have been classified. If the answer at 916 is NO, the diagnostic system 104 returns to 910. If the answer at 916 is YES, the diagnostic system 104 proceeds to 918. At 918 the diagnostic system 104 determines whether all clusters in the set of clusters have been processed. If the answer at 918 is NO, the diagnostic system 104 returns to 908. If the answer at 918 is YES, the diagnostic system 104 proceeds to 920, where the subroutine 900 stops.

Some embodiments of a system 100 may perform other acts not shown in FIG. 22, may not perform all of the acts shown in FIG. 22, or may perform the acts of FIG. 22 in a different order. For example, the subroutine 900 may be modified to process a data set sequentially, instead of processing the data a cluster at a time and without setting an indicator for whether a data point has been classified. The subroutine 900 may also call other subroutines, for example, the subroutine 900 may call a subroutine to calculate the distance between a point and the nearest point on a centroid line.

Data generated by the system 100, including data generated to define a normal cell lineage and data from a test set of cells, may be represented in various formats and used for various purposes. For example, as discussed above, the data may be displayed as multiple 2 by 2 projections of the multi-dimensional data in a Cartesian coordinate system or as pseudo three-dimensional projections of the multi-dimensional data in a Cartesian coordinate system. See FIGS. 4-10 and 12-17, and 20, discussed above. Color or shading can be used to show additional dimensions. These methods of displaying the data are particularly helpful to the user in defining and redefining a normal centroid and radius for a given maturation lineage.

Figure 23A:
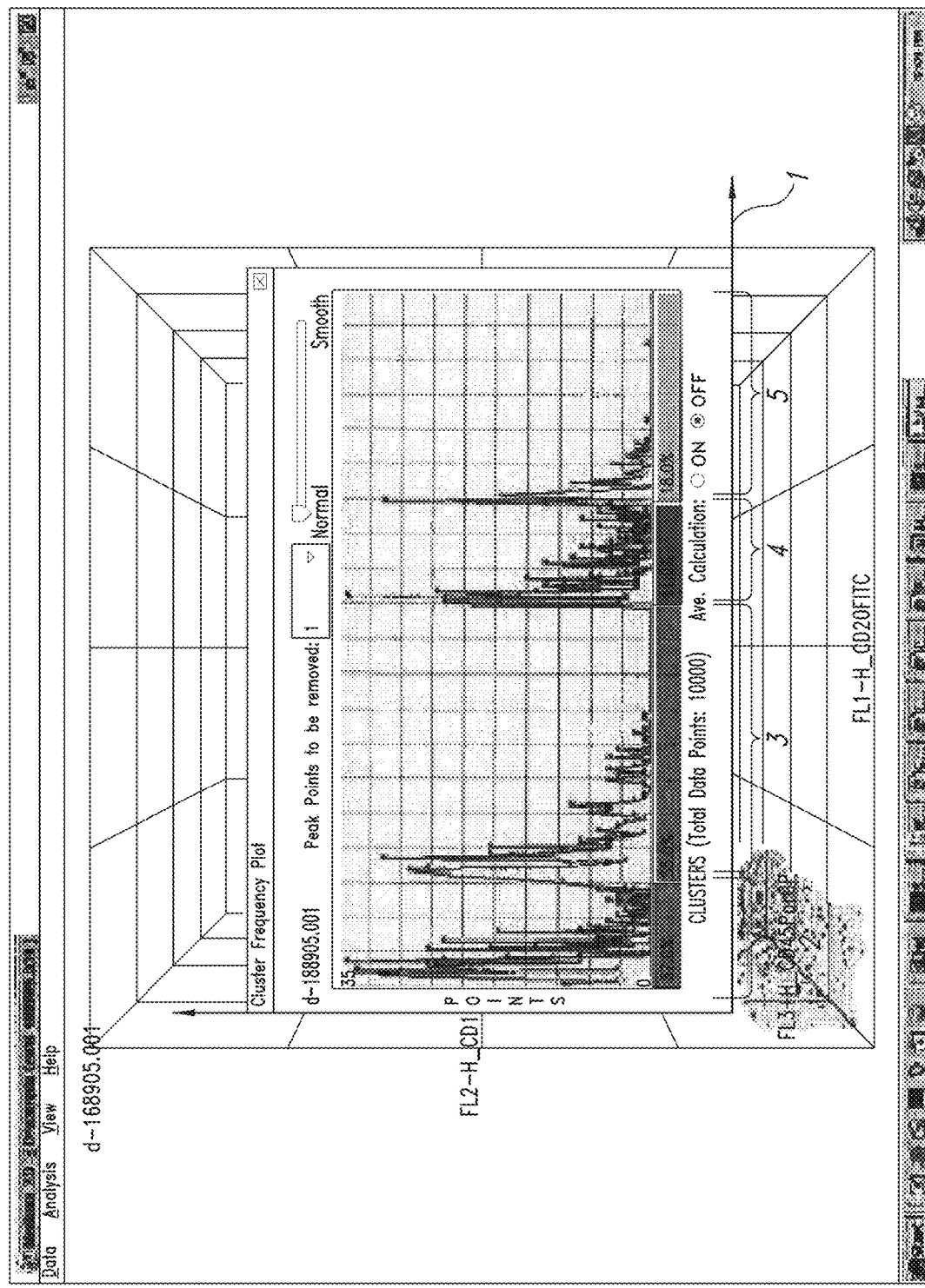
FIGS. 23A and 23B are illustrations of multi-dimensional data projected into pseudo three-dimensional displays generated by a system, such as the system illustrated in FIG. 1.
Figure 23B:
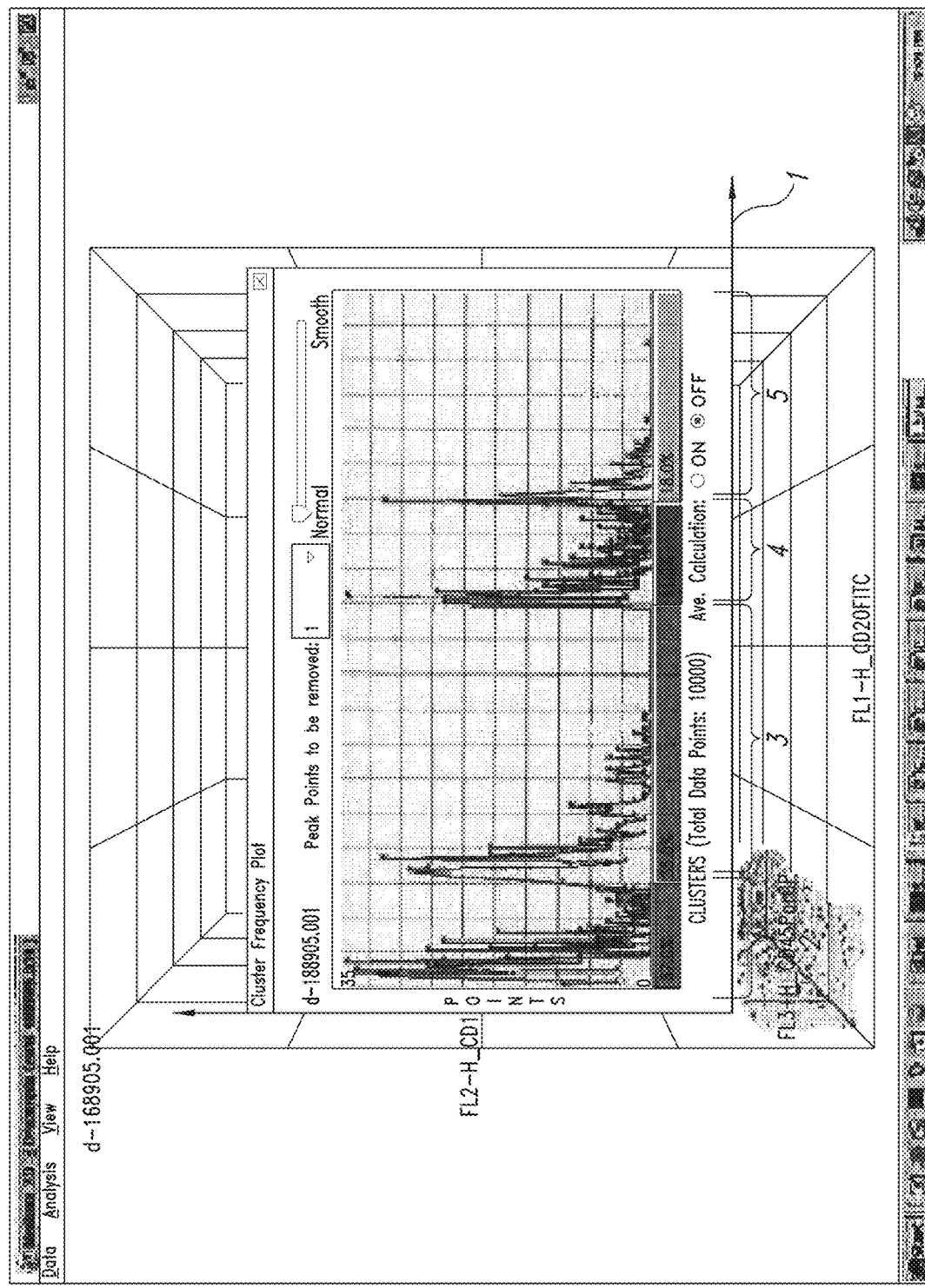

The data can also be displayed as a two-dimensional plot of continuous cell frequency along a defined centroid line. The position along the centroid line corresponds to a measure of time within the maturation process. Thus, a histogram may be generated displaying the group distribution of cells throughout the maturation process. FIGS. 23A and 23B (collectively FIG. 23) illustrate plotting of a sampled continuous cell frequency along a defined normal centroid line for a B lymphoid cell lineage. A horizontal axis 1 corresponds to position along the defined centroid line. Four clusters 2, 3, 4, 5, corresponding to stages of maturation, are identified along the horizontal axis 1. A vertical axis 6 corresponds to the number of points in the data set at various sample points along the centroid line. In FIG. 23, 108 sample points were selected for the centroid line as follows. Ten reference points along the centroid line were identified. Midpoints along the centroid line were calculated for the ten reference points, yielding 19 points. Six midpoints were then calculated for the 19 points, yielding 108 points. The percentage of total data points sampled for each cluster is displayed as well.

Additional specimens may be used to define the normal centroid and radius. For example, the two-tube, 4 color panel process described above could be used to stain a larger number of bone marrow specimens exhibiting normal antigen expression. These specimens could be selected from routine work flow, and may include specimens from bone marrow donors, patients without hematologic neoplasms, and patients post transplant with 100% donor chimerism who were transplanted for diseases that were not ALL. The specimens may include both pediatric and adult specimens. The additional specimens may be random, or selected with respect to desired criteria, such as sex, age or minority group. It is expected that selection by sex, age or minority group will not result in significant differences in the defined normal centroid and radius for B lymphoid maturation lineage.

The expanded data set may be used to assess the variability of cluster positions for the individuals from whom specimens are collected as well as differences in composition that are expected in a routine analysis of specimens. The data set may also include and/or be compared with data from patients with abnormal bone marrow specimens that are not a result of a clonal or neoplastic process, such as specimens from patients early post stem cell transplant containing only the most immature cells or patients treated with Rituxan (anti-CD20). In these patients the B lymphoid development in the bone marrow is truncated at the beginning of Stage II with any cells expressing CD20 being eliminated by the drug. The data set may also be compared to peripheral blood specimens that will contain only Stage IV cells.

Figure 24:
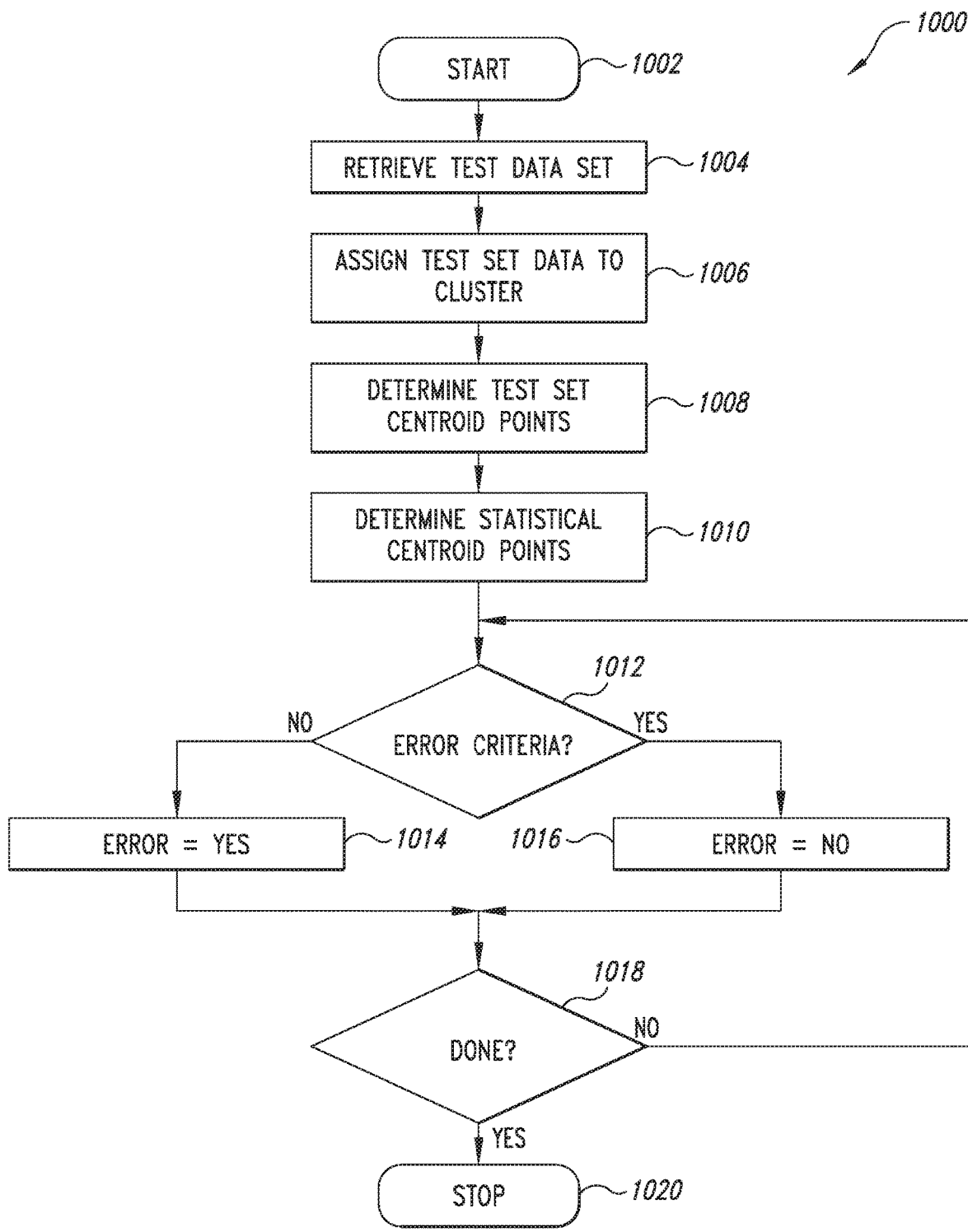
FIG. 24 is a flow chart illustrating operation of a system to compare a test set of data to defined centroid points for a set of normal clusters.

FIG. 24 is a flow diagram for an example subroutine 1000 that may be employed by a diagnostic system, such as the diagnostic system 104 illustrated in FIG. 1, to compare a test set of data to a normal set of clusters defined by centroid points. This information can be used by the diagnostic system to, for example, determine whether a defined normal set of clusters should be redefined.

The subroutine starts at 1002 and proceeds to 1004. At 1004 the diagnostic system 104 retrieves the test data set and proceeds to 1006. At 1006 the diagnostic system 104 assigns the points in the test set of data to clusters, as discussed elsewhere herein (e.g., using gating, using clustering algorithms, using support vector machines, etc., and various combinations thereof), and proceeds to 1008. At 1008, the diagnostic system 104 determines a centroid point for each cluster in the test data set, as discussed above. For example, the diagnostic system could determine the parameter values for the centroid point of a cluster by adding the corresponding parameter values for each point in the cluster and dividing the result by the number of points in the cluster. Alternatively, the diagnostic system could use a statistically adjusted centroid point for the test data set. The diagnostic system 104 proceeds from 1008 to 1010.

At 1010, the diagnostic system 104 determines the corresponding statistical centroid points for each cluster based on previously analyzed data sets. For example, parameter values for a statistical centroid point could be determined by adding the corresponding parameter values for defined centroid points for a set of previously analyzed data sets and dividing the result by the number of data sets. The diagnostic system 104 proceds from 1010 to 1012.

At 1012, the diagnostic system 104 determines whether an error criteria is satisfied for a cluster in the test data set. For example, the diagnostic system 104 may compare the log of the distance between the centroid point of the cluster and the corresponding statistical centroid point to a threshold value, such as 2.5. If the log of the distance is greater than the threshold value, the diagnostic system 104 may determine that the error criteria is not satisfied. Other error criteria may be employed.

If the diagnostic system 104 determines at 1012 that the error criteria for a cluster in the test data set is not satisfied, the diagnostic system 104 proceeds to 1014, where an indication of an error is set for the cluster in the test data set. If the diagnostic system 104 determines at 1012 that the error criteria for a cluster in the test data set is satisfied, the diagnostic system 104 proceeds to 1016, where an indication of no error is set for the cluster in the test data set.

The diagnostic system 104 proceeds from 1014 or 1016 to 1018, where it determines whether all of the clusters in the test data set have been evaluated. If the diagnostic system 104 determines at 1018 that not all of the clusters have been processed, the diagnostic system 104 returns to 1012. If the diagnostic system 104 determines at 1018 that all of the clusters in the test set have been evaluated, the diagnostic system 104 proceeds to 1020, where the subroutine 1000 stops.

Some embodiments of a system 100 may perform other acts not shown in FIG. 24, may not perform all of the acts shown in FIG. 24, or may perform the acts of FIG. 24 in a different order. For example, the subroutine 1000 may be modified to sequentially compare all data sets in a normal set of data sets to determine which data sets should be removed from the normal set of data sets.

Once the cluster boundaries (normal centroid and radius) are defined for a normal maturation lineage, a test sample can be analyzed by subjecting it to the same reagent exposure and measurement protocols used on the data sets used to define the normal maturation lineage. The results for the test data sample can then be compared to the defined normal maturation lineage, allowing the test sample to be characterized and diagnosed. A system, such as the system 100 illustrated in FIG. 1, need only be provided with the definition of the normal cluster boundaries to diagnose a test sample. Alternatively, the system 100 may be provided with the defined normal data set and the defined centroid line and radius, or the system 100 may be provided with the defined normal data set and may determine the definition of the normal cluster boundaries.

Figure 25:
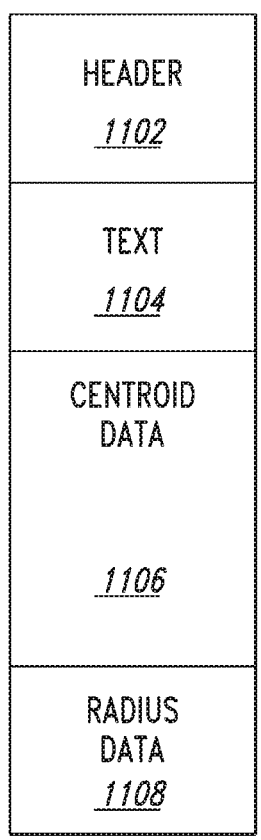
FIG. 25 is a schematic diagram of a data structure suitable for storing information to define a centroid and radius for a set of normal clusters in an n-dimensional space.

FIG. 25 illustrates a data structure 1100 suitable for providing the definitions for the defined normal boundaries for a cell lineage. The data structure 1100 and corresponding instructions can be stored in a computer readable media, such as a memory, which may include the memory 112 illustrated in FIG. 1, or portable memories, such as CD ROMs, floppy disks and/or flash memories, and/or transmitted as a signal in a signal transmission media, such as a wired or wireless media. The data structure 1100 has a header section 1102 describing the locations of the other sections of the data structure 1100. A text section 1104 contains information that describes various aspects of the data structure 1100, such as the number of clusters and how the centroid line and radius are defined. For example, the centroid line may be defined by providing parameters for insertion into an equation or by providing reference points that are to be connected together, or a combination thereof. Similarly, the radius may be defined by providing parameters for insertion into an equation or fixed radius values for a cluster, or a combination thereof. For example, the radius may have a fixed value within one cluster and may be a function of position within a second cluster. A centroid data section 1106 of the data structure 1100 contains information defining the centroid line and a radius data section 1108 contains information defining the radius. If desired, a normal data set used to define the normal centroid line and radius may be provided, either as an additional data field in the data structure 1100 or in a separate data structure, such as the data structure 200 illustrated in FIG. 2.

The individual clusters may also be broken down into subclusters, which can be defined and analyzed using processes similar to those discussed above. For example, the subroutine 800 illustrated in FIG. 21 could be modified to define a centroid line or point and radius for a subcluster and the subroutine 900 illustrated in FIG. 22 could be modified to determine whether a test set of cells contains a subcluster corresponding to a defined subcluster. It is expected that dbscan clustering would be particularly useful in identifying subclusters corresponding to submaturation level within a cluster corresponding to a maturation level within a cell lineage.

A system 100 can be used to diagnose a test data set by comparing the test data set to the defined normal centroid line and radius for the cell lineage. The entire test data set can be compared to the defined normal and displayed by a diagnostic system, such as the diagnostic system 100 in FIG. 1, on a suitable display device or media, such as a raster scan, an active or passive matrix display, or on a passive media, such as paper or vellum. Alternatively, data events in the test data set lying within "normal" positions, specifically B lineage lymphoblasts, may be subtracted from the test data set leaving an "abnormal" data set corresponding to residual populations of potential "abnormal" cells (leukemic lymphoblasts). The remaining abnormal events can then be analyzed and displayed by a diagnostic system, such as the diagnostic system 104 illustrated in FIG. 1, and the user. The remaining abnormal events may define an abnormal subset of the test set of data. Clustering techniques, such as those discussed above, can be used to identify clusters with the abnormal subset of the test set of data and statistical analysis can be employed to determine whether any identified clusters within the abnormal subset are significant.

The system 100 may be tested before being employed to diagnose cancers. For example, a number of specimens from patients with overt ALL may be stained and data collected for comparison to the normal specimens. It is expected that these specimens will have identifiable normal cells that the system 100 will identify as well as CD19 positive leukemic cells that will not fall within the boundaries defined by the normal centroid line and radius. It should be noted that B lineage ALL leukemic cells all express CD19 and, therefore, will be included within the original gating strategy.

Testing of the system 100 may include mixing different proportions of data from the ALL patients with normal specimens to mimic residual disease detection. For example, the system 100 may process 25 normal specimens and generate a defined centroid line and radius for a normal maturation lineage, which the system 100 may store in the memory 112 as digital objects. This information may be looped back with the statistical algorithms on a data file containing an aberrant cell cluster. The cell events confined to the region of normal clusters can be removed with the remaining events representing an "abnormal" cluster. The number and location of tumor cells expected in the mix can be compared to those identified. This can be done both before and after the "normal" cells are subtracted from the test data set.

Smoothing algorithms, including averaging and filtering algorithms, may be employed to smooth the representation of the data. For example, a portion of one cluster could be averaged. For example, it may be known that the average maturation level for a portion of a particular cluster is a significant indicator of whether a test sample is normal, but that individual variances over that portion of the cluster are not significant.

Data for two sets of data may be simultaneously displayed in this manner. For example, data from a test sample may be superimposed over data used to define the normal centroid line. A first color or other indicator could be used to illustrate the normal distribution and a second color or other indicator could be used to illustrate the distribution of the test specimen.

More simplified displays of the data may be employed and compared for visual impact and ease of interpreting normal and/or abnormal development. For example, the proportions of cells in each of the four B lymphoid cell lineage stages may be plotted to represent the clusters identifiable in the data space. The total events in each of the four clusters may be displayed to represent the maturation of cells within normal bone marrow and/or to a test sample against a normal representation. The parameters of abnormal cells that can be depicted include: number of abnormal events, distance from normal, dispersion within the abnormal population, and cellular markers that distinguish the aberrant cells from normal.

Figure 26:
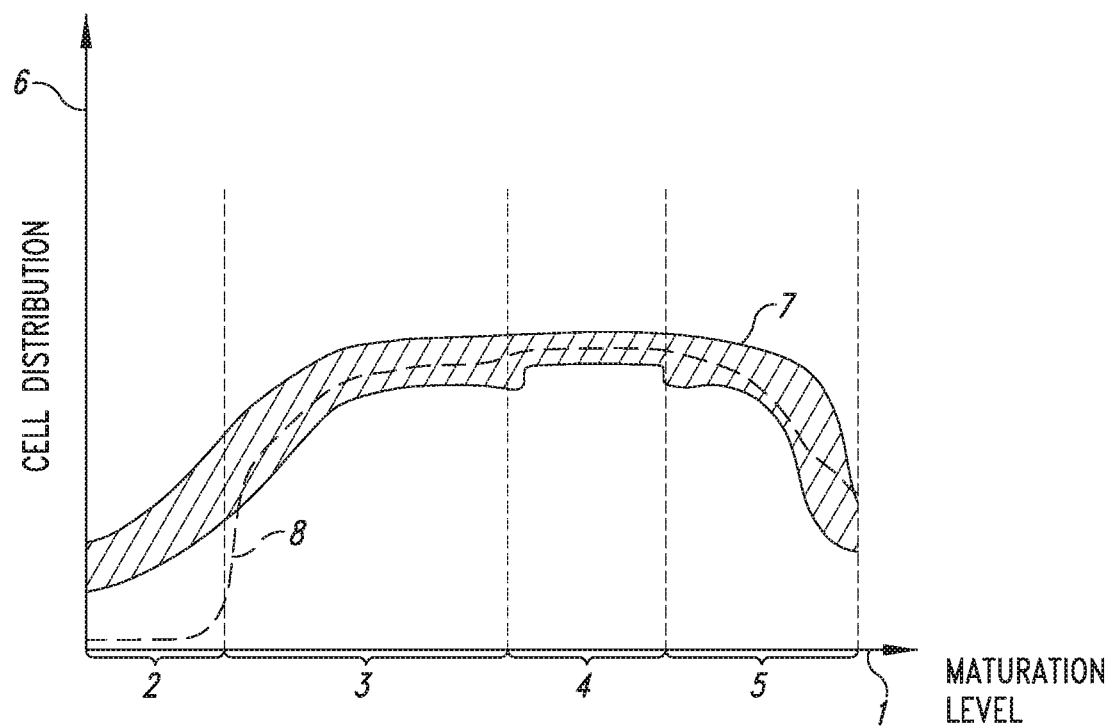
FIG. 26 is an illustration of multi-dimensional data projected into a pseudo two-dimensional display generated by a system, such as the system illustrated in FIG. 1.

FIG. 26 illustrates an example simplified representation of data gathered from a test sample superimposed on a representation of a defined normal data set. A horizontal axis 1 corresponds to an indication of maturation level of a cell lineage and indicates four stages 2, 3, 4, 5, corresponding to maturation level clusters within the cell lineage. A vertical axis 6 corresponds to an indication of the number of cells at various maturation levels. The indication may be, for example a percentage of the total number of cells within a stage or a logarithmic indicator. A band 7 illustrates a defined normal range for a sample. The band 7 may correspond, for example, to a standard deviation for a normal set of cells, or it may correspond to a defined centroid line and radius for a normal set of cells. A dashed-line 8 illustrates the results for a test sample.

A quality control process may be employed. For example, bead preparations may be used to assess instrument performance, such as Rainbow beads (RCP and RFP, Spherotech, Libertyville, Ill.) which are plastic microspheres with dye embedded inside the particle insuring fluorescence stability. The RFP beads have only a single peak in each of the four fluorescence channels and are used as a primary standard. The RCP beads, a mixture of six intensity beads observed in all channels, serve as a secondary standard and provide data regarding linearity for each of the fluorescence detectors. Fluorescence emission spectral compensation is established and monitored by staining normal blood with anti-CD4 antibody conjugated with each of the chromophores used (FITC, PE, PerCP, and APC). Cells stained with these antibodies separately are analyzed to ensure fluorescence from the expected chromophore is detected only in the appropriate fluorescence channel (24). Each lot of reagent used in the assessment of cells is titered before it is placed into inventory. A titer of antibody yielding maximum fluorescence intensity is selected and specificity of reagent is checked for each new lot of antibodies.

Using these quality control procedures, two flow cytometers experimentally generated identical results for the same specimen. In a study of normal adult blood using these quality control procedures, the intensity of CD4 on lymphocytes was found to be almost invariant for 21 individuals assayed on the two instruments collected over a period of eight months. The mean fluorescence intensity of CD4 for these 21 individuals was 1596+/−116 standard deviation fluorescence units resulting in a CV of 7%. These results demonstrate that in a data space with a dynamic range of four decades, the biological variation from individual to individual for this one antigen is essentially nil. The amount of CD4 expressed on lymphocytes is, by itself, a biological standard. The quantification of the centroid line position (measured on immature bone marrow cells) may be compared to the variability of antigens expressed on normal mature blood cells, which will provide a basis for understanding the biological variation between individuals with respect to the intensity of antigen expression during maturation of blood cells not just on mature cells.

The tolerance of a system, such as the system 100 illustrated in FIG. 1, may be determined by changing the target value for the primary standard fluorescent quality control beads by a known amount (factors of 2, and 4). In other words, a system may be detuned by known amounts. Each channel may be tested separately and the channels may be tested together, after establishing proper compensation. For example, Bone marrow cells stained with the four color combinations may be collected under each setting and the data analyzed using the system to be tested. This will assess how far from optimum standard setup a system can operate and still permit correct identification of cells of the stages of development by the system. This performance then defines the tolerance required of a quality control program based on the ability of the system to identify the appropriate cell populations.

As discussed above, abnormal cells may be detected using multi-dimensional analysis. In general, a centroid line is defined to model maturation of a cell lineage based on a normal patient data set, which typically includes data from multiple normal patients. A radius of normal variation around the line is defined based on the normal patient data set.

Subsequently, a test set of cells (e.g., cells from a patient) may be characterized based on identifying cells in a test set which are outside of this radius. Such cells may be identified, for example, in terms of percentages, locations, etc., and the test set of cells may be classified as normal or abnormal based on the identification of the cells outside of the radius. In the description that follows, reference to a cell in a set of cells may refer to a cell in a set of cells to be exposed to a defined protocol, or may refer to a corresponding data point in a set of data points generated based on flow cytometry, as indicated by the context in which the reference is used.

Defining Individual Variation in Flow Cytometric Data Based on Internal Reference Populations The use of flow cytometry to detect hematologic malignancies is based on identifying cells that do not exhibit antigens or physical properties expected of normal hematopoietic cells. This approach depends on how precisely normal blood and bone marrow cells can be identified using quantitative antibody binding in combination with physical characteristics such as light scatter. A powerful combination of characteristics has been used to classify cells of different lineages called CD45 gating in which the data for a specimen are displayed combining CD45 intensities with light scatter (side scatter, right angle light scatter or orthogonal light scatter). See, e.g., Stezler G T, Shults K E, Loken M R. "CD45 gating for routine flow cytometric analysis of human bone marrow specimens." Ann N Y Acad Sci 1993; 677: 265-80.

Determining the composition of bone marrow using this technology is daunting as this tissue is comprised of at least 11 different cell types as well as the entire range of immature cells from the hematopoietic stem cell to the mature cells in the blood. The Applicants have realized that understanding the variability from individual to individual for all of the cellular characteristics facilitates identifying abnormal cells as different from normal hematopoietic cells, quantifying the abnormal cells, characterizing the abnormal cell immunophenotypes and physical characteristics, and then classifying the abnormal cells based on the nearest normal cellular component. The limit of this approach is dependent on the variability observed between individuals for these assayed parameters over a period of time. Based on this realization, the Applicants have developed methods to reduce the variability observed for normal cells of each lineage between individuals as well as to reduce the analytic variance (variance due to specimen processing, multiple reagent lots, different analytical instruments, different analysts, etc.) used to detect those characteristics.

A first step in analyzing the composition of a bone marrow specimen is to identify key reference cell populations within the specimen. The selected reference populations form clusters in multidimensional data space and can be unambiguously identified using the proper reagent combinations. Subjective bias in identifying these specific cell populations can be reduced by using analytic procedures that are automated. These reference populations may then be used to improve the identification and the analysis of other cell populations in multidimensional data space. The Applicants have realized the relationships of the cellular characteristics between these reference populations are surprisingly constant and the variability can be reduced by normalization of the data set relative to a single cell population. This may facilitate standardization of the analysis of bone marrow and comparing the analysis of centroids for each of the maturing cell lineages from patient to patient.

Certain reference populations can be reproducibly identified in bone marrow specimens of normal individuals. These populations include: mature lymphocytes, uncommitted progenitor cells, promyelocytes, mature monocytes and mature neutrophils. Each of these populations can be specifically identified by a combination of antibodies and light scattering characteristics, as set forth in Table 3, below.

TABLE 3

Phenotypic and Light Scatter Characteristics of Reference Populations

| Reference Population | Light-Scatter Characteristics |
| --- | --- |
| Mature Lymphocytes | High CD45, Low FSC, low SSC |
| Uncommitted Progenitor cells | Bright CD34, CD33 positive, low SSC intermediate CD45 |
| Promyelocytes | HLA-DR−/CD11−, high SSC, intermediate CD45 |
| Mature monocytes | CD14+, High CD33+, high CD45, intermediate SSC |
| Mature Neutrophils | High CD13, intermediate CD33, high CD45, high SSC |

The reference populations can be identified automatically. The analysis may be used to eliminate or reduce subjective bias by a technician or other person analyzing the data. In addition, automating the analysis may simplify the process. One embodiment uses a machine learning analysis called a support vector machine (SVM), as discussed in more detail below. A support vector machine can be taught by providing a series of examples in which an "expert" manually identifies each reference population of interest. The support vector machine identifies mathematical features associated with these expert identifications of cell populations, and uses these mathematical features to find such populations in subsequent data from different patients. Thus, the support vector machines present a reproducible methodology to mathematically identify reference populations of interest which may reduce subjective bias in the analysis and facilitate automating the process. The SVM methodology was tested on pediatric patients (n=50) recently treated for acute myeloid leukemia (AML). These "stressed" bone marrow specimens recovering after chemotherapy were randomly selected from those patients who did not exhibit residual AML, with the additional criteria that the specimen be high quality with respect to adequate cell numbers, lack of hemodilution and minimal dead cells.

Once reference populations are identified by the SVM, the means and standard deviations of antigen intensities for cells (data points) in these reference populations can be computed. There is an inherent (but small) variability in these mean antigen intensities between patients. The variability of position for each of these reference populations can be further reduced by normalizing the data relative to the position of a single-cell population. For example, the CD45 and SSC position of progenitor cells can be normalized to the CD45 and SSC of the respective mature lymphocytes for each patient. In another example, the CD33 and CD45 intensity of the monocytes may be standardized to the CD33 vs CD45 intensity of each patient's respective progenitor population, as discussed in more detail below with reference to FIG. 29. The CD33 antigen is not highly regulated with respect to absolute amounts, but this standardization showed that the difference in CD33 intensity is consistent between cell populations within one individual patient. Overall, this data normalization methodology drastically reduces the variability in position of each reference population, allowing for an even-more precise and standard assessment of disease.

Using Support Vector Machines to Select Reference Populations of Interest

As discussed elsewhere herein, a user may filter certain flow cytometric parameters (e.g., CD19, SSC, etc.) to select a population of cells (e.g., reference cells) on which to access maturation.

Traditionally, algorithms used to analyze flow cytometry data are unsupervised algorithms in that the algorithms search for patterns in the data. For example, many automated flow cytometry analysis algorithms search for clusters of cells with similar fluorescence characteristics. Notably, for these algorithms the quantified fluorescence characteristics are not important; all that is important is that there are a group of "similar" cells that can be clustered together. Current automated flow cytometry analysis programs use such unsupervised approaches because the fluorescent intensity data is not consistent—and thus finding groups of similar cells allows finding of homogenous cell populations.

In an embodiment, support vector machines ("SVMs") may be employed to select populations of cells (data) to access maturation within a cell lineage. A multidimensional boundary may be defined using SVMs to select the cell population of interest, or the reference population. This boundary is independent of the frequency of the reference population. If the reference population is present at a low frequency, clustering algorithms may have difficulty identifying the reference population. An SVM looks for positions in space to detect the reference populations instead of the frequency of the reference populations.

Support Vector Machines may be considered a supervised machine learning algorithm, meaning that the SVM is given data to "learn" how to identify a cell population of interest. In a study, the SVM classifications of cell types were provided to an SVM, and the SVM identifies mathematical features in the classifications based on the quantitative fluorescence characteristics (as opposed to being based on identifying clusters or groups of cells based, for example, on statistical clustering techniques). In the study, incredibly stable fluorescent intensity measurements were produced by a carefully constructed and quality controlled flow cytometry test, which facilitate predicting if an individual cell will belong to a population based on the cell's fluorescent intensity characteristics. This facilitates identifying an entire lineage of cells (in all maturational stages) without any user-input (gating) in cases where no single antibody defines the group of interest.

Previously, the multiple lineages had to be defined (manually) by an analyst. Most flow cytometry experts have difficulty separating cells of different lineages, especially monocytes and neutrophils. In an embodiment, using an SVM facilitates automating the process because the SVM automates the classification of cells into different lineages, even without a specific lineage marker. This facilitates assessing the maturation of each lineage separately and classifying each lineage as normal or abnormal.

Figure 27:
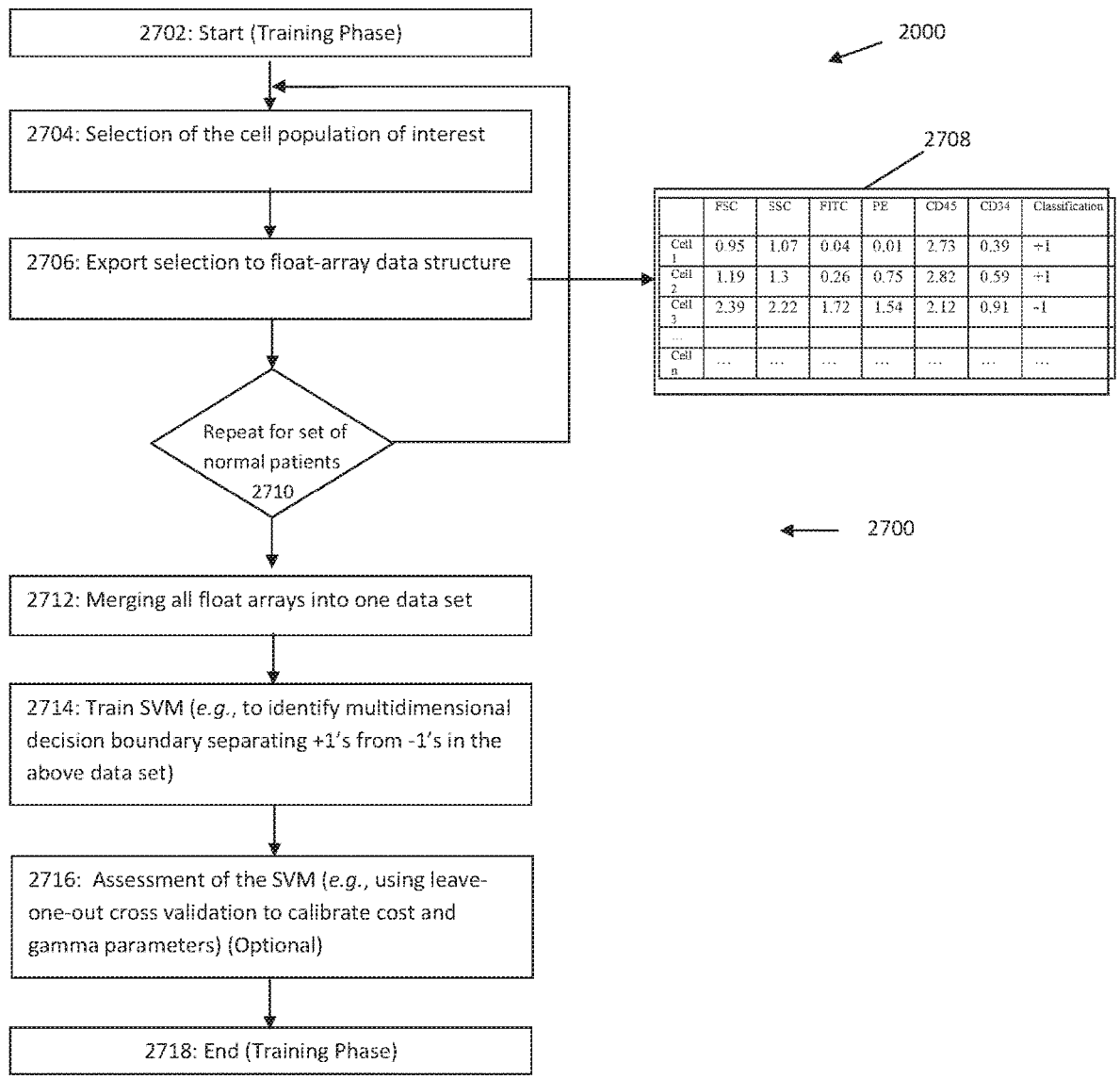
FIGS. 27 and 28 are flow charts respectively illustrating a training phase and an implementation phase of a subroutine to define a reference population in an n-dimensional space.
Figure 28:
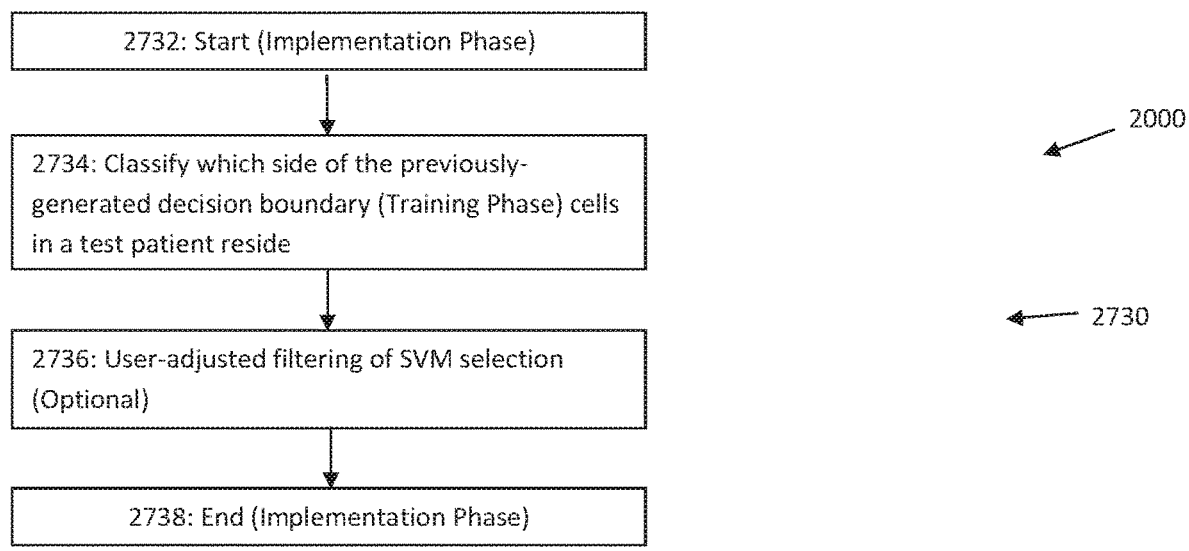

FIGS. 27 and 28 are a flow diagram of an example SVM subroutine 2000 that may be employed by a diagnostic system, such as the diagnostic system 104 of FIG. 1, to identify cell populations of interest in a data set using multidimensional boundary definitions generated using SVMs. For convenience, the subroutine 2000 will be discussed with reference to the diagnostic system 104 of FIG. 1. These definitions may be used by the diagnostic system to, for example, identify or refine sets of cell populations of interest to access maturation within a centroid (e.g., to assign cells to clusters in a set of normal clusters), to identify reference populations to use in defining or refining a centroid line or a radius of a centroid line or segment thereof, to perform vector normalization, to classify a test set of cells, etc.

As illustrated, the SVM subroutine 2000 includes a training phase 2700 and an implementation phase 2730. In the training phase 2700, the SVM subroutine 2000 is taught to automatically identify groups of cells. In the implementation phase 2730, the SVM subroutine 2000 identifies cell populations of interest, such as a reference cell population, a cell population of a new test patient, etc., which may be employed, for example, to assign cells to cluster of a set of normal clusters, to perform vector normalization, to access a maturation of the population via the centroid line, to refine a radius, to characterize a test set of cells, etc.

The subroutine starts at 2702 and proceeds to 2704. At 2704 the diagnostic system 104 selects a test cell population of interest in a data set. This may be done, for example, using an existing software platform (e.g., Winlist, Java implemented with a Java Run Time Environment, a 3-D Java Run Time Environment, etc.), to manually set a series of one or more gates to select a cell population of interest in the data set. The diagnostic system proceeds from 2704 to 2706.

At 2706, the diagnostic system 104 generates a data set identifying the selected cells. For example, a data set identifying the selected cells may be exported to a float-array 2708 in a text file format, with one column for each measured parameter and an additional classification column, and one row for each cell in the data set. As illustrated, the classification column contains a binary assessment for each cell of a test data set, −1 if the cell is not included in the defined population and +1 if the cell is included in the defined population. Other data formats could be employed, for example, a comma separated value file, etc.

The subroutine 2000 proceeds to 2710, where the diagnostic system 104 determines whether there are additional data sets to process. For example, a number of data sets corresponding to cells from a number of normal patients may be employed to train the SVM. When it is determined at 2710 that there are additional normal patient data sets to process, the subroutine 2000 returns to 2704 to process the next normal patient data set. Otherwise, the subroutine 2000 proceeds to 2712.

At 2712, the diagnostic system 104 combines the data sets indicating the cell populations of interest. In a study, this was done by reading in the float arrays from each of the normal data sets (e.g., float arrays 2708) and merging the float arrays into one combined data set. The subroutine 2000 proceeds to 2714.

At 2714, the diagnostic system 104 generates an SVM that identifies a multidimensional decision boundary identifying the cells of interest in the combined data set (e.g., an SVM separating the cells assessed as +1 from the cells assessed as −1). The decision boundary may typically be of a complex, multidimensional shape. Cells on one side of the boundary are classified as belonging to the population of interest (e.g., classified as +1), while cells on the other side of the boundary are classified as not belonging to the population of interest (e.g., classified as −1). It is known how to generate SVMs as predictive algorithms, and these known techniques may be applied to the combined normal data set to generate the SVMs identifying the multidimensional boundary. See, e.g., Chang, Chih-Chung, and Chih-Jen Lin. "LIBSVM: a library for support vector machines." ACM Transactions on Intelligent Systems and Technology (TIST) 2.3 (2011): 27. The subroutine 2000 proceeds to 2716.

At 2716, the diagnostic system 104 optionally assesses the predictive performance of the SVM, and may, for example, adjust cost and gamma factors, the number of test normal patient data sets used to generate a combined normal patient data set to train the SVM, etc., based on the assessment. For example, leave-one-out cross validation may be employed. See, e.g., Golub G, Heath M, Wahba G. Generalized cross-validation as a method for choosing a good ridge parameter. Technometrics 1979; 21(2): 215-23. The process is generally a two step process. The results are optimized and then assessed. Cross-validation is a methodology used to optimize input parameters in an algorithm. Assume a training data set of 25 patients. For a fixed-combination of input parameters (such as cost, gamma input parameters for the SVM), an algorithm is cross-validated by being trained on a subset of the training data (e.g. 24 patients, instead of 25), then tested on the remaining patients (e.g., the 1 patient). The errors made by the SVM are totaled, and the process is repeated, so that every patient is the testing patient exactly one time. The total errors (from the 25 repetitions of the testing patient) are tallied and stored for that particular combination of input variables. Then, the input variables (cost, gamma) are adjusted, and the process of training (n=24) and testing (n=1) is repeated in the same way for a new combination of input variables. In the assessment phase, the number of total errors from each combination of input variables are compared, and the combination of input variables with the lowest total errors is used to train the resulting SVM. The subroutine 2000 proceeds to 2718, where the training phase ends.

The implementation phase 2730 of the subroutine begins at 2732. The subroutine proceeds from 2732 to 2734. At 2734, the diagnostic system 104 classifies each cell of a test patient set of cells (e.g., cells of a test patient which may or may not be a normal patient) using the multidimensional decision boundary defined in the training phase. In other words, each cell in the test set of cells is classified as +1 or −1 based on the side of the decision boundary on which the cell resides. The subroutine 2000 proceeds from 2734 to 2736. At 2736, the diagnostic system 104 optionally applies additional filtering criteria (e.g., filtering based on certain flow cytometric parameters, such as CD19, SSC, etc., which may be done based on default settings, in response to user input, etc.). The subroutine 2000 proceeds to 2738, where the subroutine 2000 stops.

Some embodiments of a system 100 may perform other acts not shown in FIGS. 27 and 28, may not perform all of the acts shown in FIGS. 27 and 28, or may perform the acts of FIGS. 27 and 28 in different orders. For example, the subroutine 2000 may be modified in some embodiments to only perform the training phase 2700 and may be modified in other embodiments to only perform the implementation phase 2730 (e.g., a first diagnostic system 100 may be used to train the SVM, and a second diagnostic system may be used to apply the defined multidimensional boundary to test data sets, SVMs may be stored for reuse instead of being generated, etc.). In another example, the subroutine may determine after 2716 that additional normal data sets should be employed, for example in response to an indication that the generated boundary is not sufficiently reliable as a predictor of a normal cell population, and thus proceed from 2716 to 2704 to add additional normal patient training data sets. In another example, interim data sets from the training phase, such as float arrays generated at 2706, may be stored for use in validation at 2716. In another example, the subroutine may be modified to identify multiple populations of interest in a data set or a combined data set, or to identify subpopulations of interest within an identified reference population. For example, a first reference population or subpopulation may be identified which corresponds to a first maturation stage within a cell lineage, a second reference population or subpopulation may be identified which corresponds to a second maturation stage within a cell lineage, etc. In another example, a first reference population may be identified which corresponds to all the maturation stages within a first cell lineage (e.g., B lymphoid lineage cells) and a second reference population may be identified which corresponds to all the maturation stages within a second cell lineage (e.g., monocyte lineage cells), etc.

SVMs are trained in a two-class setting. To identify multiple reference populations, multiple SVMs may be employed. For example, to identify B-lymphoid cells and uncommitted progentor cells, two individual SVMs may be employed, and then merged. In another example, a primary SVM may be trained to identify all B-lymphoid (CD19+) cells, and then several secondary SVMs may be trained to identify stages of these B-lymphoid cells (stage 1-4) within the B-lymphoid (CD19+) cells.

In studies, SVM generated multidimensional boundary definitions have been created for B lymphoid lineage cells and other cell lineages (e.g., monocyte, lymphocyte, erythroid, neutrophil, dendritic, eosinophil, basophil, NK cell lineages, plasma cell and mast cell lineages). Studies are planned for T-cell subsets. The identified reference cell populations and subpopulations may be used, for example, to identify clusters of normal cells (data points) which are used to define a centroid line for clusters of a normal set of clusters (e.g., Subroutine 500 of FIGS. 18A-18C may be modified to start with clusters identified by the subroutine 2000 provided at 528 in FIG. 18B, with the subroutine 500 proceeding to identify a centroid line for each cluster, and then to define a normal centroid line and radius for the set of clusters, based on reference populations identified using the subroutine 2000; subroutine 600 of FIG. 19 may be modified to identify reference points at 604 based on reference populations or subpopulations identified by the subroutine 2000; subroutine 800 of FIG. 21 may be modified to identify reference points based on reference populations or subpopulations identified by the subroutine 2000; etc.), in vector normalization (as discussed below). The defined multidimensional decision boundaries may be used, for example, to classify cells in a test set of cells (e.g., subroutine 900 of FIG. 22 may be modified to apply a multidimensional decision boundary defined by the subroutine 2000 at step 910 to determine whether a point in a retrieved data set (e.g., a test patient data set) is in a cluster; etc.). SVMs may also be employed to measure quality control for the system. For example, mature lymphocytes are stable and generally unaffected by chemotherapy in patients with acute myeloid leukemia. The identification of the lymphocytes and computations of characteristics of the lymphocytes can provide an indication of whether the instrument is properly set up. For each patient, the reference population can be used for quality control. If the reference populations for normal require too much normalization (e.g., if the normalization vector, as described below, is too large), the data set can be flagged, which may indicate a problem for the entire data set. If multiple individual data sets are flagged, this may suggest a problem with the instrument.

Vector Normalization of Antigen Intensities

Embodiments have been described above in which the radius around the centroid line captures how far normal cells sit from the centroid line. The radius captures a biological variation component, which may be due to surface antigens being expressed in variable amounts, and thus the distance from a normal cell to the centroid line varies. The radius also captures a technical variation in analysis component, which may be due to, for example, different settings and tolerances in instrumentation, different shipments of antibodies, etc. In an embodiment, vector normalization is employed to account for and reduce the technical and fluidic variation, facilitating defining a tighter and more specific radius around the centroid line which more accurately represents the biological variation component, and which facilitates making the identification of abnormal cells easier and more accurate, as well as facilitating focusing on a specific set of abnormal cells, etc.

In flow cytometry, the intensities of markers are dependent on the position of the cell as it traverses the laser beam. If the cell trajectory is slightly off center, the cell will have a lower reading than if the cell were in the middle of the laser beam. The clusters may broaden when the flow rate is increased because of where the cell flows relative to the laser.

In an embodiment of a vector normalization process, a standard reference mean is determined for a set of normal patients. The standard reference mean is an average multidimensional intensity of a population for the set of normal patients. Then the intensities of cells of a new patient are normalized to the standard reference mean. SVMs may be used to identify cell populations of interest in both the determination of the standard reference mean and in the normalization of the intensities of the cells of the new patient.

Figure 29:
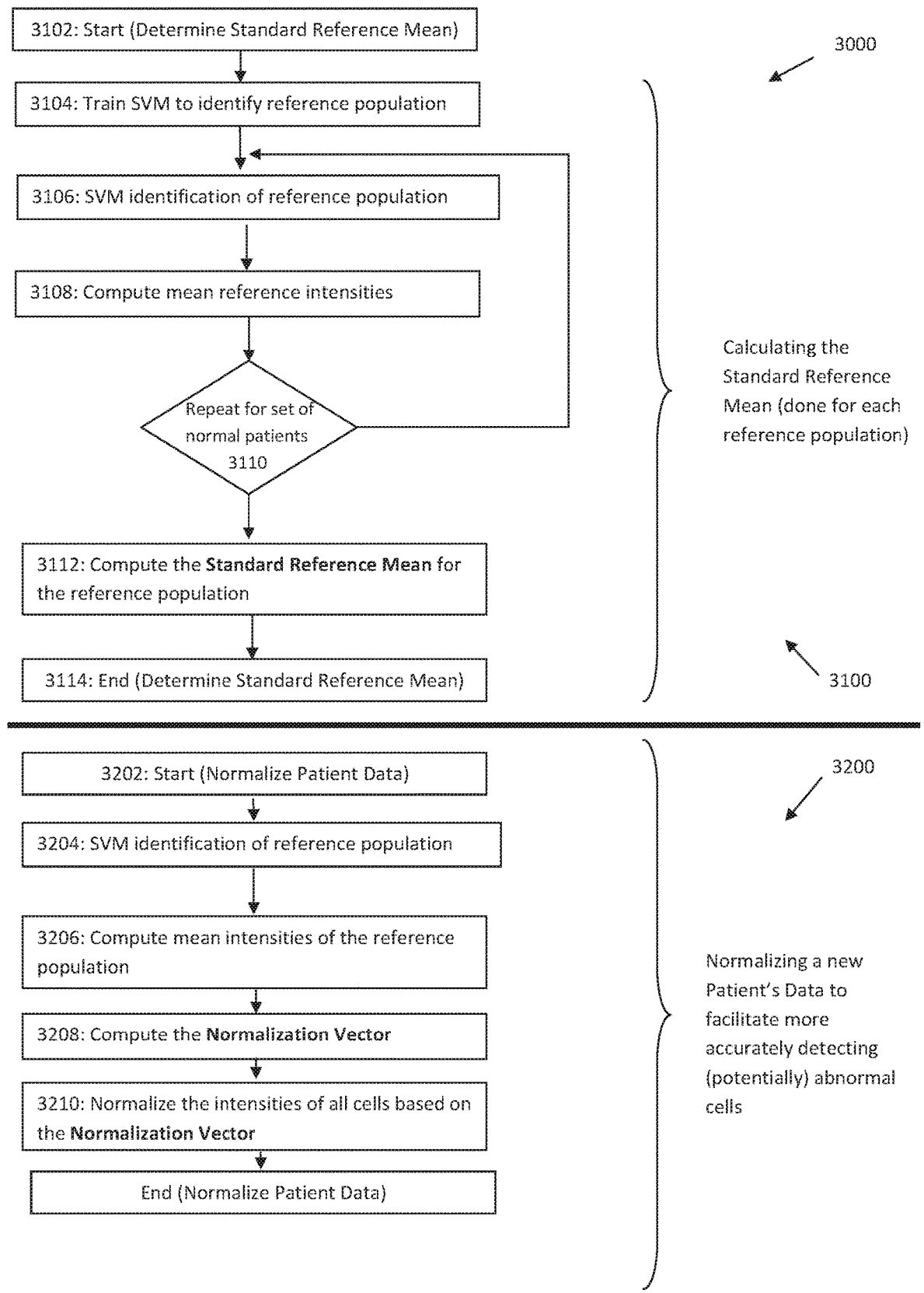
FIG. 29 is a flow chart illustrating operation of a system to determine a standard reference mean and to normalize patient data in a test set of data.

FIG. 29 is a flow diagram of an example vector normalization subroutine 3000 that may be employed by a diagnostic system, such as the diagnostic system 104 of FIG. 1, to normalize a cell population of a test set of cells. For convenience, the subroutine 3000 will be discussed with reference to FIGS. 29-39, and to the diagnostic system 104 of FIG. 1. As illustrated, the subroutine 3000 performs calculations in a log space instead of a linear space.

The subroutine 3000 includes a first phase 3100 to determine a standard reference mean and a second phase 3200 to normalize the cells of a new patient to the determined standard reference mean.

The first phase 3100 of the subroutine 3000 starts at 3102 and proceeds to 3104, where an SVM is trained to identify a reference population. For example, the training phase 2700 of the subroutine 2000 may be employed. A user selects a population of cells to use as a reference for subsequent data normalization, and defines a multidimensional boundary identifying the population of interest (see, e.g., FIG. 27, 2704 through 2718). The selection process (e.g., FIG. 27, 2704) may be based on biological knowledge, such as knowledge that certain populations of cells may present different advantages in intensity normalization. For example, lymphocytes may be easily identifiable in specimens and may be used to precisely normalize CD45 intensity; monocytes may be slightly more challenging to identify, but may be used to more accurately normalize CD33 intensity, which is more variable from person-to-person, etc. The variability of CD33 intensity is a result of a specific single nucleotide polymorphism (difference) in the DNA, called a SNP. Normalization of a reference population identified using a SVM may be employed to reduce the generic variability in CD33 intensity. Depending on what types of cells the user would like to assess (e.g., for leukemia), the user may choose a different reference population in which to normalize the data. In a study, 6 dimensions were employed in the selection process.

Figure 30:
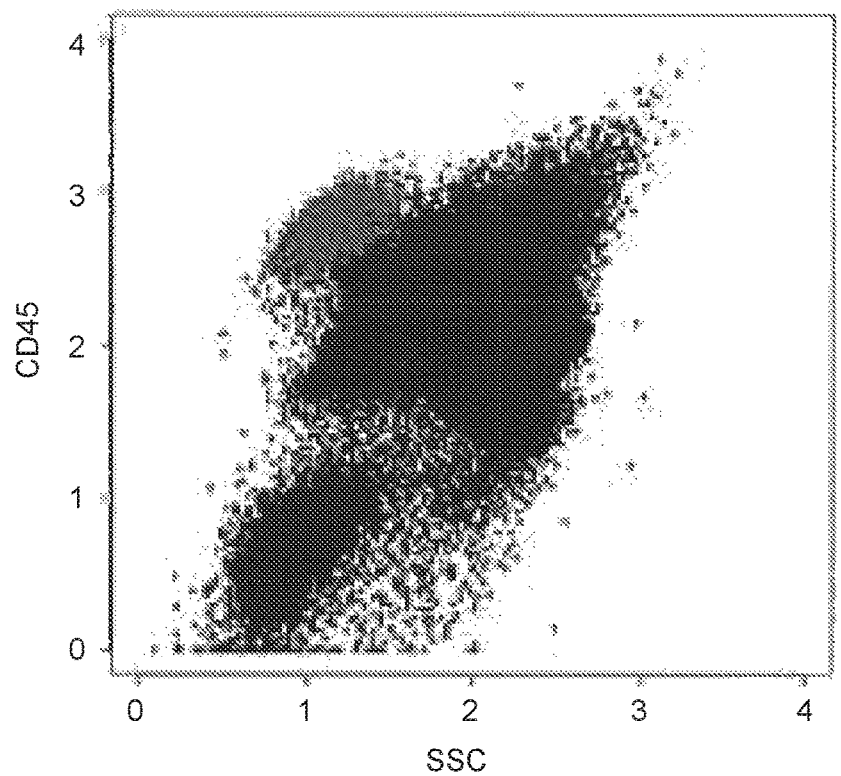
FIGS. 30-33 are illustrations of multi-dimensional data projected into a pseudo three-dimensional display generated by a system, such as the system illustrated in FIG. 1.

The subroutine 3000 proceeds from 3104 to 3106. At 3106, the multidimensional boundary is applied to identify the reference population of interest in a known normal patient. The diagnostic system 104 may employ, for example, an embodiment of the implementation phase 2730 of the subroutine 2000 of FIG. 28 applied to a known normal patient. FIG. 30 illustrates an example lymphocyte population of interest in purple with respect to SSC and CD45 parameter intensity. A reference population of interest may comprise hundreds of thousands of cells or relatively few cells (e.g., uncommitted progenitor cells). Illustrations of a population of interest with respect to other intensities (for example, other pairings of the 6 parameters employed) are omitted for ease of illustration. The subroutine 3000 proceeds from 3106 to 3108.

Figure 31:
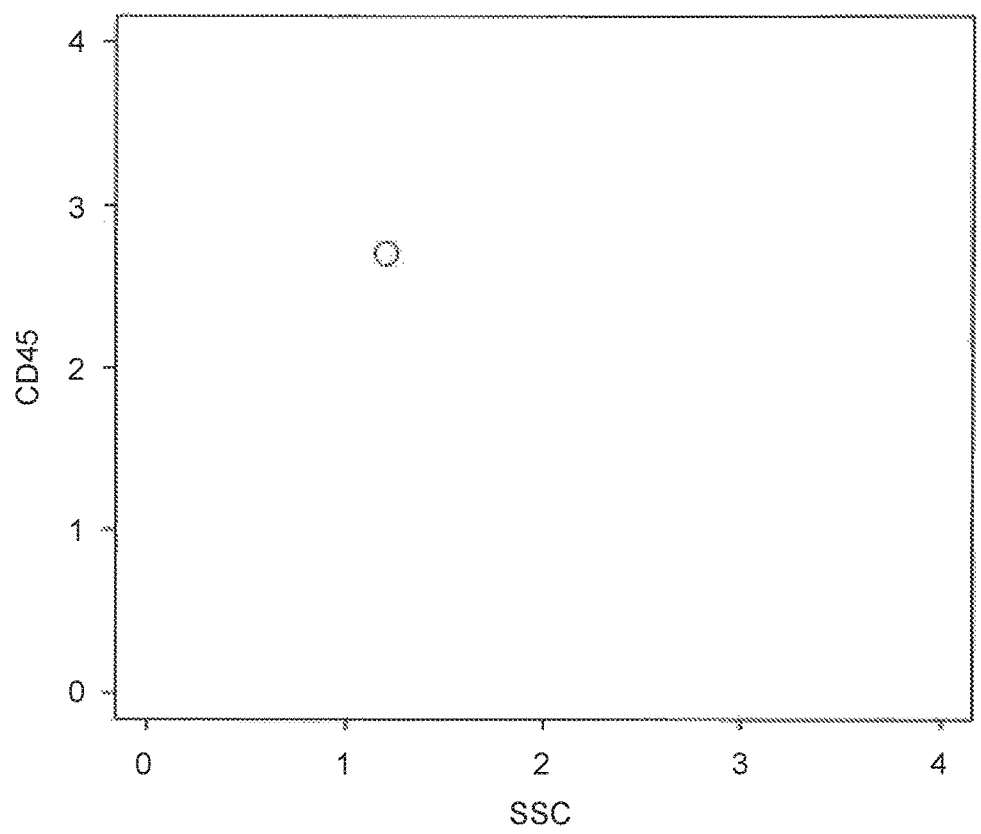

At 3108, the mean intensity of each parameter in the reference population in the known normal patient is computed by adding the intensities of the cells of the population of interest for a given parameter and dividing by the total number of cells identified in the population of interest. FIG. 31 illustrates an example graphing of a mean intensity of a lymphocyte population of interest for a single normal patient in a study with respect to SSC and CD45 parameter intensity as a purple dot. Illustrations of a mean intensity of a population of interest with respect to other intensities pairs or in multiple dimensions (for example, as described, in a study 6 parameters are employed) are omitted for ease of illustration. The mean intensity is computed for each of the 6 parameters. The mean reference intensities for the normal patient for each of the six parameters are stored.

Figure 32:
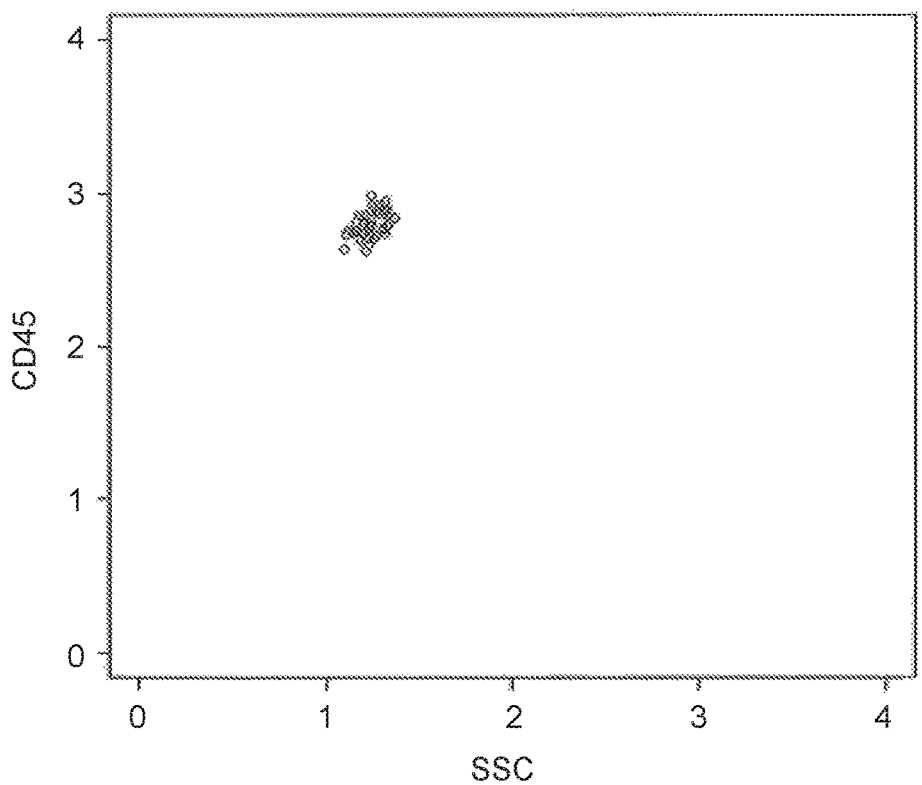

At 3110, the diagnostic system determines whether there are additional normal patient data sets to be processed. When it is determined at 3110 that there are additional normal patient data sets to be processed, the subroutine returns to 3106 to process the normal patient data set. When it is not determined at 3110 that there are additional normal patient data sets to be processed, the subroutine proceeds to 3112. FIG. 32 illustrates the example mean intensities for 27 normal patient data sets with respect to SSC and CD45 parameter intensity in a study, with the respective intensities illustrated as purple dots. Illustrations of mean intensities for the 27 normal patient data sets with respect to other intensities pairs or in other dimensions (for example, as described 6 parameters are employed) are omitted for ease of illustration.

Figure 33:
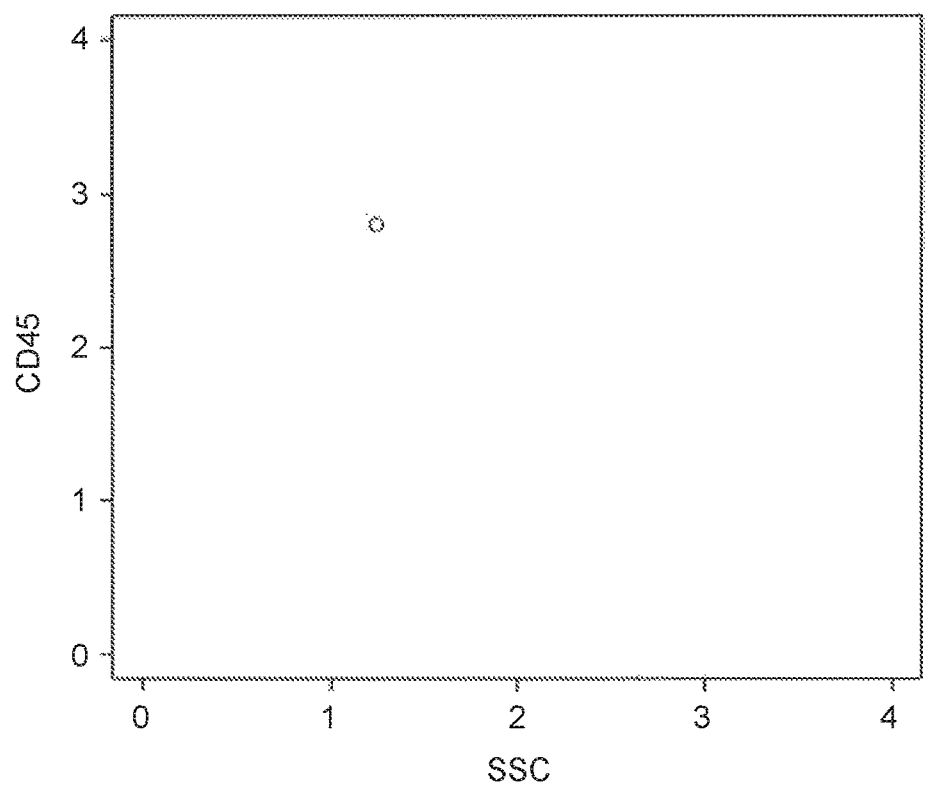
Figures 34, 35:
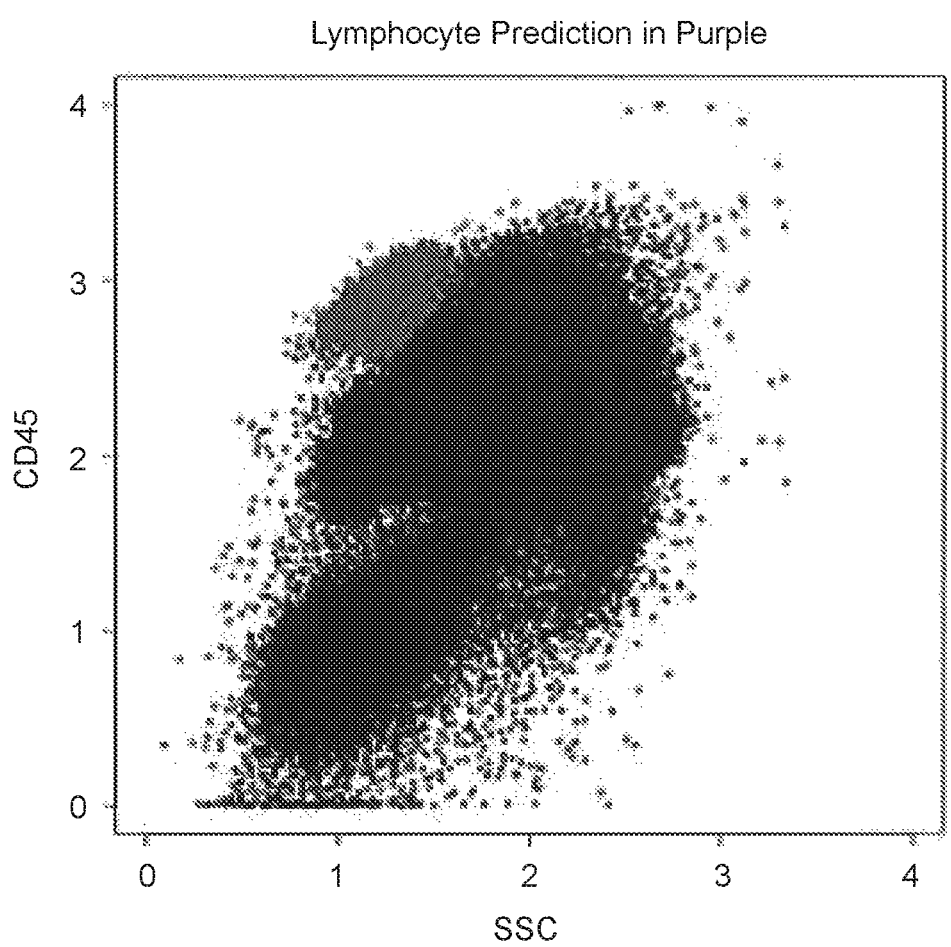
FIG. 34 illustrates a representation of a standard reference mean vector in an n-dimensional space.
FIGS. 35 and 36 are illustrations of multi-dimensional data projected into a pseudo three-dimensional display generated by a system, such as the system illustrated in FIG. 1.

At 3112, a standard reference mean is computed for the normal reference population. The standard reference mean is a mean of all the mean reference intensities for each parameter for the normal patient data sets. FIG. 33 illustrates a standard reference mean with respect to SSC and CD45 parameter intensity in the study as a purple dot. Illustrations of the standard reference mean with respect to other intensities pairs or in other dimensions are omitted for ease of illustration. In the study, the standard reference mean is a vector with 6 parameters, as shown in FIG. 34. As illustrated, the results are rounded.

The first phase process may be repeated to compute a standard reference mean intensity vector for each desired reference population (e.g., monocyte, erythroid, lymphoid, uncommitted progenitor cells, neutrophil, promyelocytes, etc.), and ends at 3114. In the study, the first phase process was performed for lymphoid lineage cells and other cell lineages, including monocyte, uncommitted progenitor cells, neutrophil, and promyelocytes lineages.

The second phase 3200 of the subroutine 3000 starts at 3202 and proceeds to 3204. At 3204, a reference population is selected based on biological knowledge (e.g., one of the reference populations for which a standard reference mean intensity was determined in the first phase is selected) and a corresponding multidimensional boundary (e.g., a boundary determined at 3104) is applied to identify a reference population of interest for a test patient. The number of cells in the reference population of interest may number in the hundreds of thousands or more, or relatively few cells (e.g., uncommitted progenitor cells, mast cells, plasmacytic dendritic cells). The diagnostic system 104 may employ, for example, an embodiment of the implementation phase 2730 of the subroutine 2000 of FIG. 28. FIG. 35 illustrates an example lymphocyte population of interest in the study in purple with respect to SSC and CD45 parameter intensity. Illustrations of a population of interest with respect to other intensities (for example, other pairings of the 6 parameters employed) are omitted for ease of illustration. The subroutine 3000 proceeds from 3204 to 3206.

Figures 36, 37, 38:
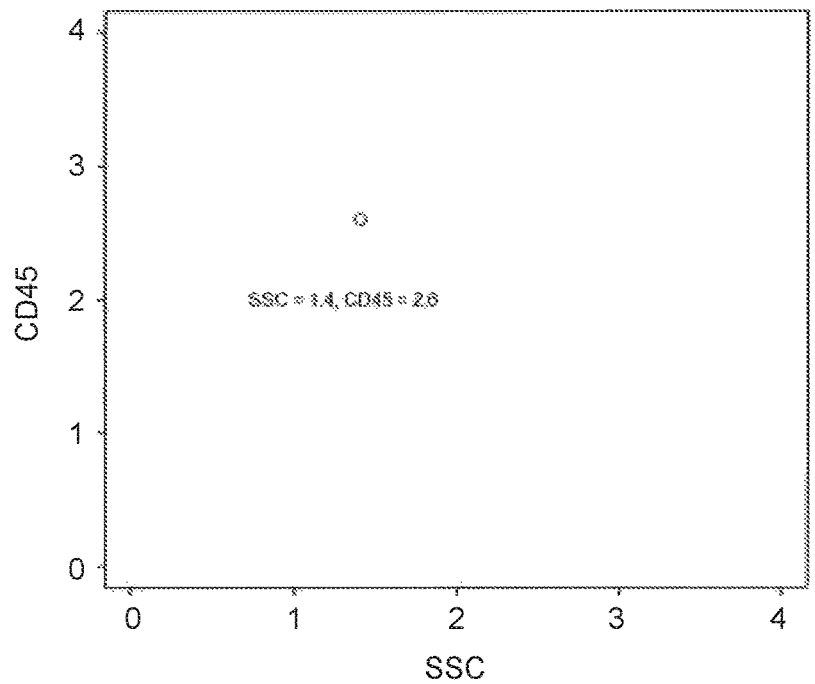
FIG. 37 illustrates a representation of a mean intensity vector of a test patient data set in an n-dimensional space.
FIG. 38 illustrates a representation of a normalization vector of a test patient data set in an n-dimensional space.

At 3206, the mean intensity of each parameter in the reference population for the test patient is computed by adding the intensities of the cells of the population of interest for a given parameter and dividing by the total number of cells identified in the population of interest of the test patient. FIG. 36 illustrates an example graphing of a mean intensity of a lymphocyte population of interest for a test patient with respect to SSC and CD45 parameter intensity in the study as a purple dot. Illustrations of a mean intensity of a population of interest with respect to other intensities pairs or in multiple dimensions (for example, as illustrated 6 parameters are employed) are omitted for ease of illustration. The mean intensity is computed for each of the 6 parameters. In the study, the result was a vector with 6 parameters, each corresponding to the mean for a respective parameter of the population of interest, as illustrated in FIG. 37. The results as shown are rounded.

The subroutine 3000 proceeds from 3206 to 3208. At 3208, the normalization vector for the patient is calculated by determining a difference between the mean parameter intensities for the patient and the standard reference mean determined in the first phase 3100. The resulting normalization vector for the patient from the study is shown in the last column of FIG. 38. As illustrated, the mean parameter intensities for the patient were subtracted from the standard reference mean.

Figure 39A:
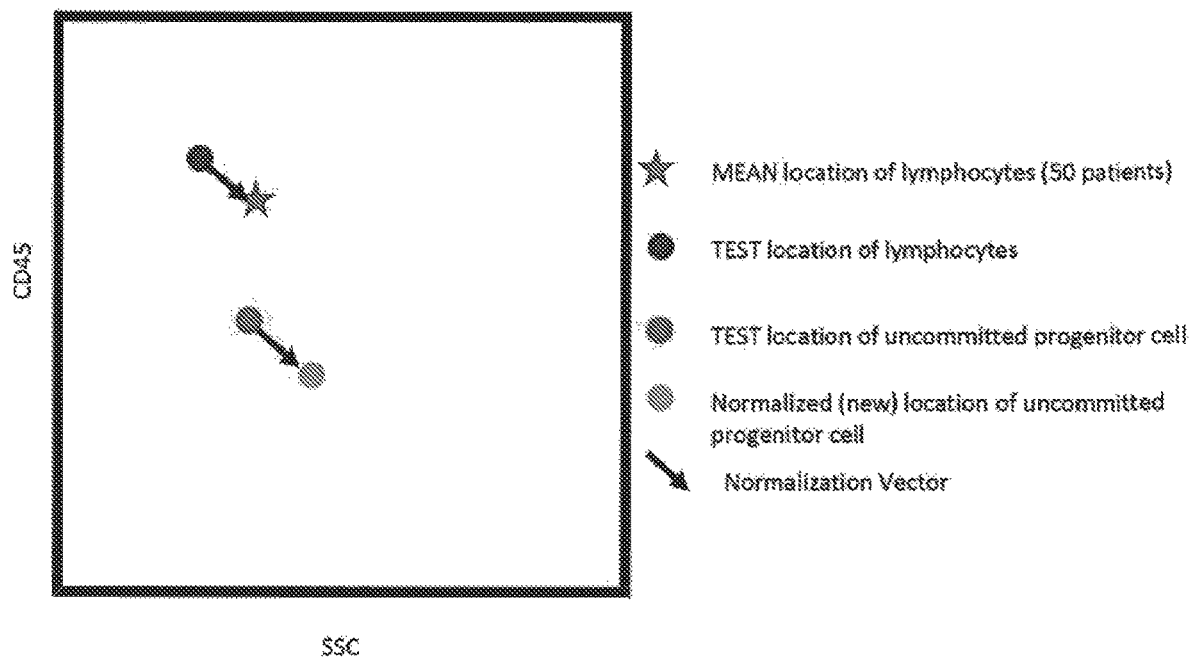
FIG. 39A is a graphic illustration of an example application of a normalization vector to cells of a data set.

The subroutine 3000 proceeds from 3208 to 3210. At 3210, the normalization vector for the patient calculated at 3208 is used to normalize the intensities of each of the cells of the test patient. In an embodiment, the normalization vector may be used to normalize selected cells of the test patient, such as cells of an identified reference population. FIG. 39 illustrates the application of the normalization vector to a first cell of the test patient. As illustrated, the normalization vector is added to the unnormalized intensity of the cell. Examples of application of a normalization vector to various cells of a data set are graphically illustrated in FIG. 39A. The normalized intensities for the test patient may be plotted, visualized and assessed for disease. For example, the normalized cells for the test patient may be compared to a centroid line and radius defining a normal population of cells to diagnose cancer, such as residual cancer. For example, subroutine 900 of FIG. 22 may be modified to normalize a reference population of a retrieved data set using subroutine 3000 of FIG. 29 before classifying the cells (data points) of the retrieved data set. When a test patient data set of a patient having residual disease is normalized, both the normal cells and the tumor cells would typically be normalized.

Some embodiments of a system 100 may perform other acts not shown in FIG. 29, may not perform all of the acts shown in FIG. 29, or may perform the acts of FIG. 29 in different orders. For example, the subroutine 3000 may be modified in some embodiments to determine the difference between the mean parameter intensities for the patient and the standard reference mean by subtracting the standard reference mean from the mean parameter intensities for the patient, and to determine the normalized intensity of a cell by subtracting the normalization vector from the unnormalized intensities of the cell. In another example, other or additional normal cluster configurations may be defined and modeled for use in determining standard reference means and mean parameter intensities. For example, in a study, a first set of tubes of normal patient cells was subjected to a first protocol generating first normal patient data sets with parameters for FSC, SSC, CD20 (FITC), CD10 (PE), CD45 and CD19 (which may correspond to, for example, ten clusters), and a second set of tubes of normal patient cells was subjected to a second protocol generating second normal data sets with parameters for FSC, SSC, CD22 (FITC), CD34 (PE), CD45 and CD19 (which may correspond to, for example, four clusters). Other protocols and cluster configurations may be employed. The selected protocol(s) may then be applied to set(s) of cells of a test patient to generate test patient data set(s).

Radius Definition

As discussed above, a normal radius around the centroid line may be defined using statistical algorithms. See, e.g., FIGS. 18A-18C and the discussion thereof. A dimension of a multidimensional radius may be statistically characterized for each parameter measured by the flow cytometry. These statistical characterizations may be employed in data visualizations represented in images (e.g. linear, subtraction-of-normalized, etc.). In a series of studies, 25 or more sets of cells of normal patients were used to mathematically characterize how far away normal B-cells sit from the defined centroid line in each dimension of the radius for each cluster. The larger the number of sets of cells of normal patients, the greater the statistical confidence in the definition of the normal data set. The variation was then normalized in the form of a z-score, which may also be referred to as a chi-squared analysis.

After the normal centroid line is defined for a series of normal patients (See, e.g., FIGS. 18A-18B and the description thereof), a radius for the normal set of data may be statistically characterized.

Figure 40:
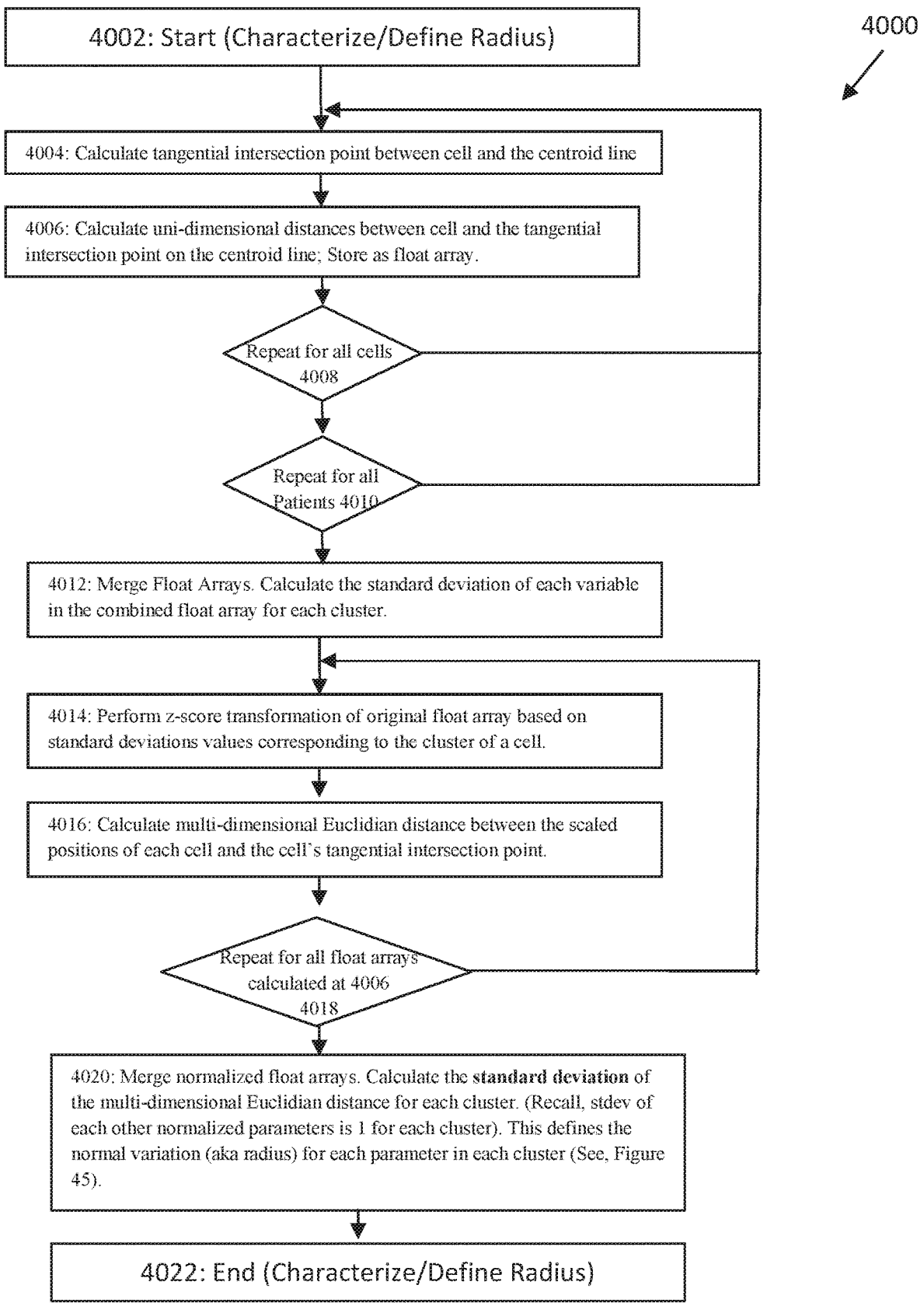
FIG. 40 is a flow chart illustrating operation of a system to characterize a radius of a normal patient data set by a system, such as the system illustrated in FIG. 1.

FIG. 40 is a flow diagram of an example radius characterization subroutine 4000 that may be employed by a diagnostic system, such as the diagnostic system 104 of FIG. 1, to characterize a radius, which defines, together with a normal centroid line, a set of normal clusters in an n-dimensional space. In a study, six parameters were used to define a set of normal clusters for a B-cell lineage. For convenience, the subroutine 4000 will be discussed with reference to FIGS. 40-45, and to the diagnostic system 104 of FIG. 1. Radius characterization of a data set is predicated by two steps. First, cells belonging to the lineage for which the radius will be characterized are selected from the dataset. An expert may manually identify cells belonging to a lineage. Alternatively SVMs may be employed to identify cells belonging to a lineage, as demonstrated above in subroutine 2732 (FIG. 28). Second, each cell in the lineage is clustered to the nearest corresponding reference point. This may be accomplished, for example, using the process of act 1006 of subroutine 1000 (FIG. 24), or a similar process. In other examples, flow diagrams of embodiments of a clustering processes are illustrated in FIGS. 18A to 18C and FIG. 40A.

Figure 41:
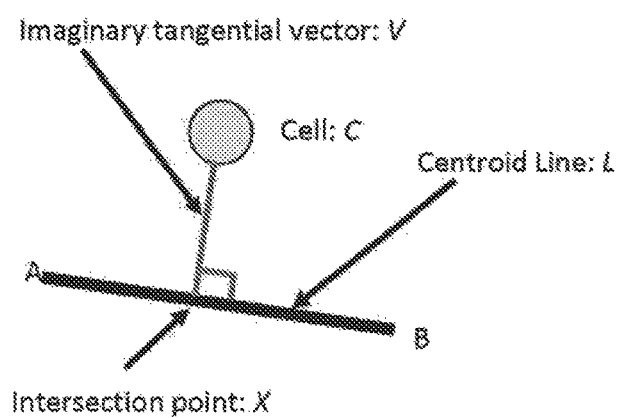
FIG. 41 is an illustration of a tangential intersection point between a cell (data point) of a data set and a centroid line defining a set of normal clusters.
Figure 41A:
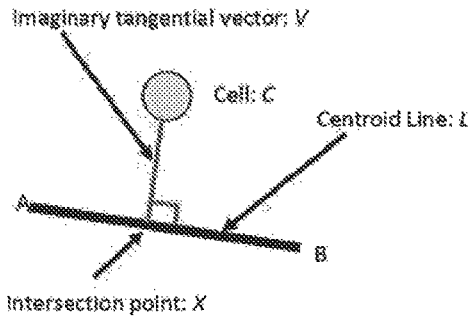
FIG. 41A is an illustration of an example calculation of a tangential intersection point.

After cells belonging to a lineage are identified and clustered to a reference point, the subroutine 4000 starts at 4002 and proceeds to 4004. At 4004, a tangential intersection point between a cell of a normal patient data set and the centroid line is identified on the centroid line. Identification of the tangential intersection points on the centroid line may be done using dot products. An illustration of an example tangential intersection point is shown in FIG. 41. An illustration of an example calculation of a tangential intersection point is shown in FIG. 41A. The centroid line may be separated into segments and candidate segments may be used to identify the tangential intersection point of a cell, which may reduce the number of calculations required.

In a study, there were 10 clusters of maturing B-lymphoid cells. The centroid line was broken into 9 segments: the first segment running from the center of cluster 1 to the center of cluster 2; the second segment running from the center of cluster 2 to the center of cluster 3; the third segment running from the center of cluster 3 to the center of cluster 4; the fourth segment running from the center of cluster 4 to the center of cluster 5; the fifth segment running from the center of cluster 5 to the center of cluster 6; the sixth segment running from the center of cluster 6 to the center of cluster 7; the seventh segment running from the center of cluster 7 to the center of cluster 8; the eighth segment running from the center of cluster 8 to the center of cluster 9; the ninth segment running from the center of cluster 9 to the center of cluster 10. A cell in the first cluster would have 1 candidate segment, the first segment; a cell in the second cluster would have 2 candidate segments, the first segment and the second segment; a cell in the third cluster would have two candidate segments, the second segment and the third segment; and so forth, with a cell in the tenth cluster having one candidate segment, the ninth segment. In the study, when there was no real tangential intersection between a cell and one of the candidate segments for the cell, the center of the cluster to which the cell belonged was considered to be the tangential intersection point for the cell.

Other segmentation schemes may be employed. For example, the centroid line for the 10 clusters of maturing B-lymphoid cells of the study may be broken into 10 segments roughly corresponding to the clusters, and the candidate segments for a cell may be defined as the segment of the cluster to which the cell belongs and the segments of adjacent clusters of the cluster to which the cell belongs.

The subroutine 4000 proceeds from 4004 to 4006. At 4006, the diagnostic system 104 calculates uni-dimensional distances between the cell and the identified tangential intersection point for the cell on the centroid line for each parameter. This may be done, for example, using Equation 2, set forth below:

$$\text{Parameter Distance} = \text{Parameter}_{Cell} - \text{Parameter}_{TCP} \quad \text{[Equation 2]}$$

where $\text{Parameter}_{Cell}$ is the value of a respective parameter for the cell and $\text{Parameter}_{TCP}$ is the value of the parameter for the tangential intersection point for the cell on the centroid line. The parameter distance values for the cell may be stored in a float array (see FIG. 42). The subroutine 4000 proceeds from 4006 to 4008. At 4008, the diagnostic system determines whether there are more cells to be processed for the normal patient. When it is determined at 4008 that there are more cells to be processed for the normal patient, the subroutine returns to 4004 to process the next cell. When it is not determined at 4008 that there are more cells to be processed for the normal patient, the subroutine proceeds to 4010. FIG. 42 illustrates an example of a float array storing parameter distances for six parameters for a normal patient data set, with each row corresponding to a cell of the patient and each column corresponding to a parameter.

At 4010, the diagnostic system 104 determines whether there are additional normal patient data sets to process. When it is determined at 4010 that there are additional normal patient data sets to process, the subroutine 4000 returns to 4004 to process the cells of the next normal patient data set. When it is not determined at 4010 that there are additional normal patient data sets to process, the subroutine 4000 proceeds to 4012.

At 4012, the means and standard deviation of the distance between the cell and the cell's intersection point is determined for each parameter in each cluster for a combined normal patient data set. The clusters may be identified, for example, using act 1006 of subroutine 1000 of FIG. 24, the clustering process of FIGS. 18A-18C, the clustering process of FIG. 40A (described below), etc. The combined normal patient data set may be, for example, a combined float array for the normal patient data sets generated by merging the float arrays of the individual data sets. The means and standard deviation of the distance between the cell and the cell's intersection point for each parameter in each cluster in the combined float array may be determined and stored using the combined float array. FIG. 43 illustrates an example float array storing the determined standard deviations. FIG. 43A illustrates an example float array storing the determined mean distances between the cell and the cell's tangential intersection point.

The subroutine 4000 proceeds from 4012 to 4014, where the diagnostic system 104 performs a z-score transformation for each normal patient data set based on the standard deviations. This may be done using a float array for a normal patient data set generated at 4006 based on the standard deviations determined at 4012. The standard deviation is used to standardize distances in a test patient's float array with a z-score transformation. Different parameters measured by the flow cytometer have different amounts of normal variation. For example, expression of the CD45 protein is incredible consistent (has a low variation) on B-lymphoid cells, while FSC (size) has high variation. Standardizing each column of the normal data set with a z-score transformation facilitates statistically comparing variations for different parameters, with a result that the standard deviation in each individual column by definition is equal to 1 (see FIG. 45, discussed below). (Rounding errors may result in minor deviations). By standardizing each column with a z-score transformation, the distance from each cell to the cell's tangential intersection point is standardized. The average distance of each cluster has a mean of zero and a standard deviation of one, so that a cell sitting one standardize unit away from the centroid line in the CD45 dimension is equally significant in a biological sense to a cell sitting one standardized unit away from the centroid line in the FSC dimension.

Figure 44:
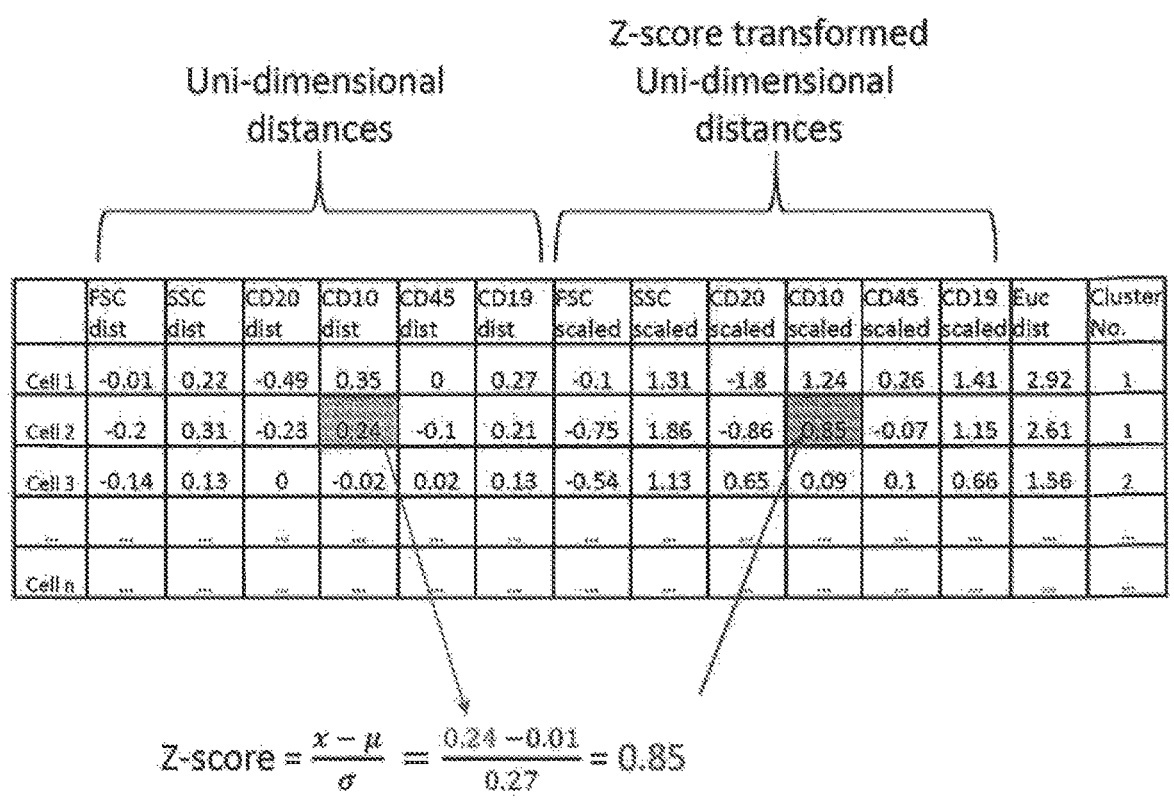
FIG. 44 is an illustration, in the form of a float array, of a standardized normal patient data set.

The subroutine 4000 proceeds from 4014 to 4016. At 4016, the diagnostic system 104 determines the multidimensional Euclidean distance between the scaled positions of each cell and the centroid intersection point. This may be done, for example, using Equation 3, set forth below:

$$\text{Euclidean Distance} = \text{SQRT}(a^2 + b^2 + c^2 + d^2 + e^2 + f^2) \quad \text{Equation 3}$$

where a-f are the standardized distances from the cell to the centroid line determined at 4014. A standardized float array may be generated for the normal patient data set indicating the z-transformed distributions, with a column added for the Euclidean distances. FIG. 44 illustrates an example standardized float array for a normal patient data set. The euclidean distance calculation may be modified to weight distances between the cell and the cell's intersection point differently. The subroutine proceeds from 4016 to 4018.

At 4018, the diagnostic system 104 determines whether there are additional normal patient data sets to process. When it is determined at 4018 that there are additional normal patient data sets to process, the subroutine 4000 returns to 4014 to process the cells of the next normal patient data set. When it is not determined at 4018 that there are additional normal patient data sets to process, the subroutine 4000 proceeds to 4020.

At 4020, the standardized float arrays are merged and the mean and standard deviation are calculated for the standardized Euclidean distance for each cluster. An example (standard deviation) merged and standardized floating array for a normal data set is illustrated in FIG. 45. As the individual parameter distances have been standardized, the standard deviations are equal to 1. The values in FIG. 45 represent the individual component dimensions of radius for the normal data sets, as well as the multi-dimensional Euclidean distance radii. It is noted that the values for the last column may not be equal to the square root of the sum of the squared individual parameters, and may change within each cluster. An example (mean) standardized float array for a normal dataset is illustrated in FIG. 45A. The individual parameter distances have been standardized, and the means of each individual parameter are equal to 0. It is noted that the values for the last column may not be equal to the square root of the sum of the squared individual parameters. The subroutine 4000 proceeds from 4020 to 4022, where the subroutine ends.

Some embodiments of a system 100 may perform other acts not shown in FIG. 40, may not perform all of the acts shown in FIG. 40, or may perform the acts of FIG. 40 in different orders. For example, the subroutine 4000 may be modified in some embodiments to generate a float array at 4020 which omits the individual component dimensions of radius for the normal data sets. In another example, other or additional normal cluster configurations may be defined and modeled. For example, a first set of tubes of normal patient cells may be subjected to a first protocol generating first normal patient data sets with parameters for FSC, SSC, CD20 (FITC), CD10 (PE), CD45 and CD19, (which may correspond to, for example, ten clusters), a second set of tubes of normal patient cells may be subjected to a second protocol generating second normal data sets with parameters for FSC, SSC, CD22 (FITC), CD34 (PE), CD45 and CD 19 (which may correspond to, for example, four clusters), etc. The selected protocol(s) may be applied to set(s) of cells of a test patient to generate test patient data set(s).

It is noted that embodiments of subroutine 500 of FIGS. 18A-C may be modified to employ the subroutine 4000 of FIG. 40 at act 536 of FIG. 18C to define the radii of the defined set of normal clusters.

Figure 40A:
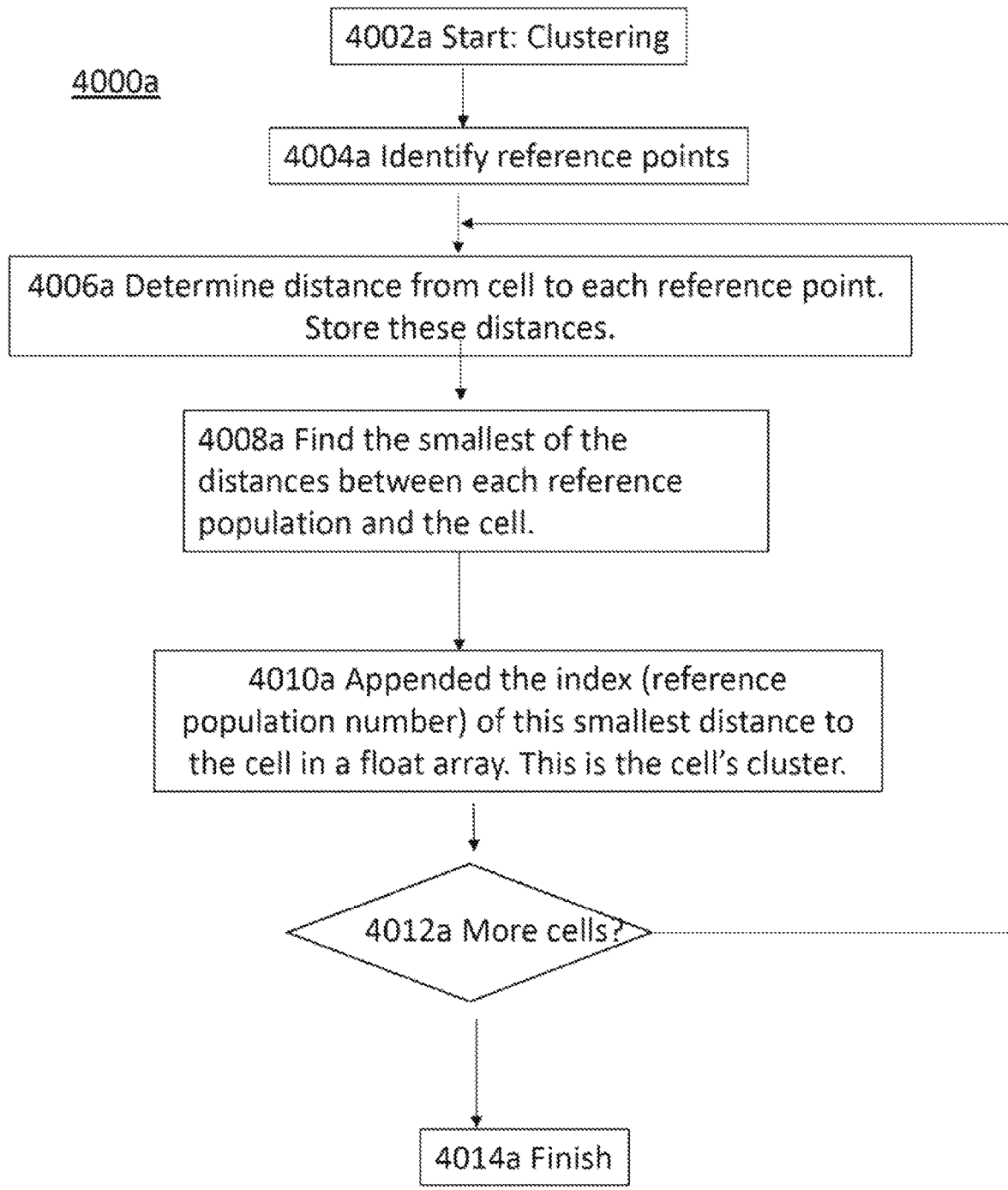
FIG. 40A is a flow diagram illustrating an embodiment of a cell clustering subroutine.

FIG. 40A is a flow diagram of an example clustering subroutine 4000a that may be employed by a diagnostic system, such as the diagnostic system 104 of FIG. 1, to cluster cells or data points of a test set of cells. The subroutine starts at 4002a and proceeds to 4004a. At 4004a, reference points are identified for reference populations, such as clusters in a normal set of cells. Table 4 below illustrates example reference points. The reference points may be, for example, cluster centroids or points selected after viewing representations of the data. Identification of reference points is discussed in more detail elsewhere herein.

TABLE 4

|  | FSC | SSC | CD20 | CD10 | CD45 | CD19 |
|---|---|---|---|---|---|---|
| Ref point 1 | 1.2 | 1.1 | 0.5 | 3.0 | 1.8 | 2.0 |
| Ref point 2 | 1.0 | 1.1 | 0.4 | 2.6 | 2.2 | 2.4 |
| ... | ... | ... | ... | ... | ... | ... |
| Ref point n | ... | ... | ... | ... | ... | ... |

The subroutine 4000a proceeds from act 4004a to act 4006a. At 4006a, the distances from the cell to each reference point are determined and stored. The distances may be determined using equation 4 below:

$$distance = \sqrt{(par.1_{cell} - par.1_{ref.point})^2 + ... + (par.n_{cell} - par.n_{ref.point})^2}$$ Equation 4 where par is the par.1 is the first parameter (e.g., CD45), par.2 is the second parameter, etc.

Table 5 illustrates example distances for a cell stored in a float array.

TABLE 5

|  | Ref point 1 distance | Ref point 1 distance | ... | Ref point n distance | Cluster |
|---|---|---|---|---|---|
| Cell 1 | 0.7 | 0.9 |  | 2.0 | 1 |

The subroutine 4000a proceeds from 4006a to 4008a. At 4008a, the subroutine 4000a identifies the smallest of the distances between the reference point associated with a reference population (e.g., a cluster) and the cell. The subroutine 4000a proceeds from 4008a to 4010a. At 4010a, an index corresponding to the reference population associated with the reference point which is the smallest distance from the cell is appended to a float array (see, e.g., FIG. 42). The subroutine 4000a proceeds from 4010a to 4012a, where it is determined whether there are more cells to process. When it is determined at act 4012a that there are more cells to process, the subroutine 4000a proceeds from 4012a to 4006a to process the next cell. When it is not determined at act 4012a that there are more cells to process, the subroutine 4000a proceeds from 4012a to 4014a, where the subroutine 4000a terminates.

Some embodiments of a system 100 may perform other acts not shown in FIG. 40A, may not perform all of the acts shown in FIG. 40A, or may perform the acts of FIG. 40A in different orders. For example, the subroutine 4000a may be modified in some embodiments to use data storage formats other than float arrays.

Identifying Cells (Percentages, etc.) Outside of the Normalized Radius in Test Patients In an embodiment, an image of a comparison of a test set of cells to a defined normal set of clusters is generated which facilitates quickly and intuitively communicating whether abnormal cell populations are present in a test set of cells using the diagnostic methods disclosed herein. The generated image is referred to herein as a summary plot and may comprise image pixels. The summary plot graphically summarizes cell frequency and position information for cells in each cluster/maturational stage. Current visual assessment of potential abnormalities is limited to analysis of a series of dot plots, which can only be understood by an expert in flow cytometry. An embodiment of a generated summary plot image facilitates interpretation by non-flow cytometry experts and quickly communicating what maturational stages of cells are abnormal, as discussed, for example, with respect to FIGS. 46-57 below. In an embodiment, potential abnormalities can be further investigated by subtracting cells within a normal radius away from the centroid line, as discussed, for example, with respect to FIGS. 58-65 below. This may facilitate the quick and specific identification of cells that differ greatly from the normal centroid.

Figure 46:
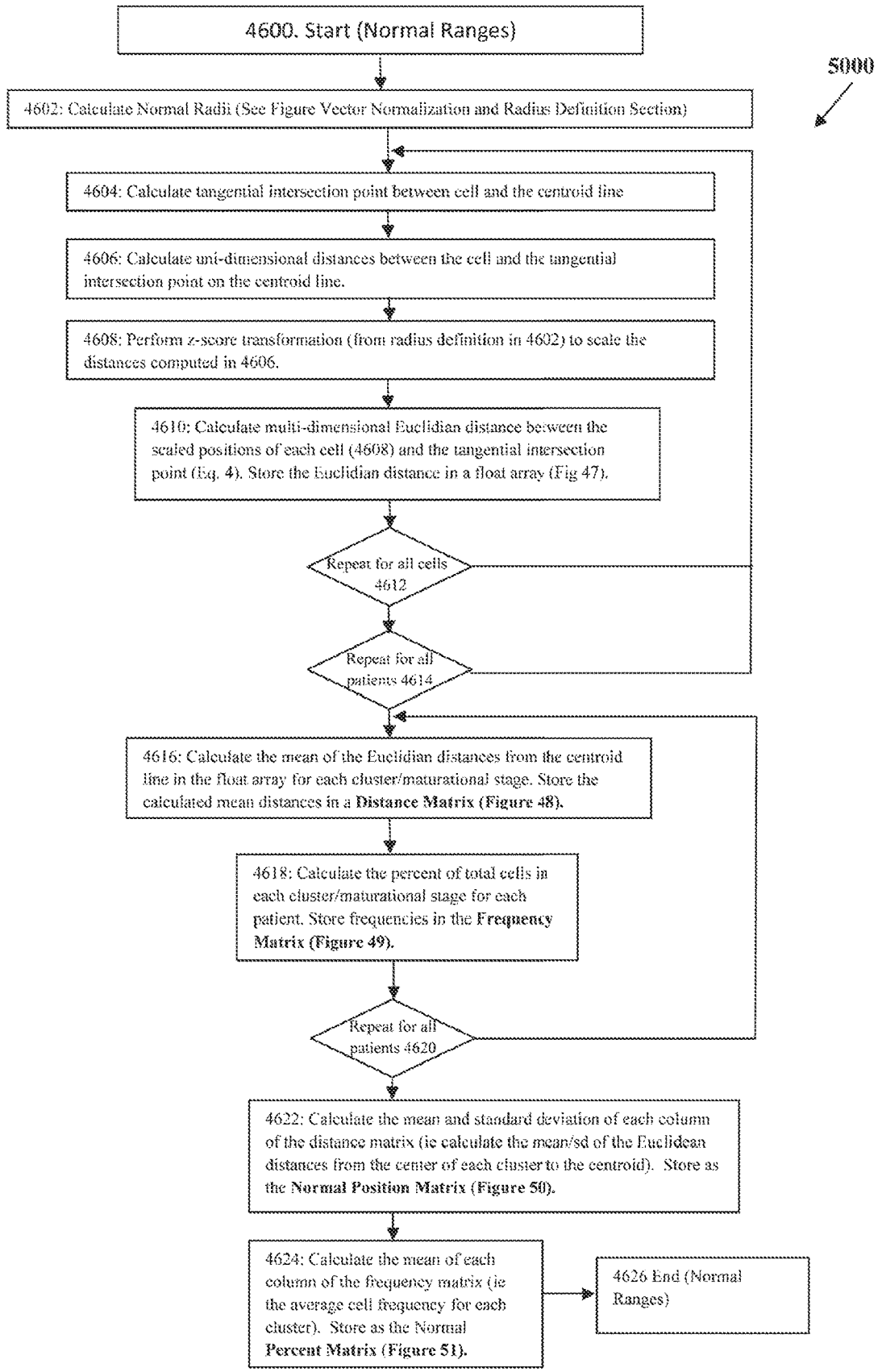
FIG. 46 is a flow chart illustrating operation of a system to characterize a normal distance between cells (data points) of a set of normal cells in a cluster and a centroid line, as well as normal cell (data point) frequency breakdown, by a system, such as the system illustrated in FIG. 1.

FIG. 46 is a flow diagram of an example subroutine 5000 that may be employed by a diagnostic system, such as the diagnostic system 104 of FIG. 1, to define a normal range of how far each cluster/maturation stage of normal cells is from the centroid line, and a normal cell frequency breakdown of the proportion of cell that are in each cluster/maturation stage. These definitions may then be used as a reference in which to compare a set of cells of a test patient to a definition of a normal set of clusters/maturation stages. For convenience, the subroutine 5000 will be discussed with reference to FIGS. 46-51, and to the diagnostic system 104 of FIG. 1.

The subroutine 5000 starts at 4600 and proceeds to 4602. At 4602, normal radii are obtained or determined by the diagnostic system 104. For example, stored normal radii may be retrieved, or normal radii may be determined, for example, as described above with reference to subroutine 4000 and FIGS. 40-45. Once the normal radii for clusters of a normal cell lineage are determined, this information may be stored for future use. Additionally, cells in a normal dataset are clustered to reference points (see, e.g., act 1006 of subroutine 1000, FIG. 24A, FIG. 40A). The subroutine 5000 proceeds from 4602 to 4604.

At 4604, a tangential intersection point between a cell of a normal patient data set and the centroid line is identified on the centroid line. Identification of the tangential intersection points on the centroid line may be done using dot products. See the discussion of determining tangential intersection points as discussed above with respect to FIGS. 40 and 41. As discussed above, the centroid line may be separated into segments and candidate segments may be used to identify the tangential intersection point of a cell, which may reduce the number of calculations required.

The subroutine 5000 proceeds from 4604 to 4606. At 4606, the diagnostic system 104 calculates uni-dimensional distances between the cell and the identified tangential intersection point for the cell on the centroid line. This may be done, for example, using Equation 2, set forth above and repeated below for convenience:

$$\text{Parameter Distance} = \text{Parameter}_{Cell} - \text{Parameter}_{TCP} \quad [\text{Equation 2}]$$

where $\text{Parameter}_{Cell}$ is the value of a respective parameter for the cell and $\text{Parameter}_{TCP}$ is the value of the parameter for the tangential intersection point for the cell on the centroid line. The parameter distance values for the cell may be stored in a float array (see, e.g., uni-dimensional distances in FIG. 47). The subroutine 5000 proceeds from 4606 to 4608.

At 4608, the diagnostic system 104 performs a z-score transformation on a float array for a normal patient data set (e.g., a data set generated at 4006) based on the radii definition retrieved or determined at 4602.

The subroutine 5000 proceeds from 4608 to 4610. At 4610, the diagnostic system 104 determines the multidimensional Euclidean distance between the scaled positions of each cell (4608) and the centroid intersection point. This may be done, for example, using Equation 5, set forth below:

$$\text{Euclidean Distance} = \text{SQRT}(a^2 + b^2 + c^2 + d^2 + e^2 + f^2) \quad \text{Equation 5}$$

where a-f are the standardized distances from the cell to the centroid line determined at 4608. A standardized float array may be generated storing the Euclidean distance for the normal patient data set indicating the z-transformed distributions. The subroutine proceeds from 4610 to 4612.

At 4612, the diagnostic system 104 determines whether there are additional cells in the normal data set to process. When it is determined at 4612 that there are additional cells in the normal data set to process, the subroutine 5000 returns to 4604 to process the next cell. FIG. 47 illustrates an example float array for a normal patient including a column for the Euclidean distances and for the cluster number. When it is not determined at 4612 that there are additional cells to process, the subroutine proceeds to 4614.

At 4614, the diagnostic system 104 determines whether there are additional normal patient data sets to process. When it is determined at 4614 that there are additional normal patient data sets to process, the subroutine 5000 returns to 4604 to process the cells of the next normal patient data set. Individual float arrays (see FIG. 47) for the cells of the respective normal patient data sets may be stored. When it is not determined at 4614 that there are additional normal patient data sets to process, the subroutine 5000 proceeds to 4616.

At 4616, the mean Euclidean distance from the centroid line is calculated for each of the clusters/maturation stages for each normal patient. For example, with reference to FIG. 47, a mean distance for each cluster for a patient may be determined with respect to the mean Euclidean Distance column of FIG. 47. The calculated mean values may be stored in a distance matrix. FIG. 48 illustrates an example distance matrix, with each row corresponding to a patient in the set of normal patients in a study, each column corresponding to a cluster, and each value corresponding to the average Euclidian distance of cells in that cluster from the centroid line. Other mean distances may be determined, instead of or in addition to a mean Euclidean distance from the centroid line. For example, a mean distance from the centroid line for each cluster for each patient may be determined with respect to other individual parameters, such as CD10 (PE) or any combinations of the parameters of the float array (e.g., FSC, SSC, CD20 (FITC), CD45, CD34, etc.).

The subroutine 5000 proceeds from 4616 to 4618. At 4618 a percentage of cells belonging to each cluster for each normal patient is calculated. For example, the percentage of patient cells in a cluster for a normal patient may be determined by dividing the number of patient cells in the patient data set which are in the cluster by the total number of patient cells in the patient data set, and multiplying the result by 100. Some embodiments may determine the proportion of cells of a patient data set in a cluster to a total number of cells in the patient data set in other manners, such as determining a ratio instead of a percentage. The percentages may be stored in a frequency matrix, as illustrated using data from the study in FIG. 49. In theory, each row of FIG. 49 should add up to one-hundred percent. However, rounded values may be used in some embodiments, which may introduce minor rounding errors. The subroutine 5000 proceeds from 4618 to 4620.

At 4620, the diagnostic system 104 determines whether there are additional normal patient data sets to be processed. When it is determined at 4620 that there are additional normal patient data sets to be processed, the subroutine 5000 returns to 4616 to process the next patient data set in the set of normal patient data sets. When it is not determined at 4620 that there are additional normal patient data sets to be processed, the subroutine 5000 proceeds to 4622.

At 4622, the diagnostic system 104 determines the mean and standard deviation of the mean Euclidean distances determined at 4616 for each cluster. In other words, the mean Euclidean distance each cluster sits from the centroid line and the variation of this mean Euclidean distance is determined for a set of normal patients. This may be done by, for example and with reference to FIG. 48, determining the mean and standard deviation of each column of the stored distance matrix. The results may be stored for later use. FIG. 50 illustrates an example Normal Position Matrix storing the determined mean and standard deviation for each cluster in the study. Some embodiments may determine and store additional or different mean and standard deviation information. For example, if a mean Euclidean distance with respect to another parameter (column) was determined at 4616, a mean and standard deviation with respect to this parameter may be determined and stored.

The subroutine 5000 proceeds from 4622 to 4624. At 4624, the diagnostic system 104 determines an average cell frequency of each cluster. This may be done, for example with reference to the frequency matrix of FIG. 49, by averaging the columns. The results may be stored for later use, for example, for comparing cells of a test patient to a definition of a normal patient data set. FIG. 51 illustrates an example Normal Percent Matrix for the study storing the determined average or mean percentage of cells in each cluster. The subroutine 5000 proceeds from 4624 to 4626, where the subroutine 5000 ends.

Some embodiments of a system 100 may perform other acts not shown in FIG. 46, may not perform all of the acts shown in FIG. 46, or may perform the acts of FIG. 46 in different orders. For example, the subroutine 5000 may be modified in some embodiments to determine additional and/or different mean values at 4616, data may be stored in data structures other than float arrays and matrixes, etc. In another example, other or additional normal cluster configurations may be defined and modeled. For example, a first set of tubes of normal patient cells may be subjected to a first protocol generating first normal patient data sets with parameters for FSC, SSC, CD20 (FITC), CD10 (PE), CD45 and CD19, corresponding to ten clusters, a second set of tubes of normal patient cells may be subjected to a second protocol generating second normal data sets with parameters for FSC, SSC, CD22 (FITC), CD34 (PE), CD45 and CD 19, corresponding to four clusters, etc. The selected protocol(s) may be applied to set(s) of cells of a test patient to generate test patient data set(s) to be compared to the defined sets of clusters.

Figure 52:
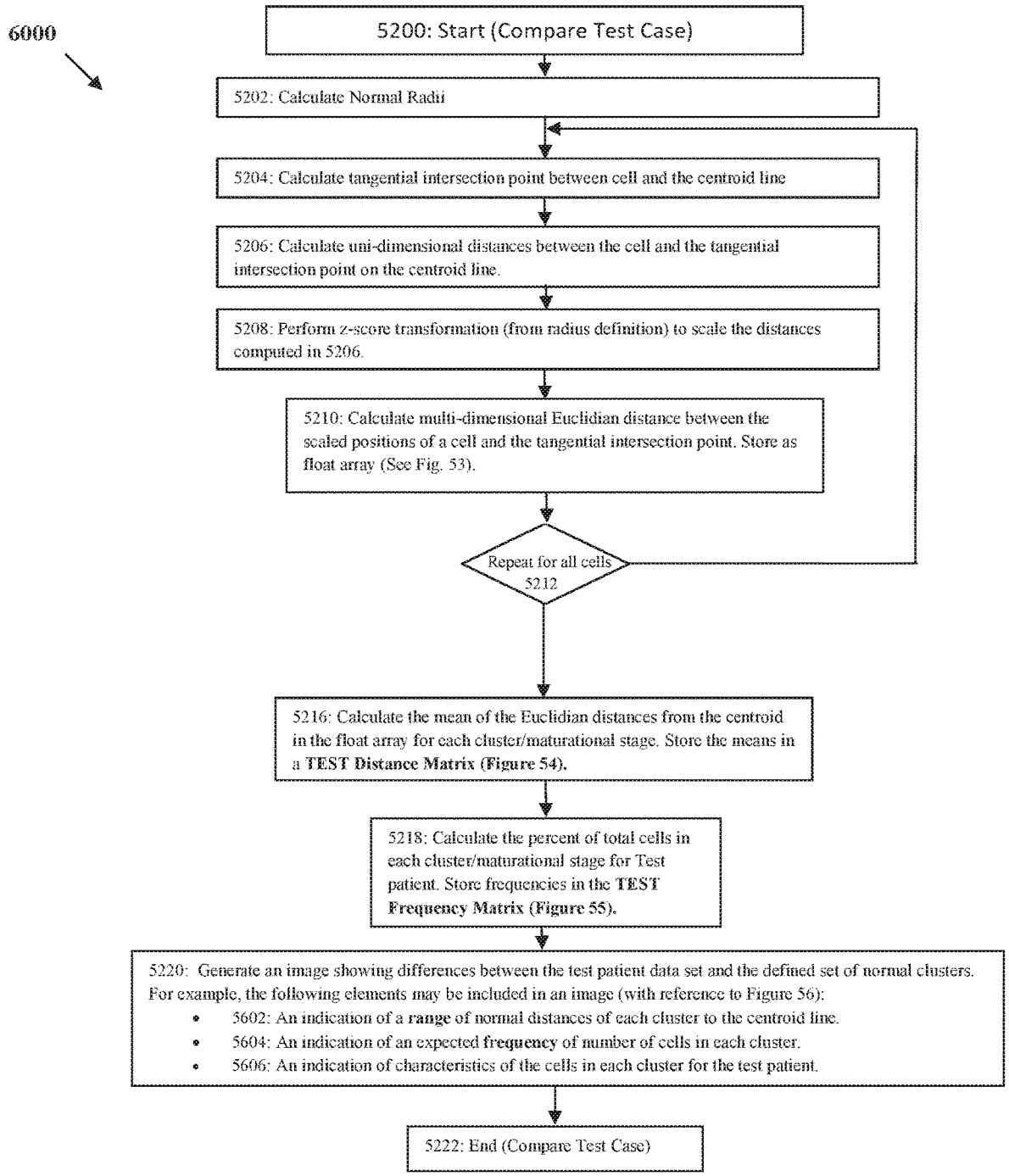
FIG. 52 is a flow chart illustrating operation of a system to compare a test patient set of cells (data points) to a defined set of normal clusters, by a system, such as the system illustrated in FIG. 1.

FIG. 52 is a flow diagram of an example subroutine 6000 that may be employed by a diagnostic system, such as the diagnostic system 104 of FIG. 1, to compare a test patient data set to a defined normal set of clusters, such a definition of a normal set of clusters generated using any of the methods disclosed above or various combinations of the disclosed methods, in a manner which facilitates quickly and efficiently communicating potential maturational stage abnormalities which may exist for the test patient. For convenience, the subroutine 6000 will be discussed with reference to FIGS. 52-57, and to the diagnostic system 104 of FIG. 1.

The subroutine 6000 starts at 5200 and proceeds to 5202. At 5202, normal radii are retrieved or determined by the diagnostic system 104 for a normal data set. For example, normal radii for a set of cells of a normal dataset may be determined, for example, as described above with reference to subroutine 4000 and FIGS. 40-45. There is no need to "repeat" for additional patients data sets (e.g., at acts 4010 and 4018, it will not be determined that additional patients data sets need to be processed), no need to merge normalized float arrays, etc. The subroutine 6000 proceeds from 5202 to 5204.

At 5204, a tangential intersection point between a cell of the test patient data set and the centroid line is identified on the centroid line defined for the normal patient data sets. Identification of the tangential intersection points on the centroid line may be done using dot products. See the discussion of determining tangential intersection points as discussed above with respect to FIGS. 40 and 41. As discussed above, the centroid line may be separated into segments and candidate segments may be used to identify the tangential intersection point of a cell, which may reduce the number of calculations required.

The subroutine 6000 proceeds from 5204 to 5206. At 5206, the diagnostic system 104 calculates uni-dimensional distances between the cell and the identified tangential intersection point for the cell on the centroid line. This may be done, for example, using Equation 2, set forth above and repeated below for convenience:

$$\text{Parameter Distance} = \text{Parameter}_{Cell} - \text{Parameter}_{TCP} \qquad [\text{Equation 2}]$$

where $\text{Parameter}_{Cell}$ is the value of a respective parameter for the cell and $\text{Parameter}_{TCP}$ is the value of the parameter for the tangential intersection point for the cell on the centroid line. The parameter distance values for the cell may be stored in a float array (see FIG. 53). The subroutine 6000 proceeds from 5206 to 5208.

At 5208, the diagnostic system 104 performs a z-score transformation on the distance data for the test patient data set (e.g., a float array for the test patient data set generated at 5206) based on the radii definition retrieved or determined at 5202.

The subroutine 6000 proceeds from 5208 to 5210. At 5210, the diagnostic system 104 determines the multidimensional Euclidean distance between the scaled positions of each cell (5208) and the centroid intersection point. This may be done, for example, using Equation 6, set forth below:

$$\text{Euclidean Distance} = \text{SQRT}(a^2 + b^2 + c^2 + d^2 + e^2 + f^2) \qquad \text{Equation 6}$$

where a-f are the standardized distances from the cell to the centroid line determined at 5208. A standardized float array may be generated for the test patient data set indicating the z-transformed distributions. The subroutine 6000 proceeds from 5210 to 5212.

At 5212, the diagnostic system 104 determines whether there are additional cells in the test patient data set to process. When it is determined at 5212 that there are additional cells of interest in the test patient data set to process, the subroutine 6000 returns to 5204 to process the next cell. When it is not determined at 5212 that there are additional cells of interest in the test patient data set to process, the subroutine proceeds to 5216.

At 5216, the mean Euclidean distance from the centroid line is calculated for each of the clusters/maturation stages for the test patient. For example, with reference to FIG. 53, a mean distance for each cluster for a patient may be determined with respect to the mean Euclidean Distance column of FIG. 53. The calculated mean values may be stored in a Test Patient Distance Matrix. FIG. 54 illustrates an example Test Patient Distance Matrix in a study, with each column corresponding to a cluster. Other mean distances may be determined, instead of or in addition to a mean Euclidean distance from the centroid line. For example, a mean distance for each cluster for the test patient may be determined with respect to other parameters, such as CD10 (PE) or any of the other parameters of the float array (e.g., FSC, SSC, CD20 (FITC), CD45, CD34, etc.).

The subroutine 6000 proceeds from 5216 to 5218. At 5218 a percentage of cells belonging to each cluster for the test patient is calculated. For example, the percentage of patient cells in a cluster for a test patient may be determined by dividing the number of patient cells in the patient data set which are in the cluster by the total number of patient cells in the patient data set, and multiplying the result by 100. Some embodiments may determine the proportion of cells of a patient data set in a cluster to a total number of cells in the patient data set in other manners, such as determining a ratio. The percentages may be stored in a Test Patient Frequency Matrix, as illustrated in FIG. 55 for the study. In theory, the percentages of FIG. 55 should add up to one-hundred percent. However, rounded values may be used in some embodiments, which may introduce minor rounding errors. The subroutine 6000 proceeds from 5218 to 5220.

At 5220, the diagnostic system 104 generates an image representing differences between the test patient data set and the defined set of normal clusters. For example, the diagnostic system 104 may generate pixels of an image. The image may show, for example, a comparison of the cell characteristics in the test patient set to the normal data set, such as frequency of cells in each maturational stage and average distance of cells from the centroid line.

Figure 56:
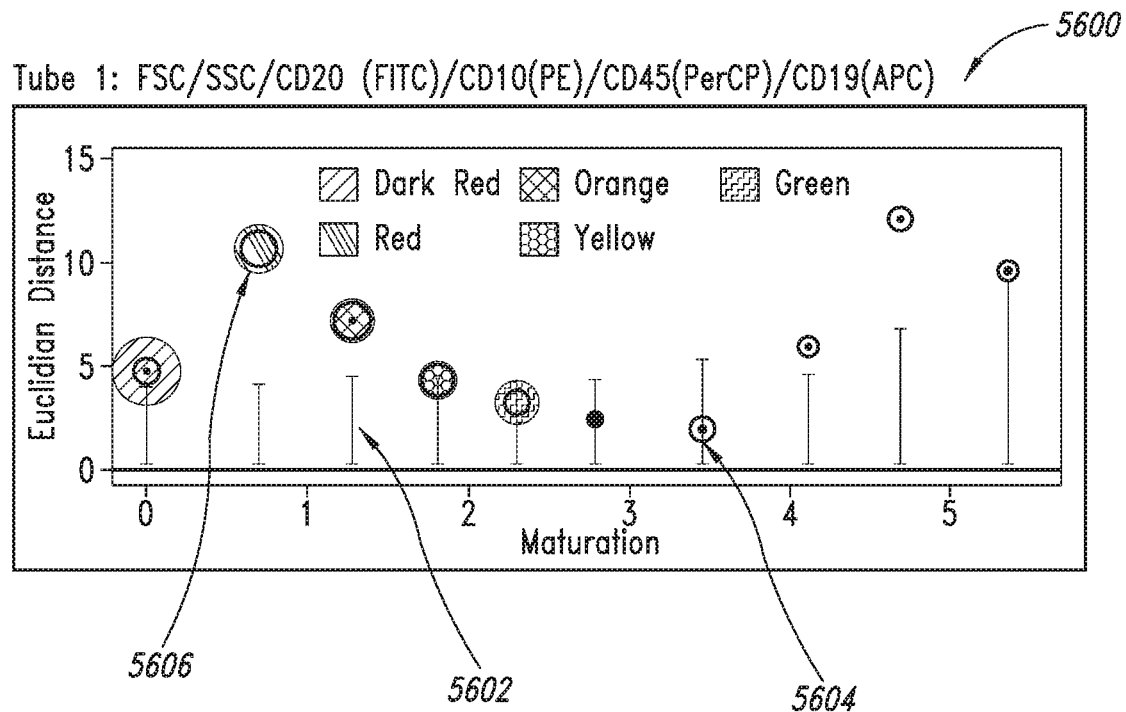
FIGS. 56 and 57 are illustrations of multi-dimensional data projected into a pseudo two-dimensional image generated by a system, such as the system illustrated in FIG. 1.

An example image 5600 is illustrated in FIG. 56 for the first set of tubes of normal patient cells in a study subjected to a first protocol generating first normal patient data sets with parameters for FSC, SSC, CD20 (FITC), CD10 (PE), CD45 (PerCP) and CD19 (APC), corresponding to ten clusters. In FIG. 56, immature clusters are on the left and mature clusters are on the right.

As illustrated in FIG. 56, image 5600 includes respective indications of ranges 5602 of normal distances of each defined normal cluster to the centroid line. For clarity of illustration, the reference number 5602 is used to identify only one of the range indicators in FIG. 56 (the range indicator for the third cluster from the left). The respective ranges for each cluster may be determined, for example, using the mean position of each cluster (e.g., the mean position row of the Normal Position Matrix of FIG. 50). As illustrated, the lower limit of the respective ranges is 0, and the upper limit of the respective ranges is the mean position of the cluster plus two times the standard deviation in the mean position of the cluster (e.g., the standard deviation position row of the Normal Position Matrix of FIG. 50). For example, with reference to the third cluster from the left, the mean position of the cluster in the Normal Position Matrix is 3.04 and the standard deviation in position is 0.75. Thus, for example, the indication of a range 5602 runs from 0 to 4.54 for the third cluster. The indication of a range 5602, for example, indicates a statistical range where 97.5 percent of the normal centers of each defined normal cluster resided from the centroid line. Indications other than lines may be employed.

The image 5600 includes respective indications 5604 of an expected frequency of number of cells in each defined normal cluster. This is represented in FIG. 56 by scaling a black outline of a circle according to average frequency of cells in each defined normal cluster (e.g., from row 1 of the Normal Percent Matrix of FIG. 51). For clarity of illustration, the reference number 5604 is used to identify only one of the expected frequency indicators in FIG. 56 (the expected frequency indicator for the seventh cluster from the left). Clusters with higher average frequencies are proportionally larger than clusters with smaller average frequencies. For example, the circle indicating the expected frequency corresponding to cluster 7 is smaller than the circle indicating the average frequency for cluster 3, indicating cluster 7 has a lower expected cell frequency than cluster 3. Shapes other than circles may be employed.

The image 5600 includes respective indications 5606 of the distance of the cells in test patient data set from the centroid line and of the frequency of cells of the cluster in the test patient data set. As illustrated a colored circle summarizes the cells in each cluster for the test patient. The size of the circle corresponds to the test frequency of that particular cluster (from the test frequency matrix). For clarity of illustration, the reference number 5606 is used to identify only one of the indicators of the distance and frequency of cells of the test patient data set in FIG. 56 (the indicator of the distance and frequency of cells of the second cluster from the left of the test patient data set). If the colored circle of the indication 5606 is bigger than the black outline of the indication 5604 of the corresponding defined normal cluster, this communicates that the number of cells in the test patient's cluster exceeds the average frequency of this cluster in the normal data set. If the colored circle of the indication 5606 is smaller than the black outline of the indication 5604 of the corresponding defined normal cluster, this communicates that the number of cells in the test patient's cluster less than the average frequency of this cluster in the normal data set.

The size of the black circle 5604 may vary depending on certain patient characteristic, such as age. For example, pediatric patients have more immature cells than elderly patients. Therefor, the black circle size may be different for different patient populations. The positions will generally be the same for different populations.

The position of the circle 5606 corresponds to the average distance of cells in the cluster of the test patient to the centroid line. If the circle falls outside of the indicated range 5602, this communicates that the cells in the cluster for the test patient sit farther-than average from the centroid line, which may indicate a potential abnormality (cancer). It is noted that in FIG. 56, the position of the indication 5604 of the expected frequency of a number of cells in each defined normal cluster coincides with the position of the indication 5606 of the distance in the test patient data set from the centroid line. In other words, the position of the indication 5604 does not indicate a distance or distance range of a defined normal cluster from the centroid line. Having a position of the indication 5604 coincide with a position of the indication 5606 facilitates comparing the expected frequency of the number of cells in a defined normal cluster with the frequency of the cells of the cluster in the test patient data set.

Figure 57:
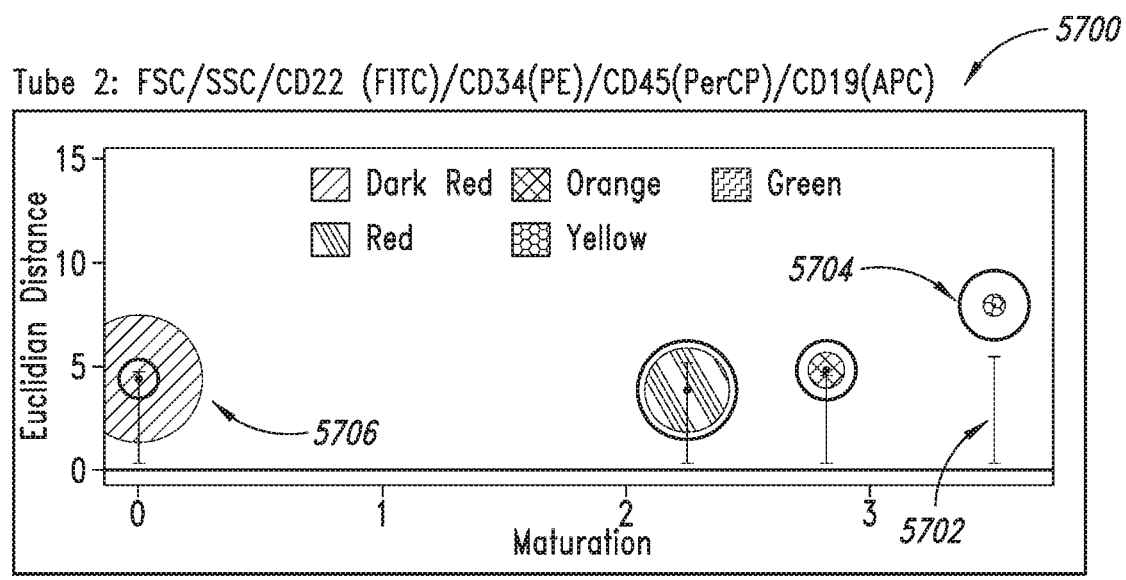

Another example image 5700 is illustrated in FIG. 57 for the second set of tubes of normal patient cells subjected to a second protocol generating second normal data sets with parameters for FSC, SSC, CD22 (FITC), CD34 (PE), CD45 (PerCP) and CD19 (APC), corresponding to four clusters. In FIG. 57, immature clusters are on the left and mature clusters are on the right.

As illustrated in FIG. 57, image 5700 includes an indication of a range 5702 of normal distances of each defined normal cluster to the centroid line. The range may be determined, for example, using the mean position of each cluster plus or minus two times the standard deviation in the mean position of the cluster. The image 5700 includes an indication 5704 of an expected frequency of number of cells in each defined normal cluster. This is represented in FIG. 57 by scaling a black outline of a circle according to average frequency of cells in each defined normal cluster. Clusters with higher average frequencies are proportionally larger than clusters with smaller average frequencies. Shapes other than circles may be employed.

The image 5700 includes an indication 5706 of the distance of the cells in test patient data set from the centroid line and of the frequency of cells of the cluster in the test patient data set. As illustrated a colored circle summarizes the cells in each cluster for the test patient. The size of the circle corresponds to the test frequency of that particular cluster (from the test frequency matrix). If the colored circle of the indication 5607 is bigger than the black outline of the indication 5704 of the corresponding defined normal cluster, this communicates that the number of cells in the test patient's cluster exceeds the average frequency of this cluster in the normal data set.

The size of the black circle 5704 may vary depending on certain patient characteristic, such as age. For example, pediatric patients have more immature cells than elderly patients. Therefore, the black circle size may be different for different patient populations. The positions will generally be the same for different populations.

The position of the circle 5706 corresponds to the average distance of cells in the cluster of the test patient to the centroid line. If the circle falls outside of the indicated range 5702, this communicates that the cells in the cluster for the test patient sit farther-than average from the centroid line, which may indicate a potential abnormality (cancer). Normally, the interpretation should be performed by a medical expert (e.g., a physician), which may include considering other information about the patient. It is noted that in FIG. 57, the position of the indication 5704 of the expected frequency of a number of cells in each defined normal cluster coincides with the position of the indication 5706 of the distance in the test patient data set from the centroid line. In other words, the position of the indication 5704 does not indicate a distance or distance range of a defined normal cluster from the centroid line. Having a position of the indication 5704 coincide with a position of the indication 5706 facilitates comparing the expected frequency of the number of cells in a defined normal cluster with the frequency of the cells of the cluster in the test patient data set. The subroutine 6000 proceeds from 5220 to 5222, where the subroutine 6000 ends.

Some embodiments of a system 100 may perform other acts not shown in FIG. 52, may not perform all of the acts shown in FIG. 52, or may perform the acts of FIG. 52 in different orders. For example, the subroutine 6000 may be modified in some embodiments to determine additional and/or different means at 5216, data may be stored in data structures other than float arrays and matrixes, etc. In another example, other or additional normal cluster configurations may be defined and modeled. In another example, the subroutine 6000 may be modified to store, display or print generated images.

Figure 58:
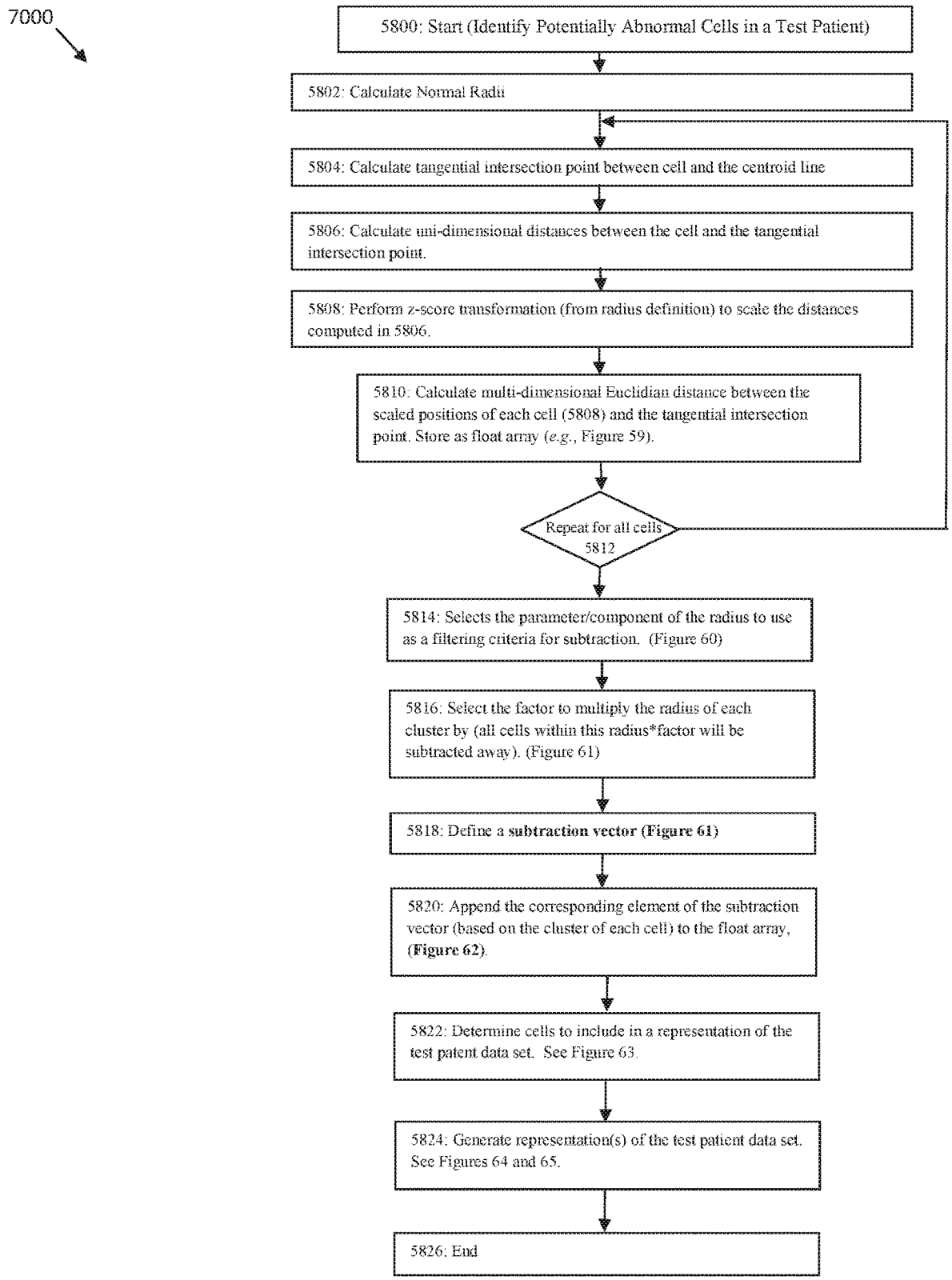
FIG. 58 is a flow chart illustrating operation of a system to compare a test patient set of cells (data points) to a defined set of normal clusters, by a system, such as the system illustrated in FIG. 1.

FIG. 58 is a flow diagram of an example subroutine 7000 that may be employed by a diagnostic system, such as the diagnostic system 104 of FIG. 1, to compare a test patient data set to a defined normal set of clusters, such a definition of a normal set of clusters generated using any of the methods disclosed above or various combinations of the disclosed methods, in a manner which facilitates quickly and efficiently communicating potential maturational stage abnormalities which may exist for the test patient. For convenience, the subroutine 7000 will be discussed with reference to FIGS. 58-65, and to the diagnostic system 104 of FIG. 1.

The subroutine 7000 starts at 5800 and proceeds to 5802. At 5802, normal radii are retrieved or determined by the diagnostic system 104 for a set of cells of a set of normal patients. The subroutine 7000 proceeds from 5802 to 5804. At 5804, the cells of a test patient data set are clustered to corresponding reference points and a tangential intersection point between a cell of the test patient data set and the centroid line is identified on the centroid line defined for the normal patient data sets. The test patient data set may be a data set of a lineage or reference population identified, for example, by using an SVM. Identification of the tangential intersection points on the centroid line may be done using dot products. See the discussion of determining tangential intersection points as discussed above with respect to FIGS. 40, 41 and 41A. As discussed above, the centroid line may be separated into segments and candidate segments may be used to identify the tangential intersection point of a cell, which may reduce the number of calculations required.

The subroutine 7000 proceeds from 5804 to 5806. At 5806, the diagnostic system 104 calculates uni-dimensional distances between the cell and the identified tangential intersection point for the cell on the centroid line. This may be done, for example, using Equation 2, set forth above and repeated below for convenience:

$$\text{Parameter Distance} = \text{Parameter}_{Cell} - \text{Parameter}_{TCP} \quad \text{[Equation 2]}$$

where $\text{Parameter}_{Cell}$ is the value of a respective parameter for the cell and $\text{Parameter}_{TCP}$ is the value of the parameter for the tangential intersection point for the cell on the centroid line. The parameter distance values for the cell may be stored in a float array (see FIG. 59). The subroutine 7000 proceeds from 5806 to 5808.

At 5808, the diagnostic system 104 performs a z-score transformation on the distance data for the test patient data set (e.g., a float array for the test patient data set generated at 5806) based on the radii definition retrieved or determined at 5802.

The subroutine 7000 proceeds from 5808 to 5810. At 5810, the diagnostic system 104 determines the multidimensional Euclidean distance between the scaled positions of each cell (5808) and the centroid intersection point. This may be done, for example, using Equation 7, set forth below:

$$\text{Euclidean Distance} = \text{SQRT}(a^2 + b^2 + c^2 + d^2 + e^2 + f^2) \quad \text{Equation 7}$$

where a-f are the standardized distances from the cell to the centroid line determined at 5808. A standardized float array may be generated for the normal patient data set indicating the z-transformed distributions. The subroutine 7000 proceeds from 5810 to 5812.

At 5812, the diagnostic system 104 determines whether there are additional cells in the test patient data set to process. When it is determined at 5812 that there are additional cells of interest in the test patient data set to process, the subroutine 7000 returns to 5804 to process the next cell. When it is not determined at 5812 that there are additional cells of interest in the test patient data set to process, the subroutine proceeds to 5814.

At 5814, a parameter/component of the radius is selected to use as a filtering criteria for subtraction. This may be done, for example, based on a default parameter, based on a user selection, etc. For example, a user may select Euclidean distance if it is desired to identify cells that are different from normal considering all parameters combined. In another example, the user may select CD10 if it is desired to identify only those cells with different-from-normal CD10 expression. FIG. 45 illustrates a normal radius table, which may be generated, for example, using the subroutine 4000 discussed above with reference to FIGS. 40-45. As illustrated in FIGS. 60-63, the Euclidean distance is selected as the basis of filtering in an embodiment of the study. As illustrated in FIGS. 60A-63A, CD10 is selected as the basis of filtering in an embodiment of the study. When the selected filtering embodiment is an individual parameter, the absolute value of the test parameter may be compared to the subtraction vector to determine if the cell should be subtracted (e.g. FIG. 63A cell 3). The subroutine 7000 proceeds from 5814 to 5816.

At 5816, a multiplication factor is selected. This may be done, for example, based on a default multiplication factor (which may vary based on the selected filtering parameter(s), the cluster, etc.), based on a user selection, etc. Look-up tables may be employed. The subroutine 7000 proceeds from 5816 to 5818. At 5818, a subtraction vector is generated, for example by multiplying the selected radius standard deviation for each cluster by the selected multiplication factor for the cluster and adding this to the selected radius mean for the cluster. FIGS. 61 and 61A illustrate example radius tables storing the selected radius (from 5814), the selected multiplication factor (from 5816) and the subtraction vector (from 5818). The subroutine 7000 proceeds from 5818 to 5820.

At 5820, as illustrated in FIGS. 62 and 62A, the subtraction vector for each cluster is appended to the float array of FIG. 59. The subroutine 7000 proceeds from 5820 to 5822. At 5822, the subroutine 7000 determines cells to include in a representation (e.g., an image) of the test patient data set. This may be done, for example, by comparing the variable of interest selected as a filtering criteria (see 5814) for each cell to the subtraction vector. Cells which are less than or equal to the subtraction vector may be marked to not be included in the representation of the test patient data set, to be subtracted, to not be displayed, to be translucent, etc. The data may be stored in a float array, as illustrated in FIG. 63, which shows a Euclidean Distance being used as a filtering criteria which is compared to the subtraction vector in order to determine whether to exclude a cell from a representation of the test patient data set.

The subroutine 7000 proceeds from 5822 to 5824. At 5824, the subroutine generates one or more representations (images) of the test patient data set. This may be done, for example, using one or more float arrays generated at 5822 to generate a pixel display representation of the test patient data set.

Figure 64:
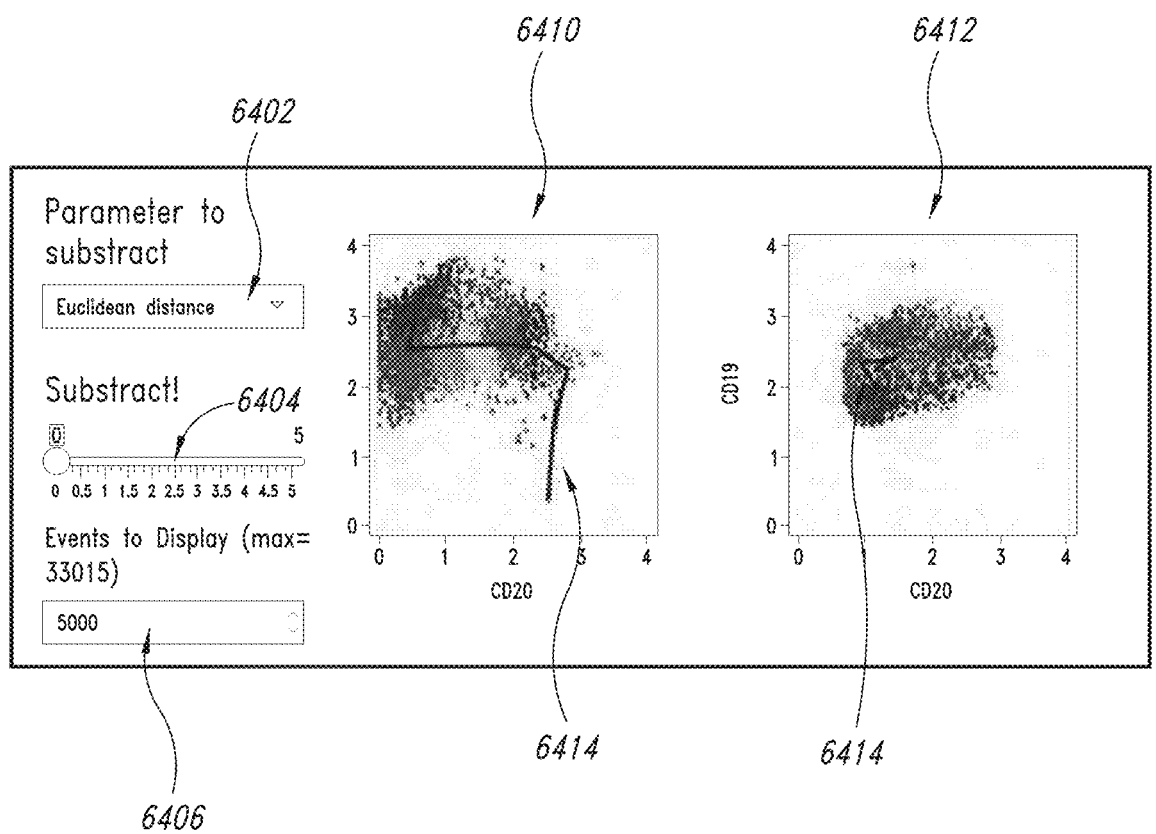
FIGS. 64, 64A, 64B, 65, 65A and 65B illustrate example user-interfaces to control the generation of and to display images representing cells (data points) of a test patient data set.
Figure 65:
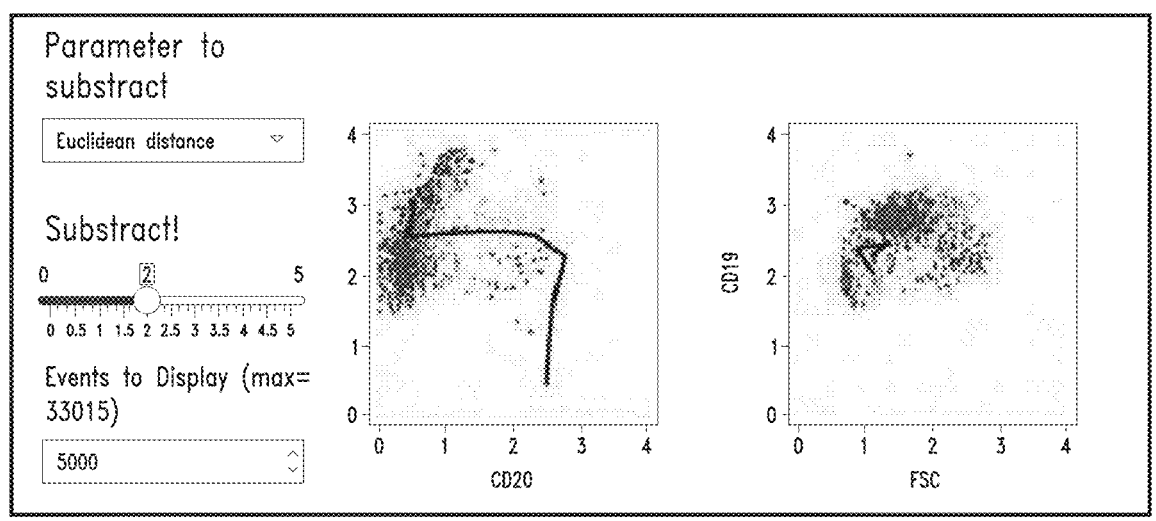

FIGS. 64 and 65 illustrate example an user interface to control the generation and to display representations of test patient data sets. As illustrated, the user-interface of FIG. 64 includes user-selectable controls and/or data input fields 6402, 6404, and 6406, and representations of the test patient data set 6410 and 6412. A first user-selectable control 6402 allows the user to select a parameter of the radius upon which to filter the test patient data set (see 5814 of FIG. 58), and as illustrated is a drop-down menu selector 6402. As illustrated, drop-down menu selector shows "Euclidean distance" as the selection, which corresponds to selecting the Euclidean Distance, a six-dimensional radius in the study. Other filter options could be selected to facilitate representing cells which exceed an individual parameter (e.g., CD10, SSC, etc.). A second user-selectable control 6404 allows the user to set subtraction vector (see 5818 of FIG. 58), and as illustrated is a sliding bar. Some embodiments may allow a user to select a multiplication factor to be used to define the subtraction vector. A data input field 6406 allows a user to enter a number of events to display. The number of events to display may be used to indicate a number of cells of the test patient data set to process in generating the display (e.g., the first 5000 cells, the first 5000 cells which are not subtracted, 5000 cells of a cluster (maturational stage), etc.) More cells may need to be visualized to detect lower levels of leukemia. In an embodiment, a default number of cells may be selected, a maximum number of cells may be set, etc. FIG. 64 illustrates a display of a test patient data set when the subtraction vector magnitude is set to zero, and FIG. 65 illustrates a display of a test patient data set when the subtraction vector magnitude is set to 2. FIGS. 64A through 65B illustrate example user interfaces and display representations when the interface includes a control to select a plot group. A plot group may simply be a lineage of cells to visualize. For example, the user could select to visualize the neutrophil cells, the monocyte cells, the lymphoid cells, etc., or any combination to facilitate, for example, visualizing any cells that are different from normal maturational patterns.

Figure 64A:
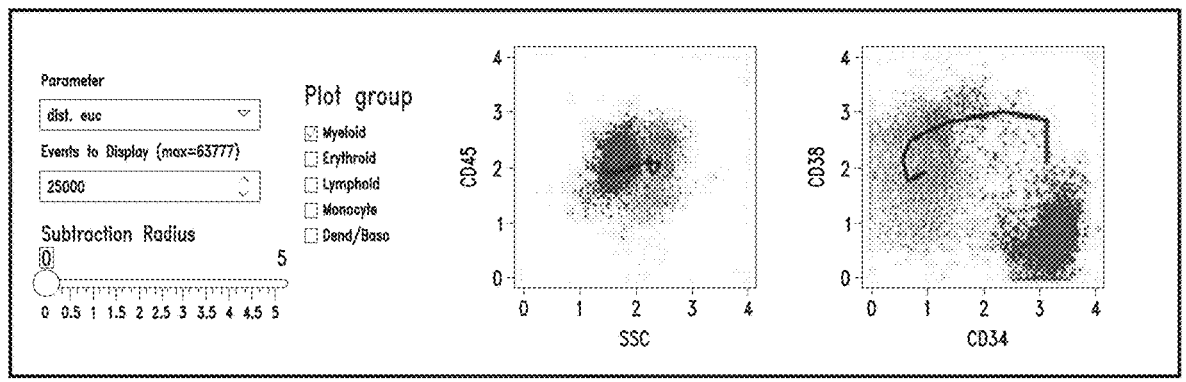
Figure 64B:
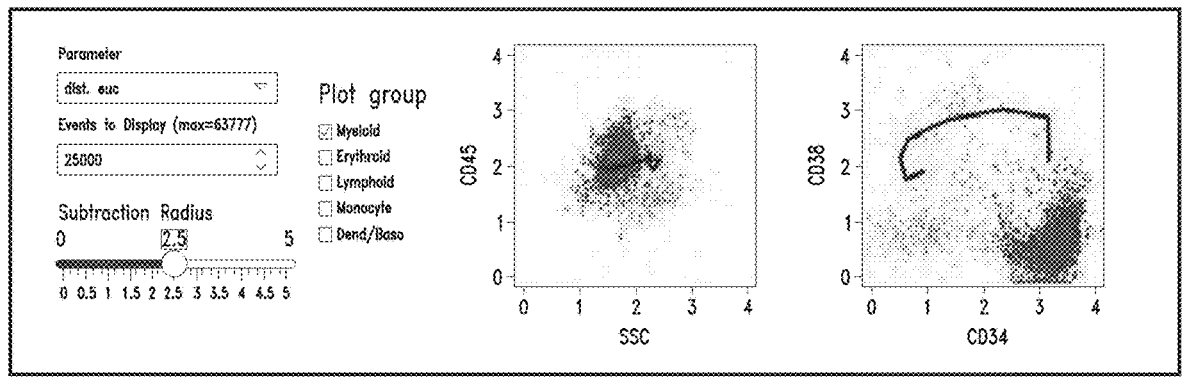
Figure 65A:
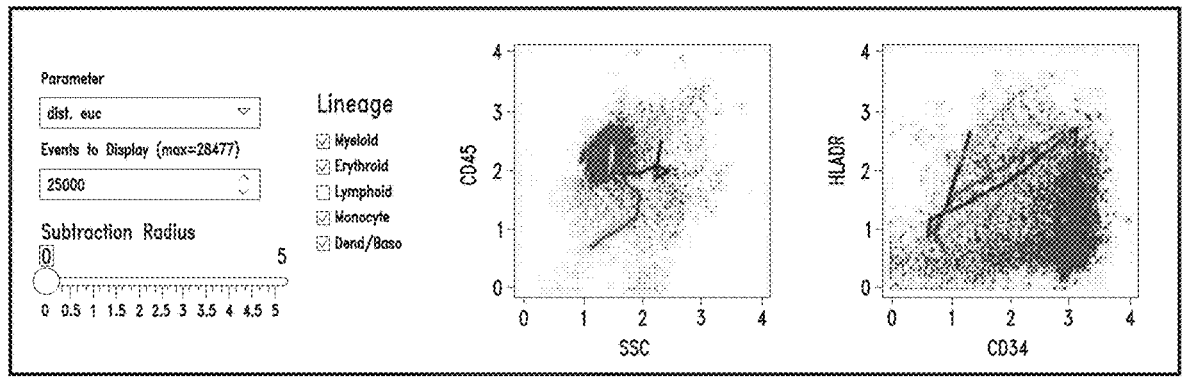
Figure 65B:
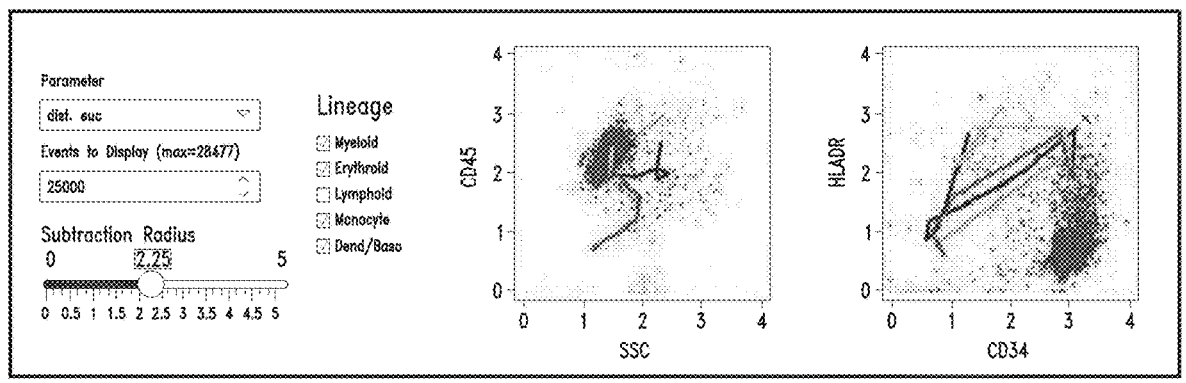

In an embodiment, pixels representing subtracted cells may be semi-transparent, and pixels representing non-subtracted cells may be colored based on the cluster to which the cell is assigned. Cells of other lineages or other reference populations may be displayed as well in some embodiments (e.g., plasma cells may be displayed together with B-lymphoid cells), and controls to facilitate selection of such lineages may be provided. As illustrated, FIGS. 64 and 65 include a pixel display 6410 representing the test patient data set with CD10 on a vertical axis and CD20 on a horizontal axis and a pixel display 6412 representing the test patient data set with CD45 on the vertical axis and SSC on a horizontal axis. The defined centroid line 6414 for the set of normal clusters is represented in the display with black pixels. In an embodiment, subtracted cells may be represented with transparent pixels, and non-subtracted cells may be represented with pixel colors based on the cluster to which the cell is assigned. In an embodiment, subtracted cells may not be included in the display. In FIG. 64, the subtraction vector is set to zero. Thus, the subtraction vector is zero and the pixel displays 6410 and 6412 include colored pixels representing all the cells of the test patient data set (up to any limit set via user-selectable control 6406). In FIG. 65, the subtraction vector is set to 2. Thus, the subtraction vector is not zero and the pixel displays 6410 and 6412 include colored pixels representing cells of the test patient data set which are more than 2 standard-deviations away from the centroid line 6414 in standardized six-dimensional Euclidean space, while pixels representing cells of the test patient which are not more than 2 standard deviations away from the centroid line 6414 are semi-transparent (or are not included in the representation). FIGS. 64A-B is a pixel display depicting cells sitting outside the radius of the neutrophil centroid line. FIGS. 65A-B is a pixel display depicting cells outside of the radius of the neutrophil, erythroid, monocyte, and dendritic cell centroid lines.

The subroutine 7000 proceeds from 5824 to 5826, where the subroutine 7000 ends. Some embodiments of a system 100 may perform other acts not shown in FIG. 58, may not perform all of the acts shown in FIG. 58, or may perform the acts of FIG. 58 in different orders. For example, the subroutine 7000 may be modified in some embodiments to combine acts 5822 and 5824 instead of separately determining cells to include in a representation of the test patient data set and generating the representations of the test patient data set. In another example, the subroutine may include a loop to facilitate generating representations in a dynamic manner, for example by adjusting the multiplication factor, the filtering parameters, the number of representations the axis parameters in a dynamic manner. In another example, an embodiment may be modified to generate float arrays excluding subtracted cells, which may facilitate remote display of the representations by reducing the amount of data used to generate the display. In another example, the subroutine 7000 may be modified to store or print generated images.

Using an embodiment of this approach, the complexity of analysis of, for example, six or more dimensional data may be simplified and related to a statistical analysis of normal cells. In addition, the data may be separated into different lineages with a further distinction of maturational stages with that lineage. This facilitates a more intuitive interpretation by physicians who are familiar with the concept of maturation of cells from progenitor cells, through various stages of development to mature blood cells. It is important to be able to distinguish between a regenerating bone marrow with increased numbers of immature normal cells (referred to as a shift to the left) as distinct from the presence of abnormal cells. This presentation combines the concept of a single lineage, the maturation of the lineage, and the frequency of test cells in reference to the expected frequency for each developmental stage, and whether or not these populations of cells are within an expected statistical range of position in an N dimensional space. This information may be combined with knowledge of the patient, the patient's clinical data such as whole blood count, cytogenetics, and history of therapy. Therefore, the data may be interpreted in the course of the practice of medicine. This illustration simplifies the analysis for the physician instead of thinking in six-dimensional space. This may be facilitated by subtracting away events close to a normal centroid. The human eye is very good at identifying clusters of events and distinguishing them from random events that are slightly outside of the expected boundaries.

Results of a study of statistical characteristics of lymphocyte, promyelocyte, monocyte and CD34 bright reference populations confirms positions of reference populations may be identified which remain constant in a six-dimensional space even after treatment with chemotherapy, and thus may be used to define the variability of normal cells in stressed bone marrow specimens. Thus, the use of support vector machines as discussed herein to identify reference populations may provide a basis of determining a difference from normal.

Figure 66:
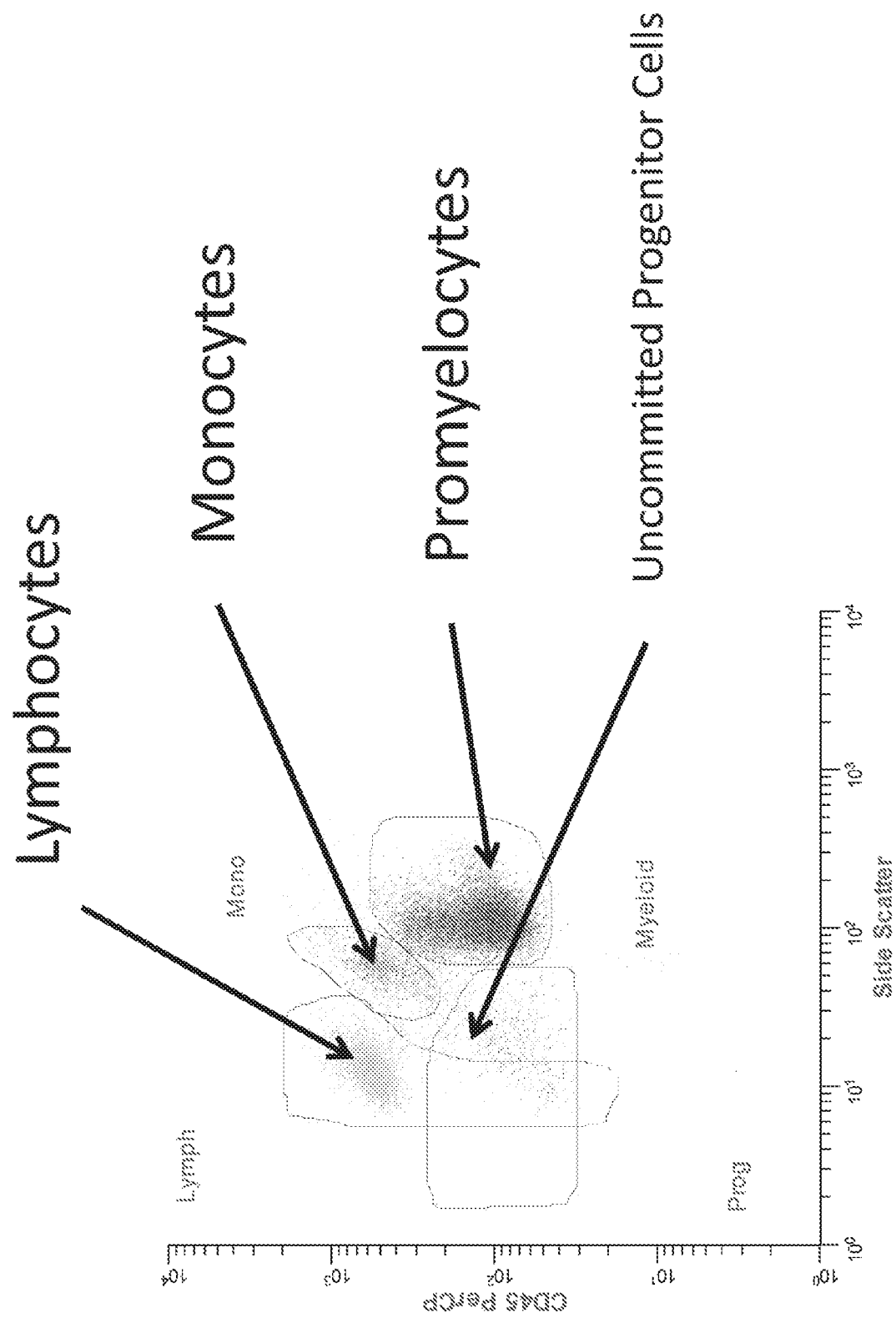
FIG. 66 illustrates a reference population of cells.

In a study, internal reference populations considered were defined based on discrete cell clusters, including mature lymphocytes, uncommitted progenitor cells, promyelocytes, mature neutrophils and mature monocytes. The study is discussed in more detail below. A representation of a reference population of cells appears in FIG. 66.

A data set of 77 randomly selected, phenotypically normal, End of Induction (day 28) pediatric AML patients enrolled on AAML1031. Three years of patient data was collected using three flow cytometers. Multiple lots of reagents for each antigen were studied. The amount of surface gene expression changes throughout the maturation of HSC to mature hematopoietic cells was studied for each lineage to characterize and compare reference population in multidimensional space.

Figure 67:
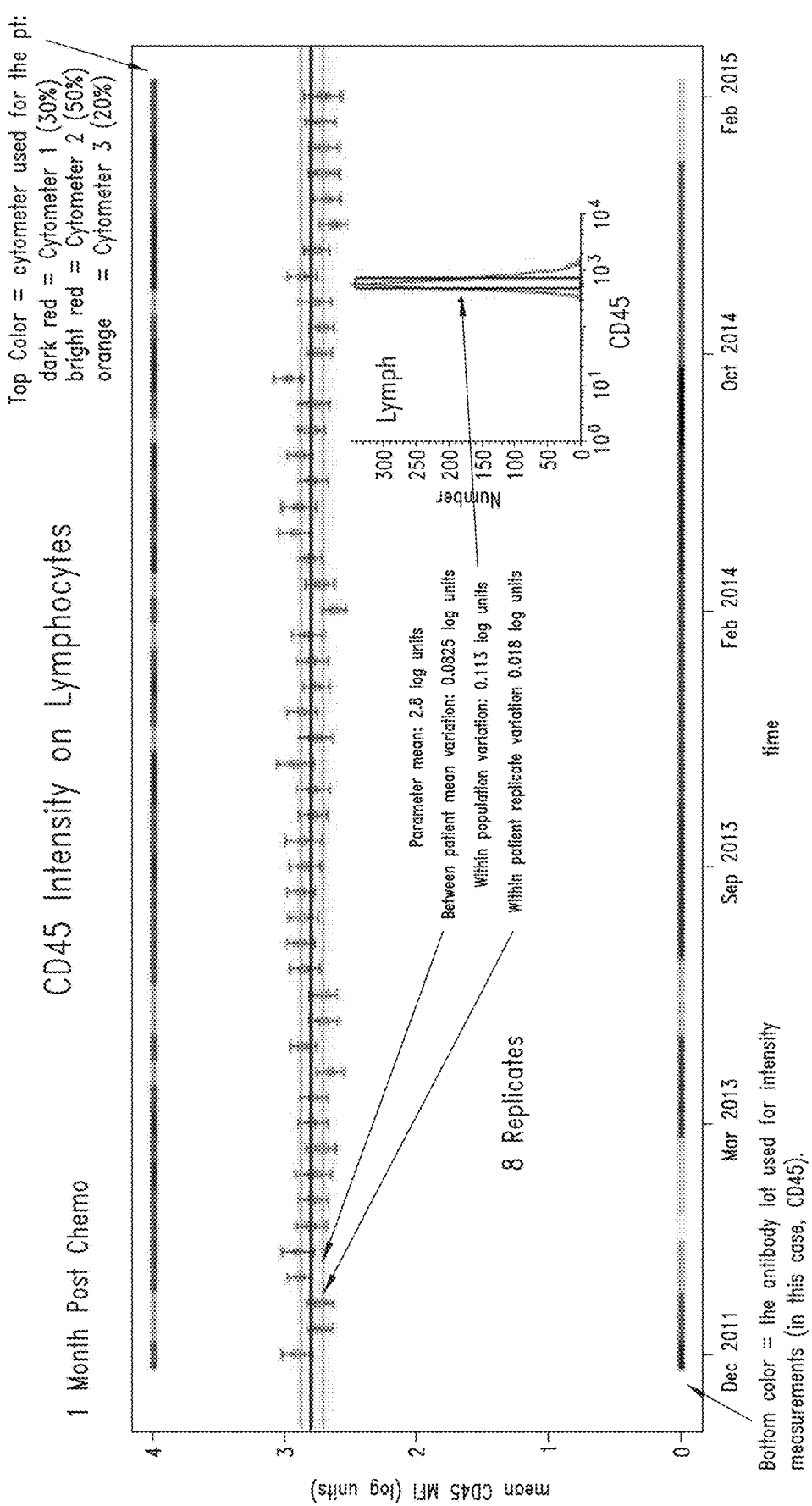
FIGS. 67 and 68 are representations of results for test patient data sets.
Figure 68:
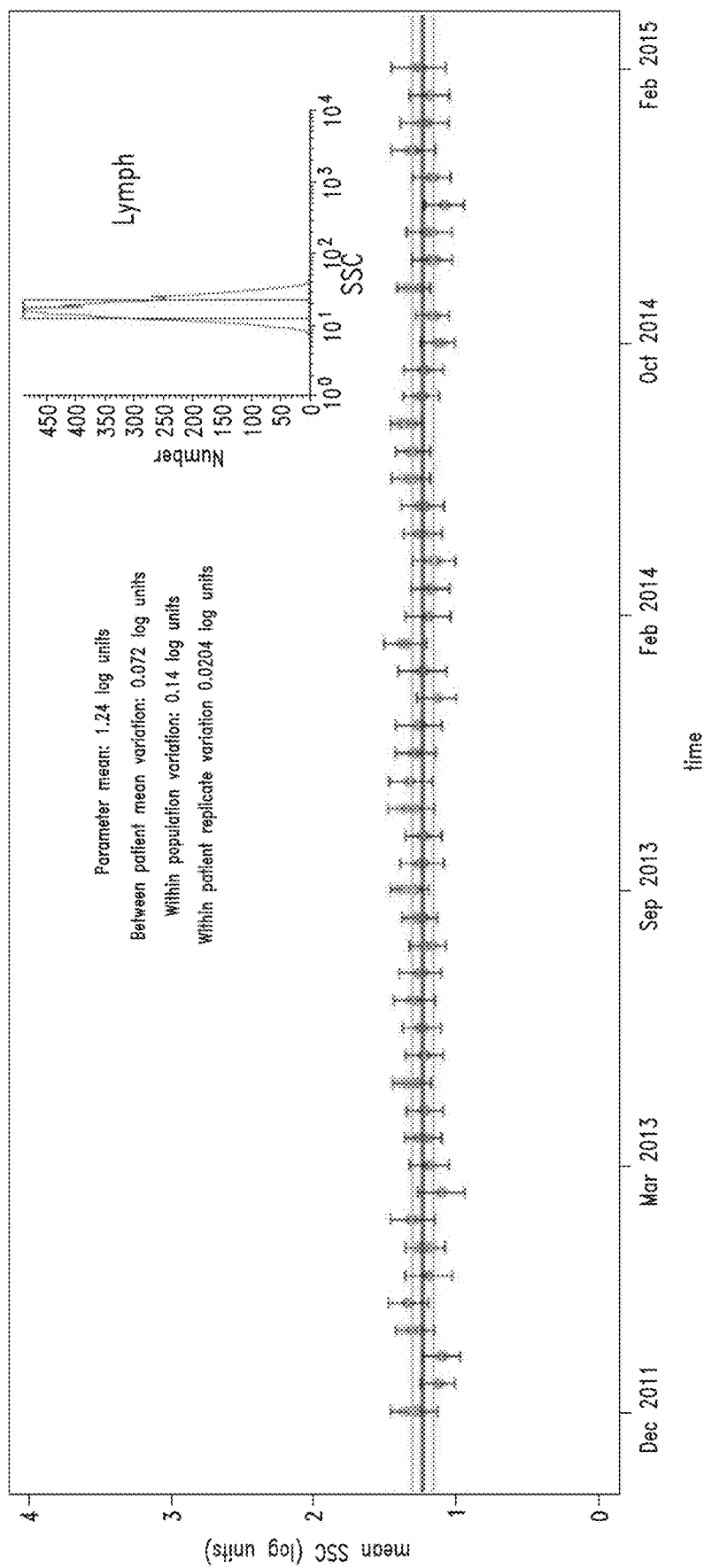

A first reference population studied was lymphocytes. Lymphocytes are in every specimen and were used as a reference for CD45, SSC and FSC. Lymphocytes are negative for CD34. CD45 intensity was used to demonstrate a sufficient antibody to cell ratio. A support vector machine was trained using an embodiment of the method discussed above with reference to FIG. 27 on manually-selected lymphocytes populations for 27 normal patients with 8 tubes=216 normal data sets. The defined multidimensional boundary was applied using an embodiment of the method discussed above with reference to FIG. 28 to the normal patients and to 50 test patients (8 tubes=400 test patient data sets) to predict the lymphocytes population. A manual gating reference was not applied. FIG. 30 illustrates the lymphocyte population of a normal patient and FIG. 35 illustrates the lymphocyte population for a test patient. For each of the 27 normal patients and for the 50 test patients, the mean and standard deviation antigen intensity for each marker in each tube was determined using an embodiment of the method discussed above with reference to FIG. 29. For the normal patient data, a mean of the mean was determined. The consistency of antigen intensity of the test patients was compared to the determined mean of the normal means. Representations of the results for the 50 test patient data sets are reproduced in FIGS. 67 and 68.

Figure 69:
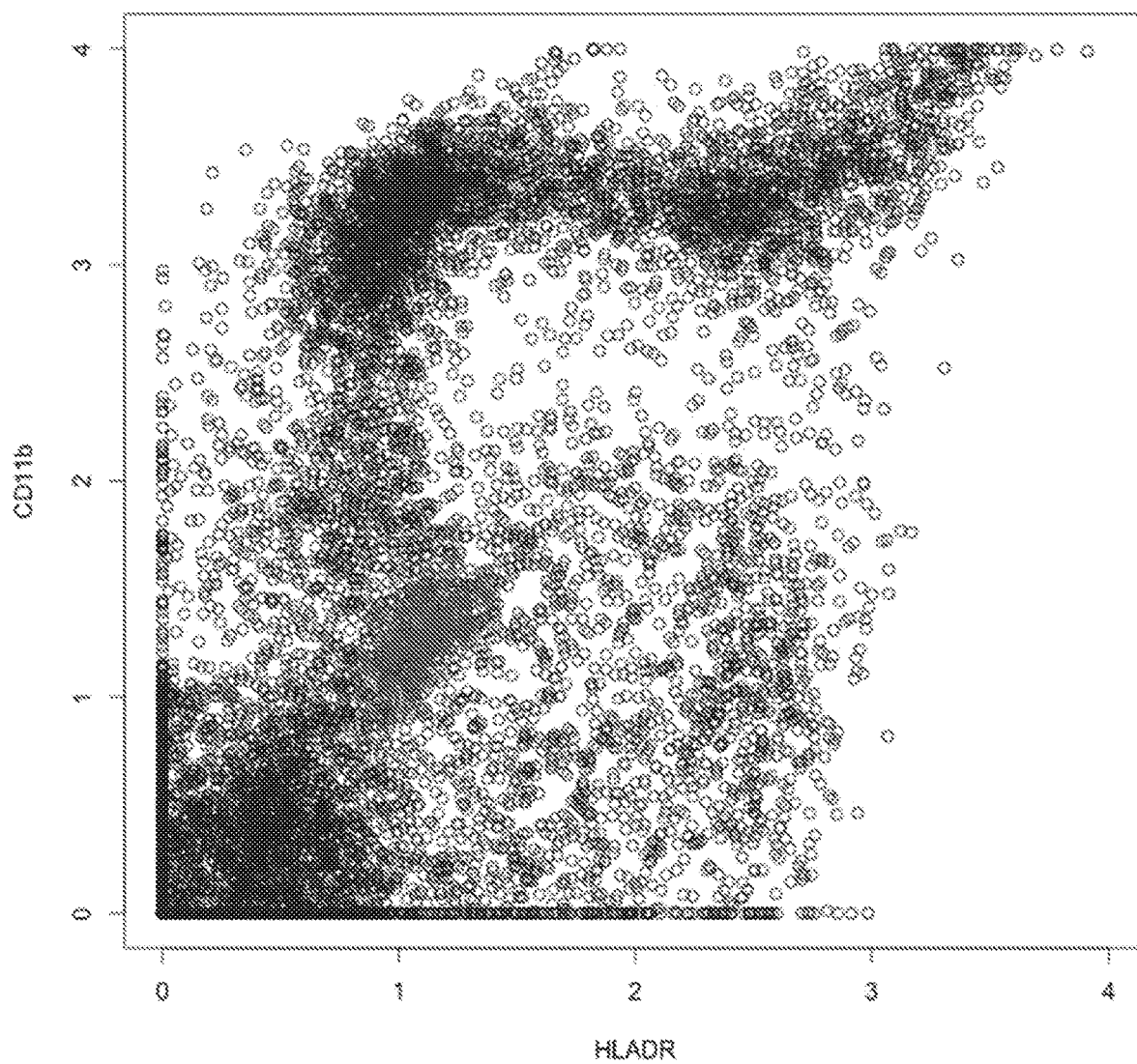
FIG. 69 is a representation of a predicted population for promyelocytes.
Figure 70:
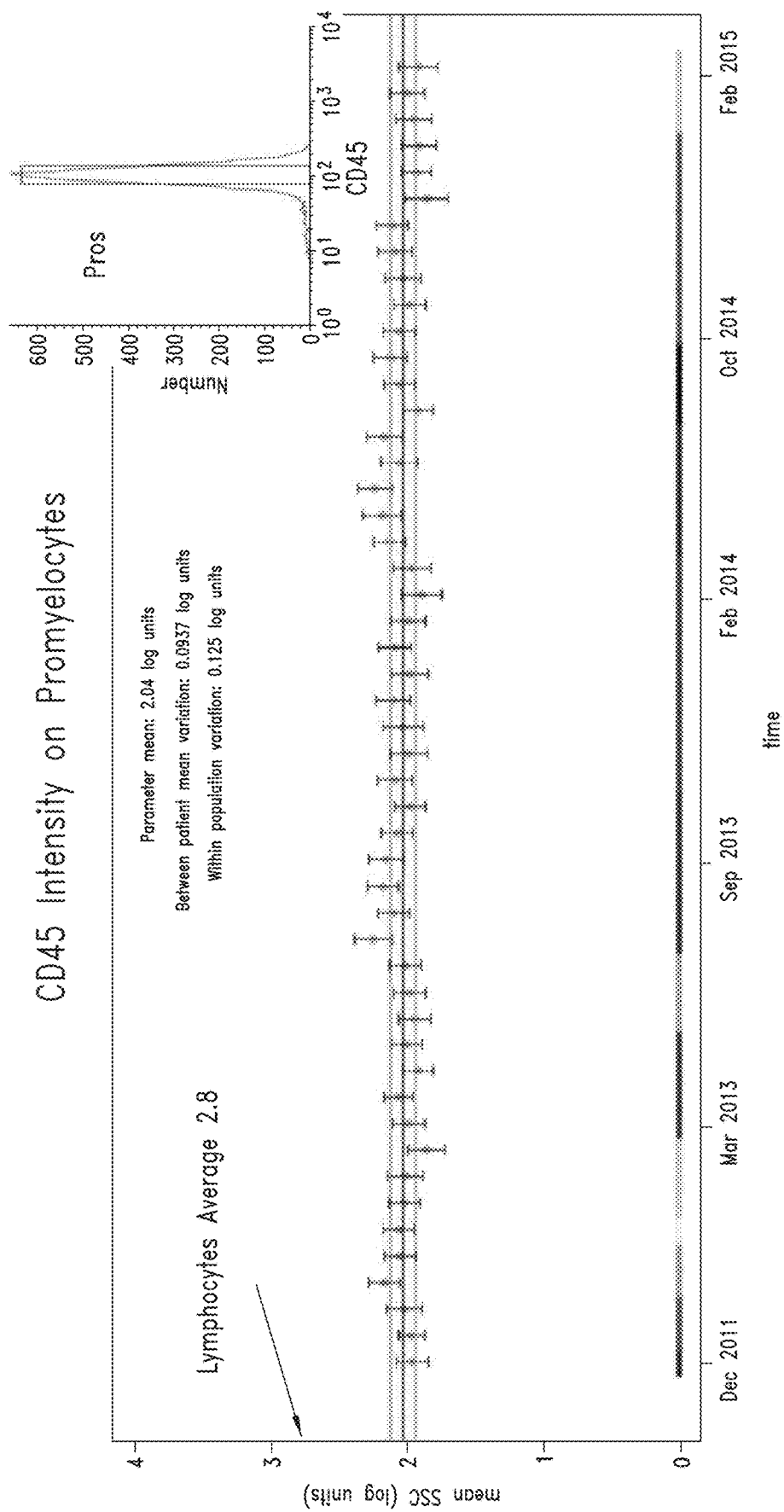
FIGS. 70 and 71 are illustrations of results for a data set.
Figure 71:
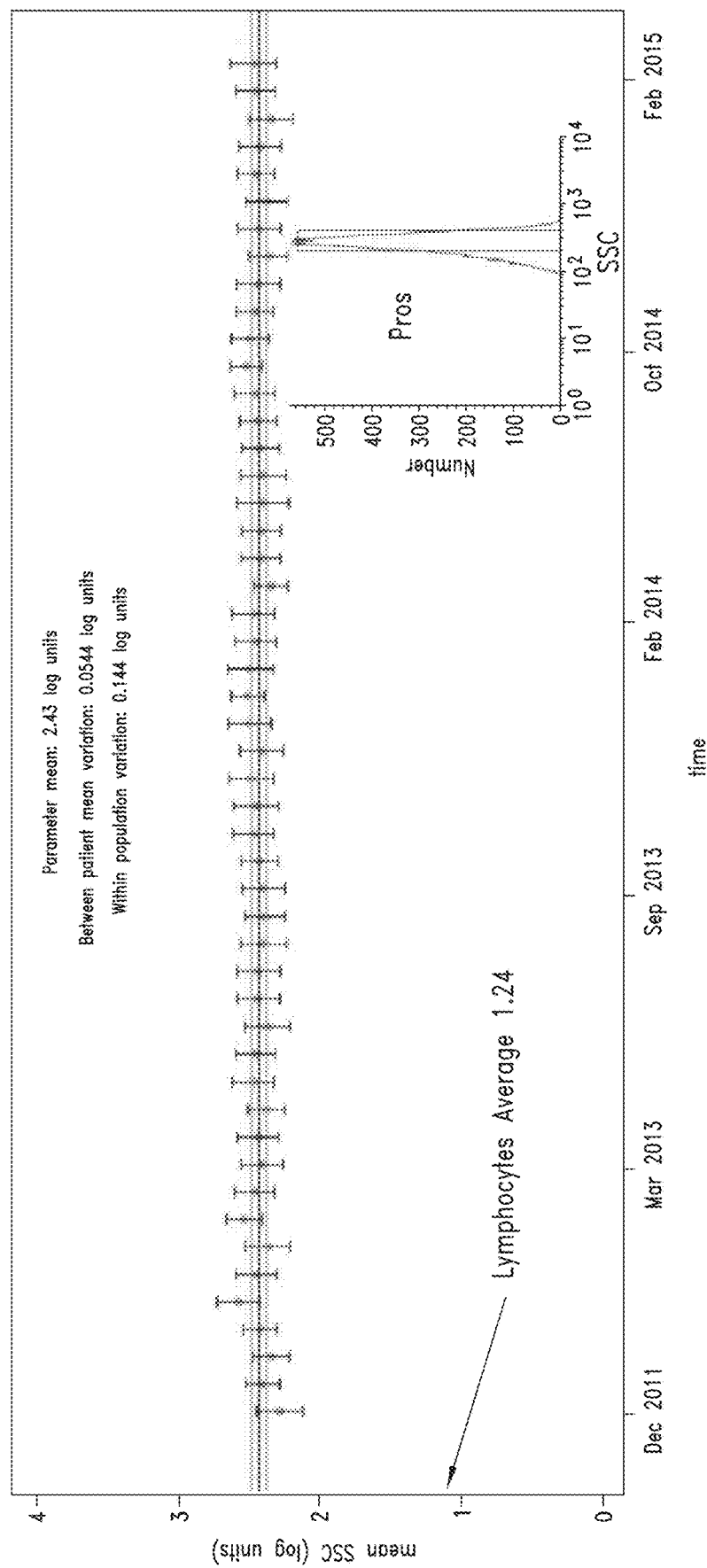

A second population studied were promyelocytes, which are the most mature myeloid cells in which AML is seen. The population was identified as negative for HLA-DR, negative for CD11b and high SSC. The predicted population for promyelocytes of a test patient is represented in FIG. 69 in blue, the results of the comparison are shown in FIGS. 70 and 71. The results are stable for the instrument. A statistical analysis of SSC may be used to determine if the promyelocytes have a change in granularity. For example, a change in granularity of the promyelocytes as measured by SSC is observed in stressed bone marrow and also in patients with myelodysplastic syndromes (MDS). Hypogranularity may be identified in MDS.

Figure 72:
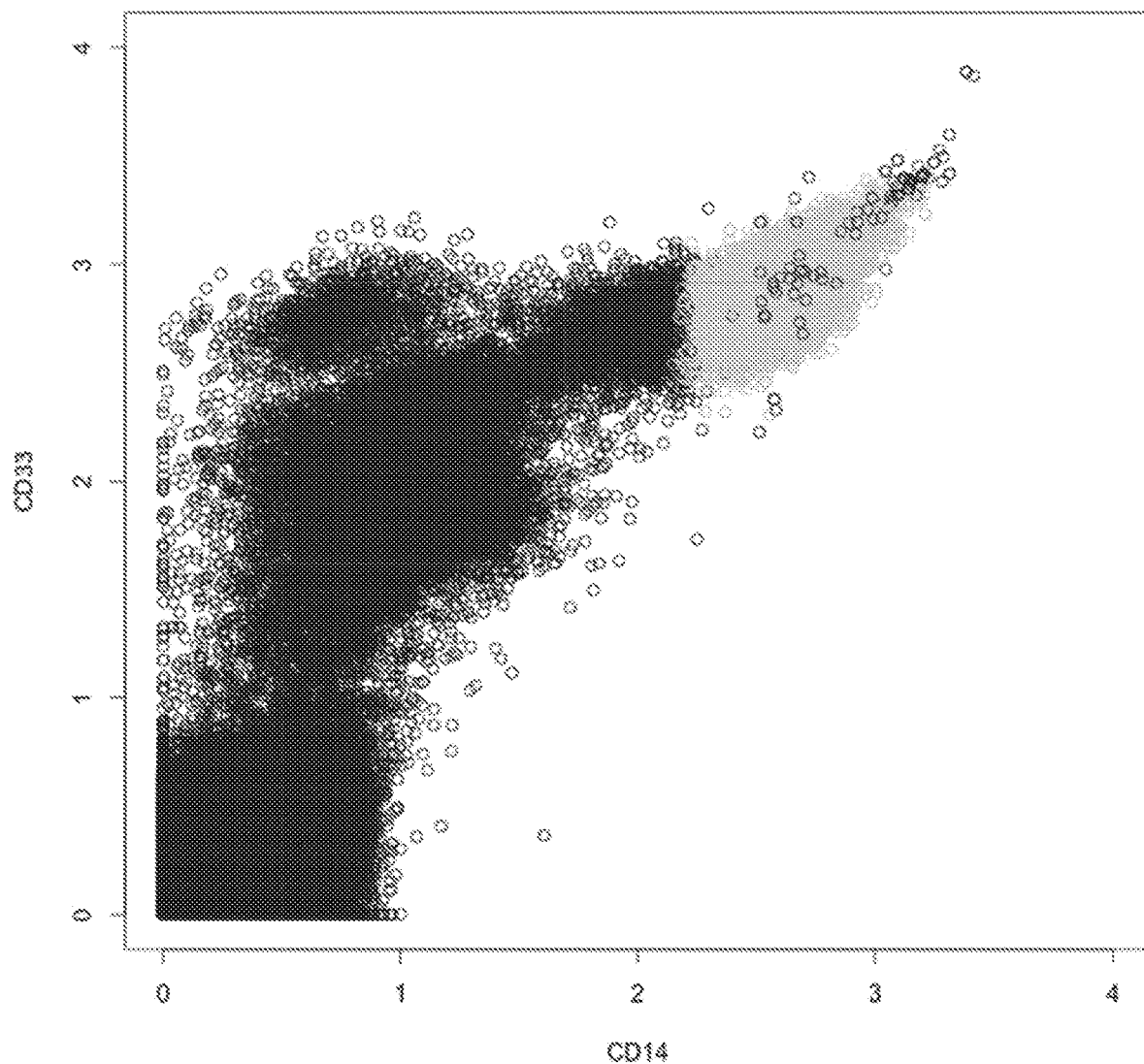
FIG. 72 is a representation of a predicted population for monocytes.
Figure 73:
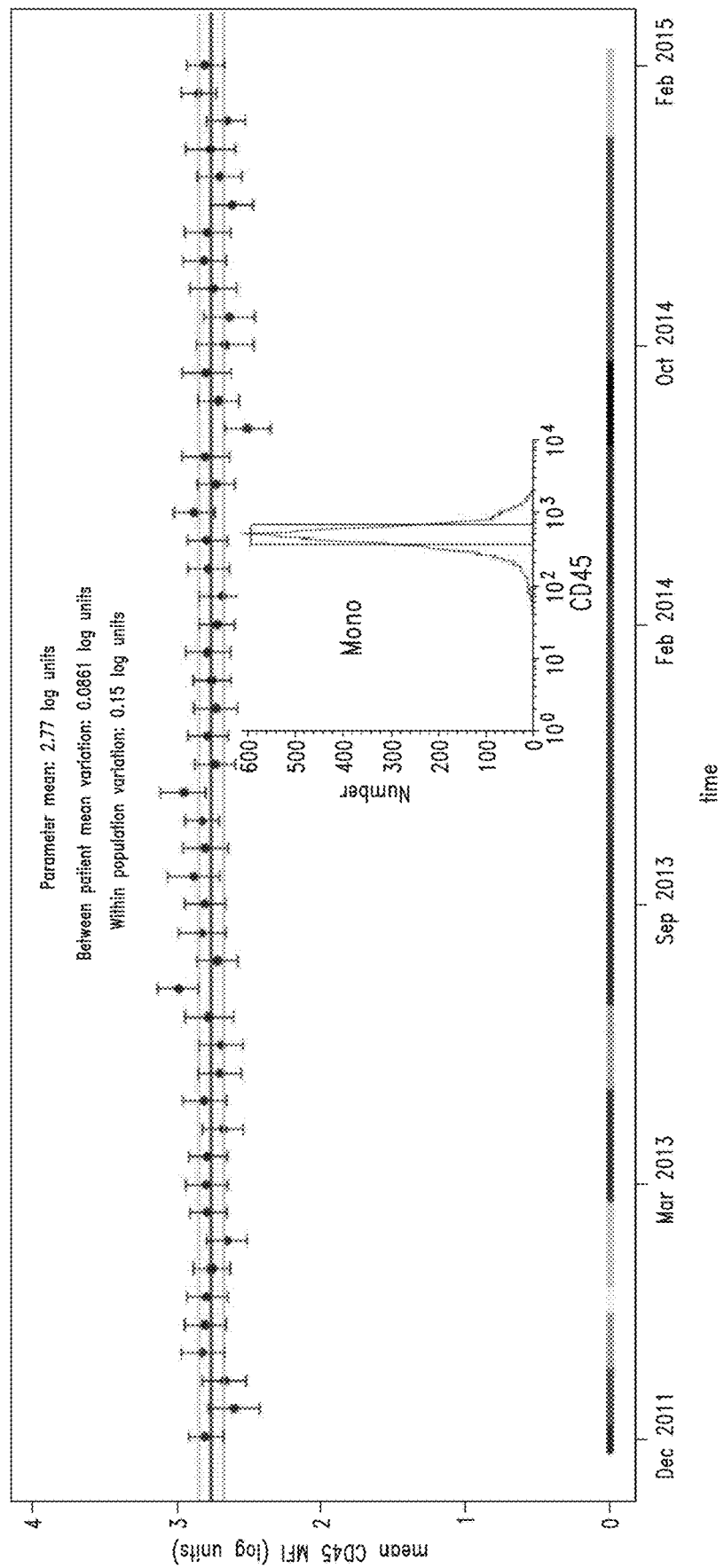
FIGS. 73 and 74 are illustration of results for a data set.
Figure 74:
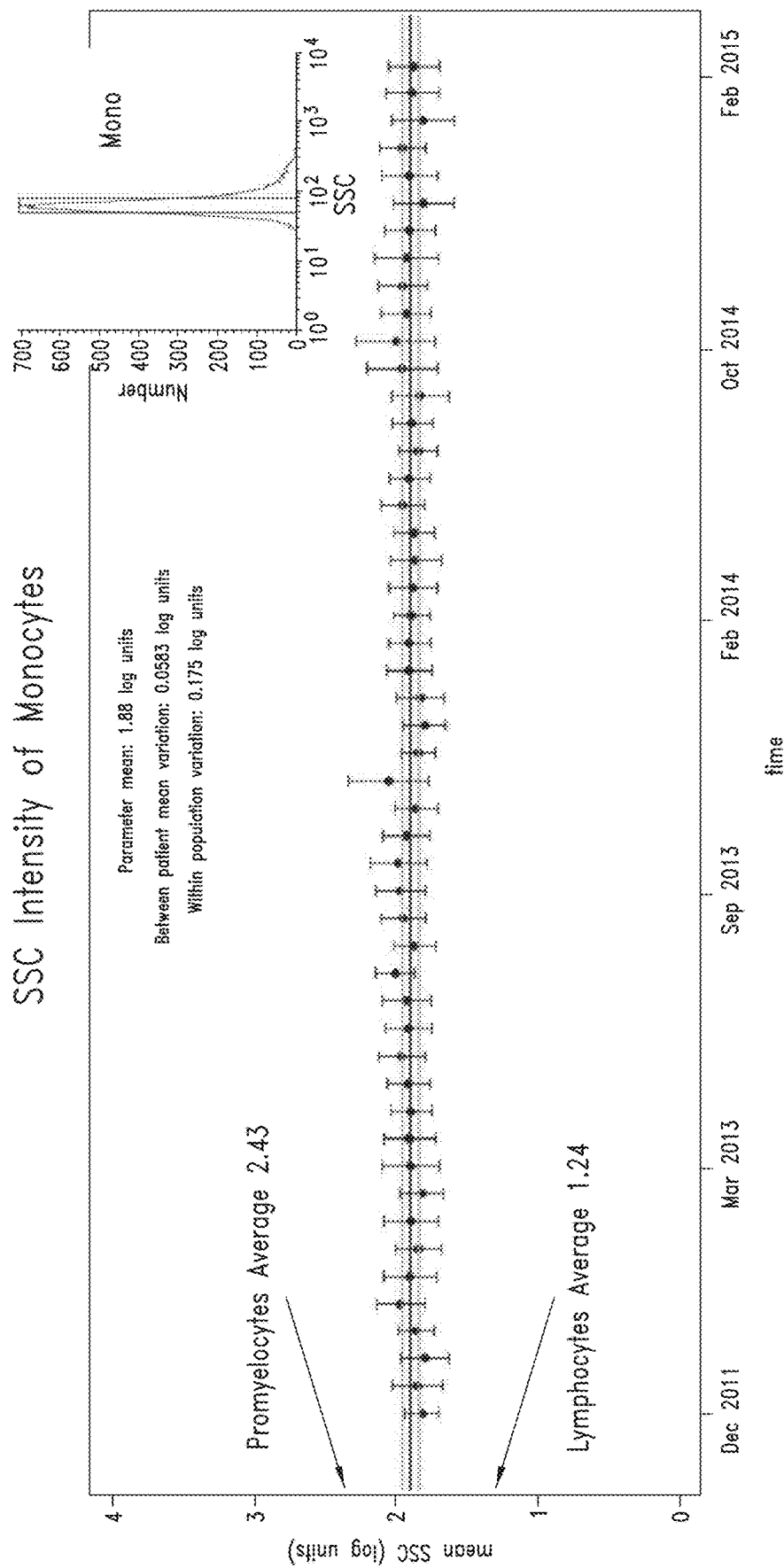

A third population studied were monocytes. The population was identified as positive for CD14, positive for CD33, with high levels of CD45 and intermediate SSC. The predicted population for monocytes is represented in FIG. 72 in green, followed by results of the comparison in FIGS. 73 and 74. The black dots identified as non-monocytes (overlapping the green dots) in the high CD14 region are non-viable cells/doublets.

Figure 75:
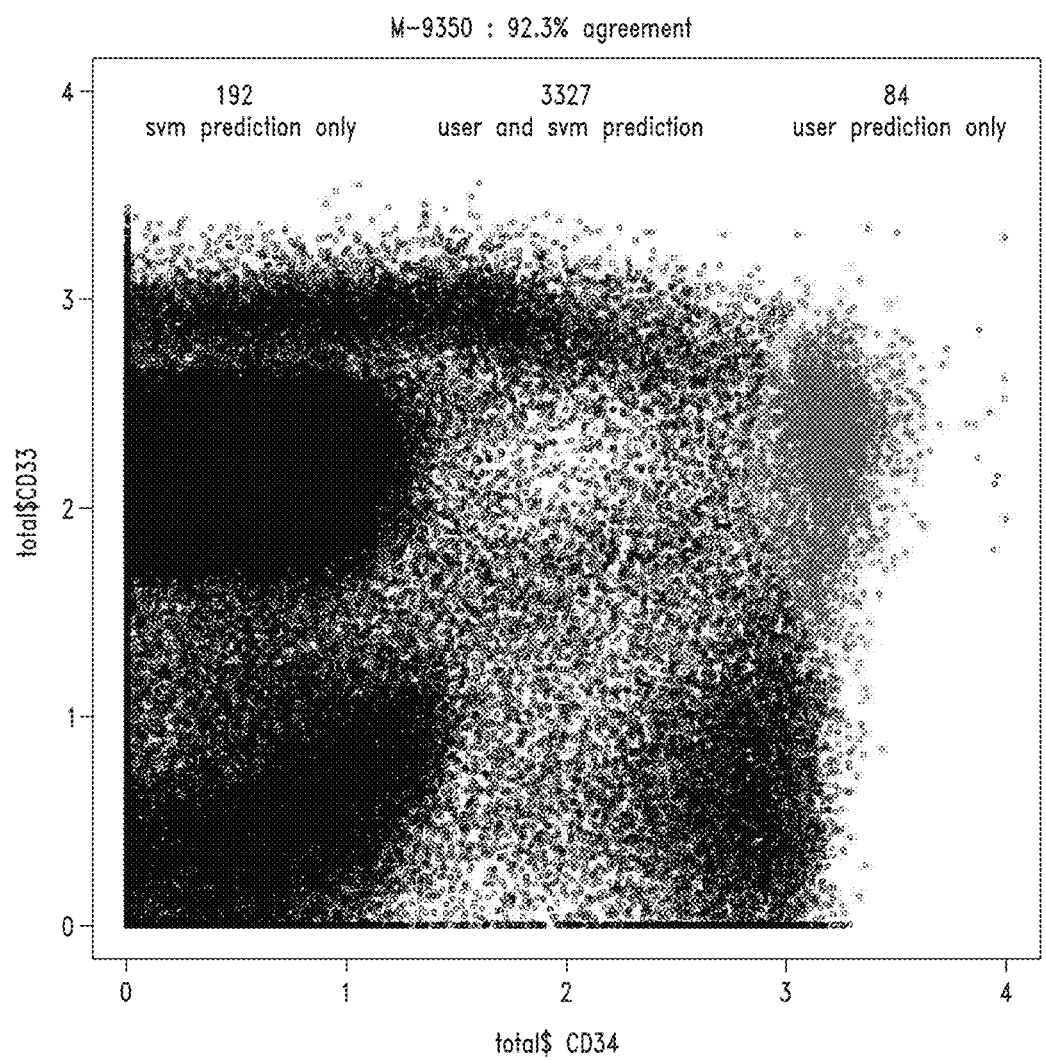
FIG. 75 is a representation of a predicted population for uncommitted progenitor cells.
Figure 76:
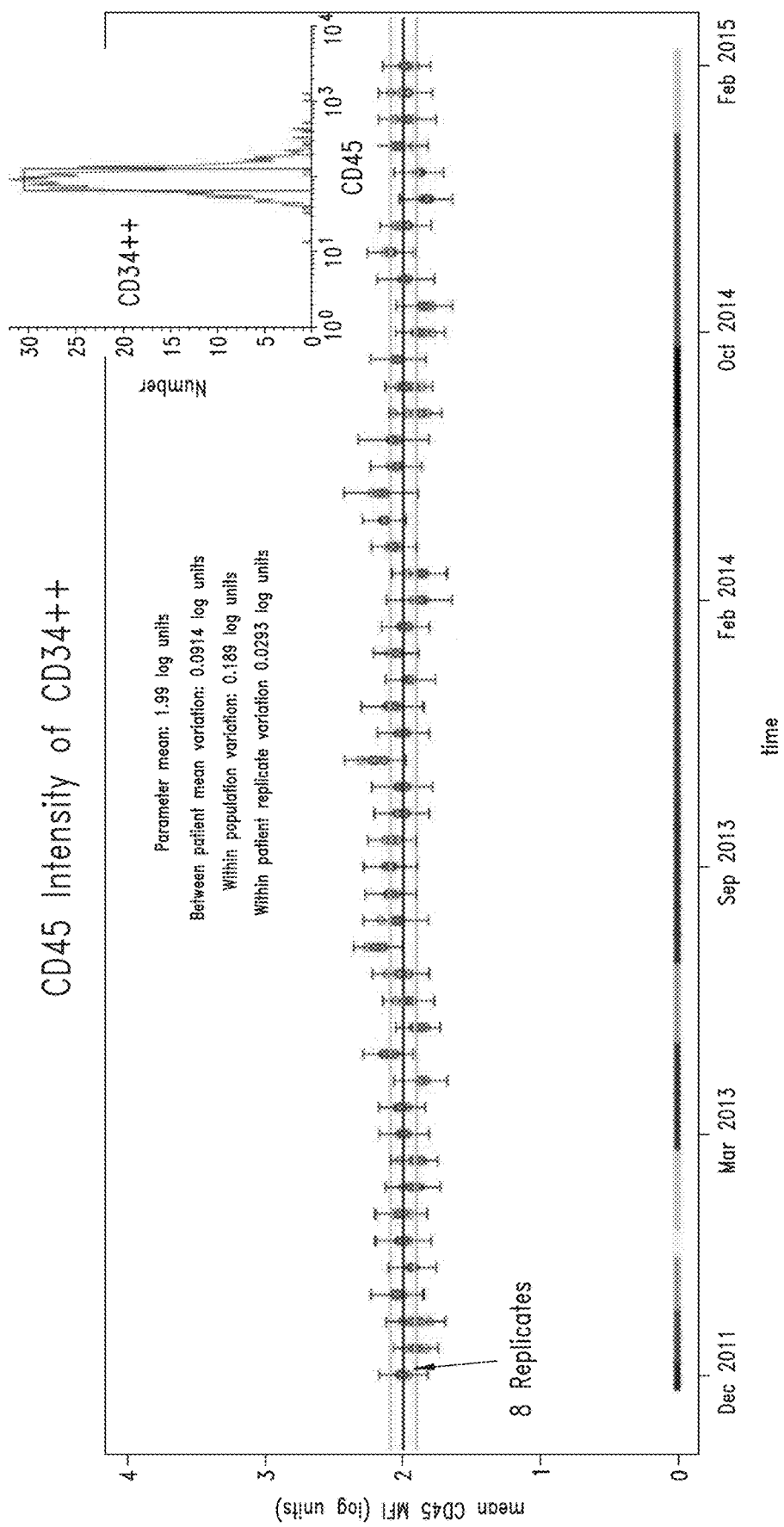
FIGS. 76 and 77 are illustration of results for a data set.
Figure 77:
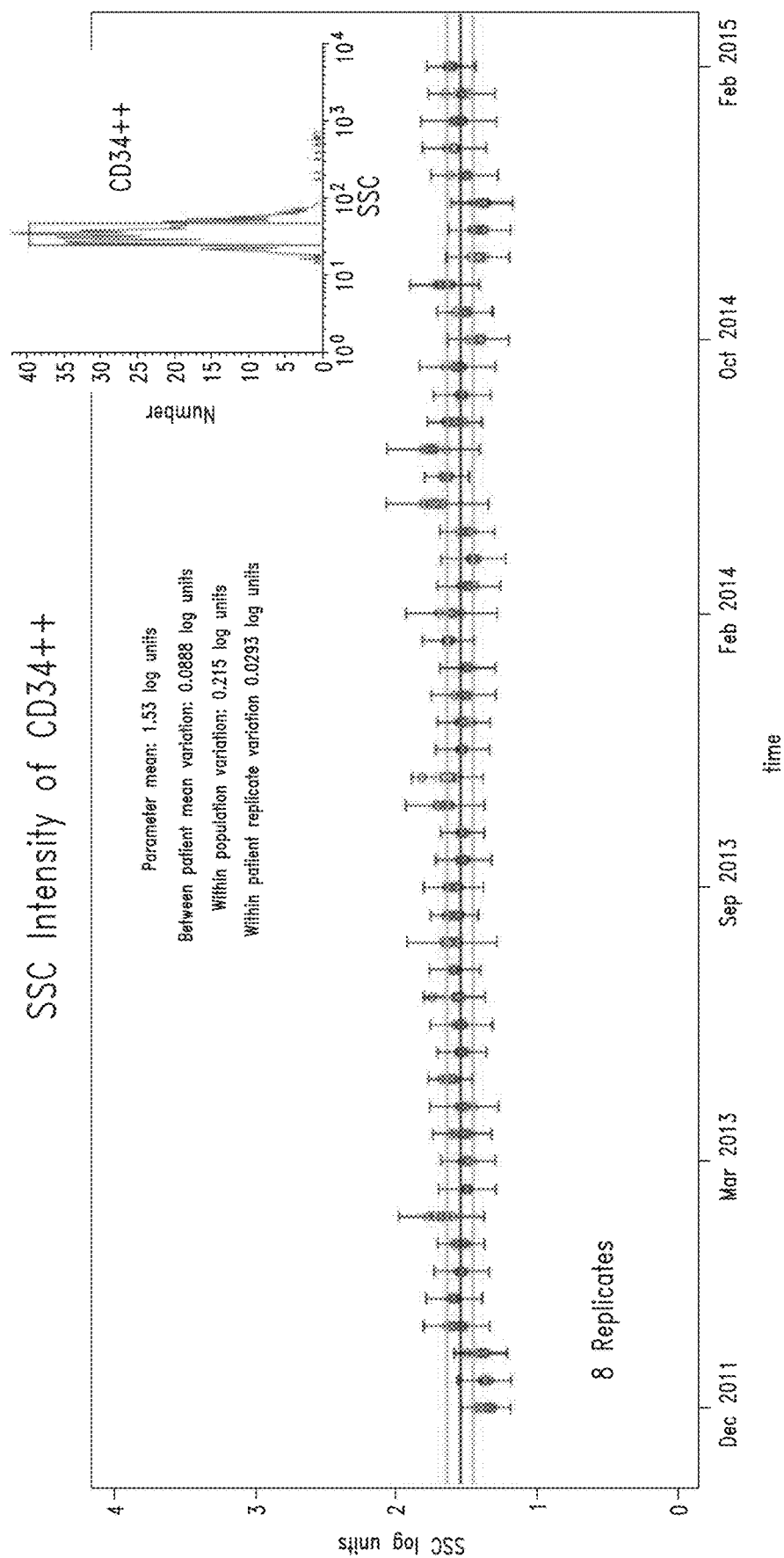

A fourth population studied were uncommitted progenitor cells, identified as bright CD34. CD33 in combination with CD34 was selected to identify this population of cells. The predicted population for uncommitted progenitor cells is represented in FIG. 75: Red indicates agreement between the SVM and an expert evaluation of a predicted population of uncommitted progenitor cells; purple indicates cells predicted by application of the SVM to be uncommitted progenitor cells, which the expert did not predict as uncommitted progenitor cells; and blue indicates cells which the expert predicted as uncommitted progenitor cells, but which application of the SVM did not predict as uncommitted progenitor cells. Results using the SVM prediction (red plus purple in the figure above) to determine the mean and standard deviation of the test patient data sets are produced in FIGS. 76 and 77.

Figure 78:
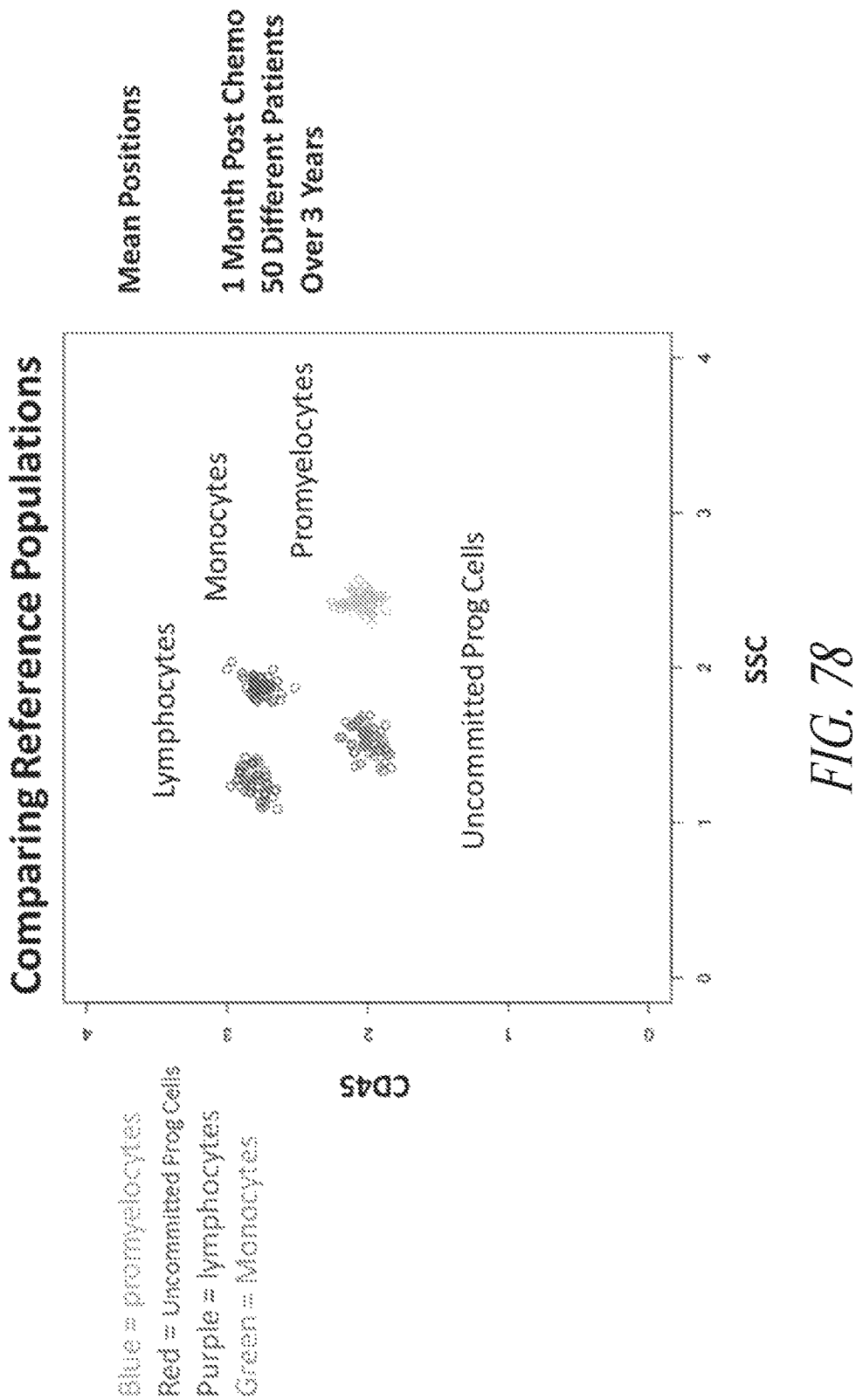
FIG. 78 is a representation of comparisons of reference populations with respect to CD45 and SSC.

The results of the reference populations with respect to CD45 and SSC are compared in FIG. 78.

Figure 79:
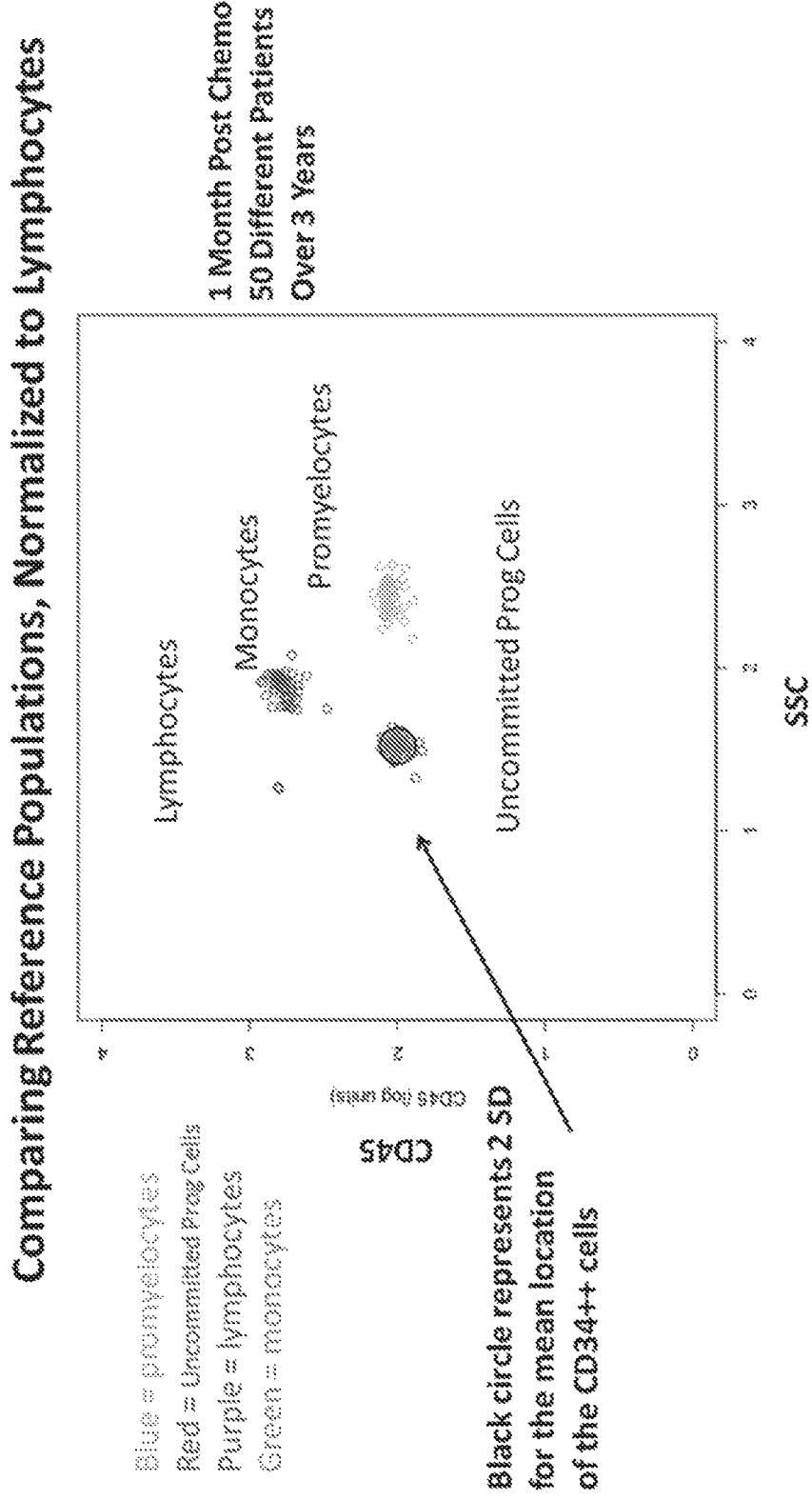
FIG. 79 is a representation of a lymphocyte population shifted to a fixed point.

A representation with the lymphocyte population shifted to a fixed point is reproduced in FIG. 79 (e.g., using the vector normalization process discussed above with reference to subroutine 3200 of FIG. 29). The CD34 bright population, the monocyte and the promyelocyte population are shifted by the same amount used to shift the lymphocyte population. When the position of the lymphocyte population is shifted to the fixed point, the positions of the data points for the other reference populations tightens, and the CD34 bright population, the promyelocyte population and the lymphocyte population appear to go up and down together. This suggests the variability is in the individual, rather than a reflection of the variability between parameters identifying the reference populations.

Figure 80:
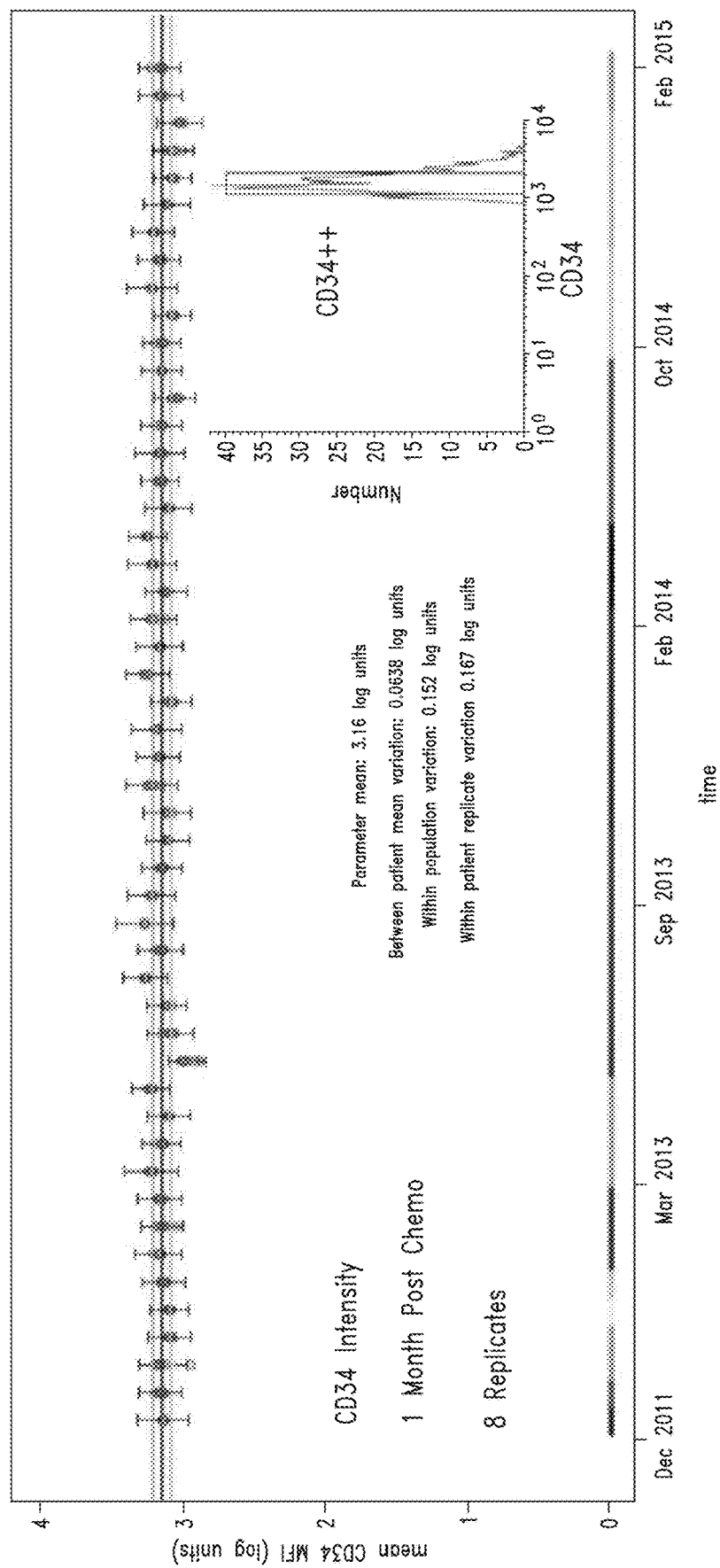
FIG. 80 is a representation of CD 34 intensity of CD34++.
Figure 81:
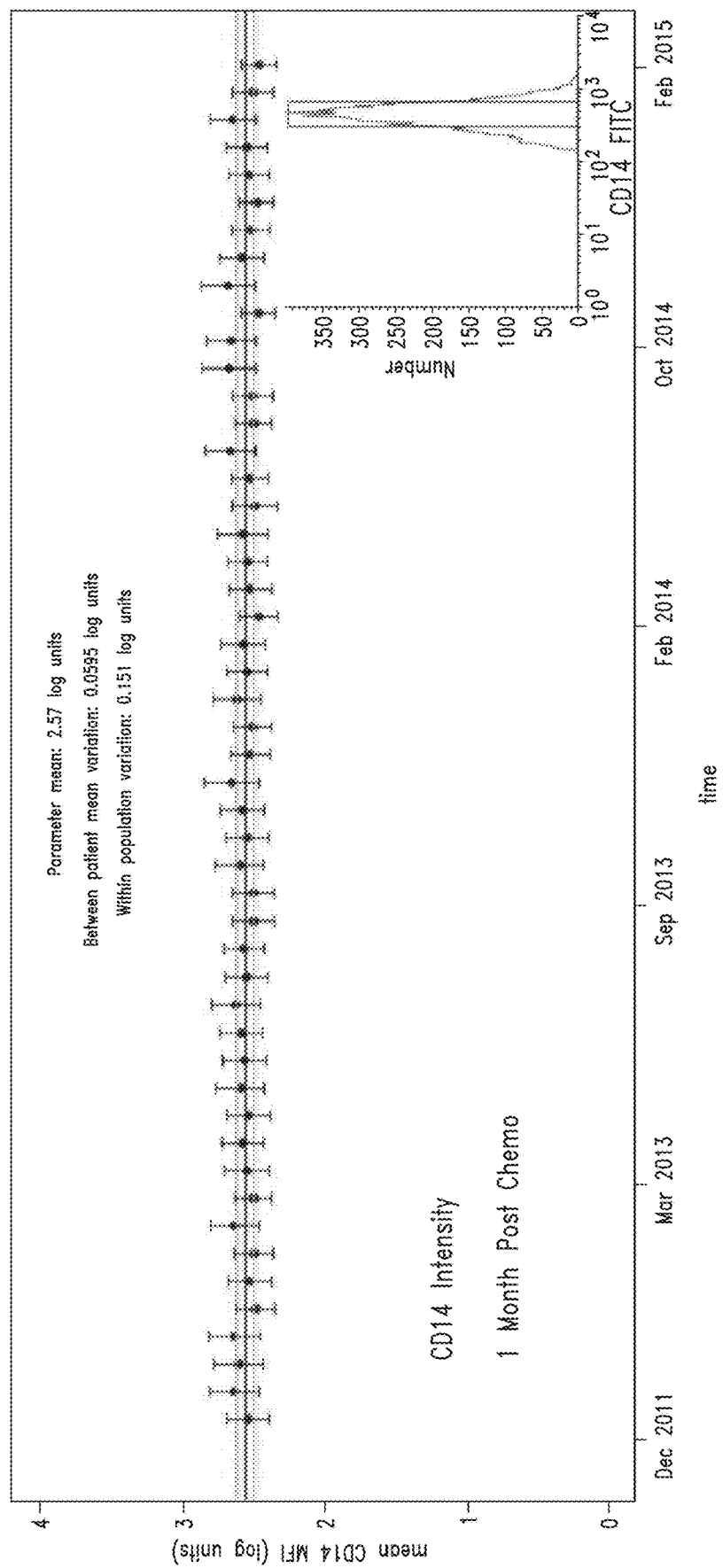
FIG. 81 is a representation of CD14 intensity of monocytes.

Further studies of other cell surface antigens on these reference populations showed that surface gene product (CD) intensity on uncommitted progenitor cells, and mature monocytes were also substantially constant from individual to individual. FIG. 80 is a representation of CD 34 intensity of CD34++. FIG. 81 is a representation of CD14 intensity of monocytes.

Figure 82:
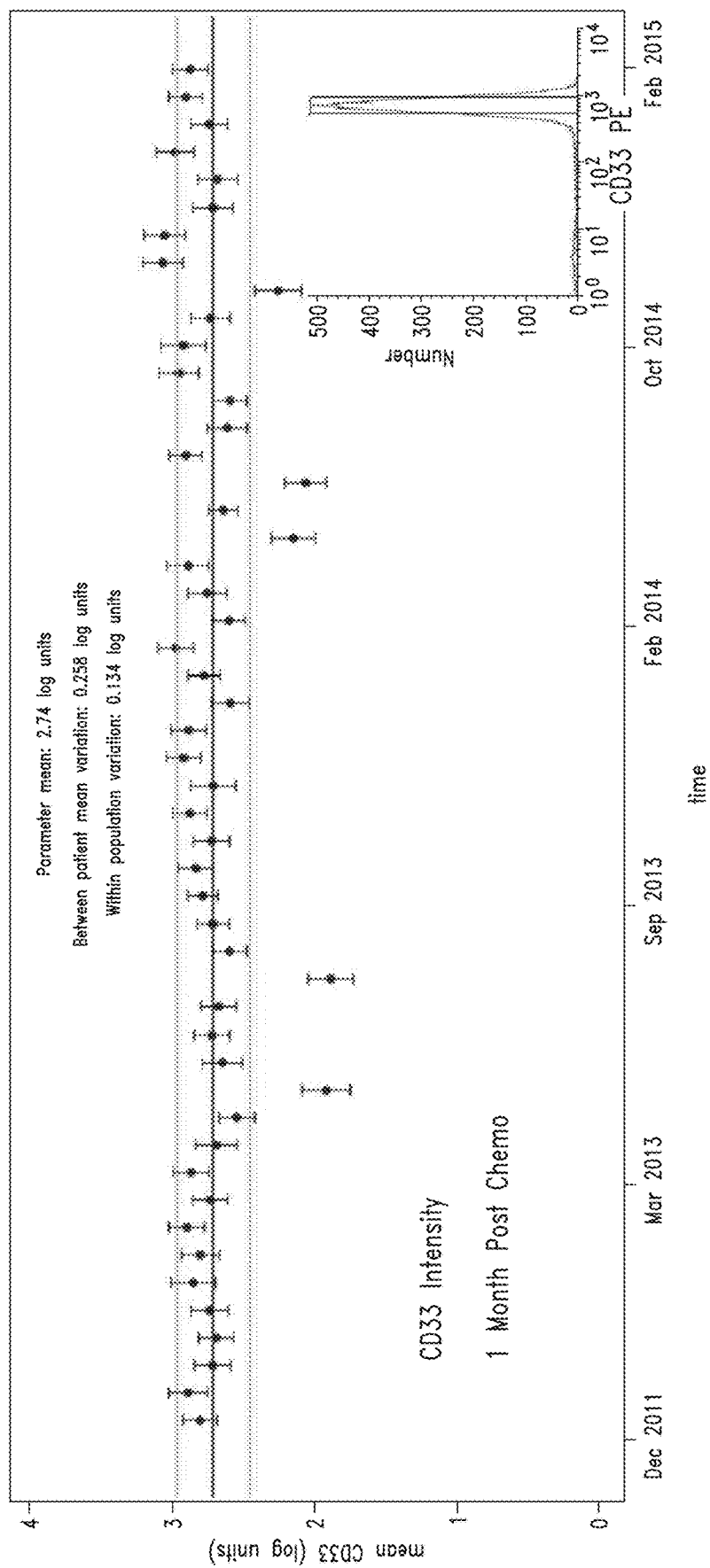
FIG. 82 is a representation of CD33 intensity of CD14++ monocytes.

Interestingly, it was found that CD33 intensity on mature monocytes was not constant from individual to individual. The ratio, however, between intensities of CD33 between monocytes and uncommitted progenitor cells was substantially constant. FIG. 82 is a representation of CD33 intensity of CD14++ monocytes.

Figure 83:
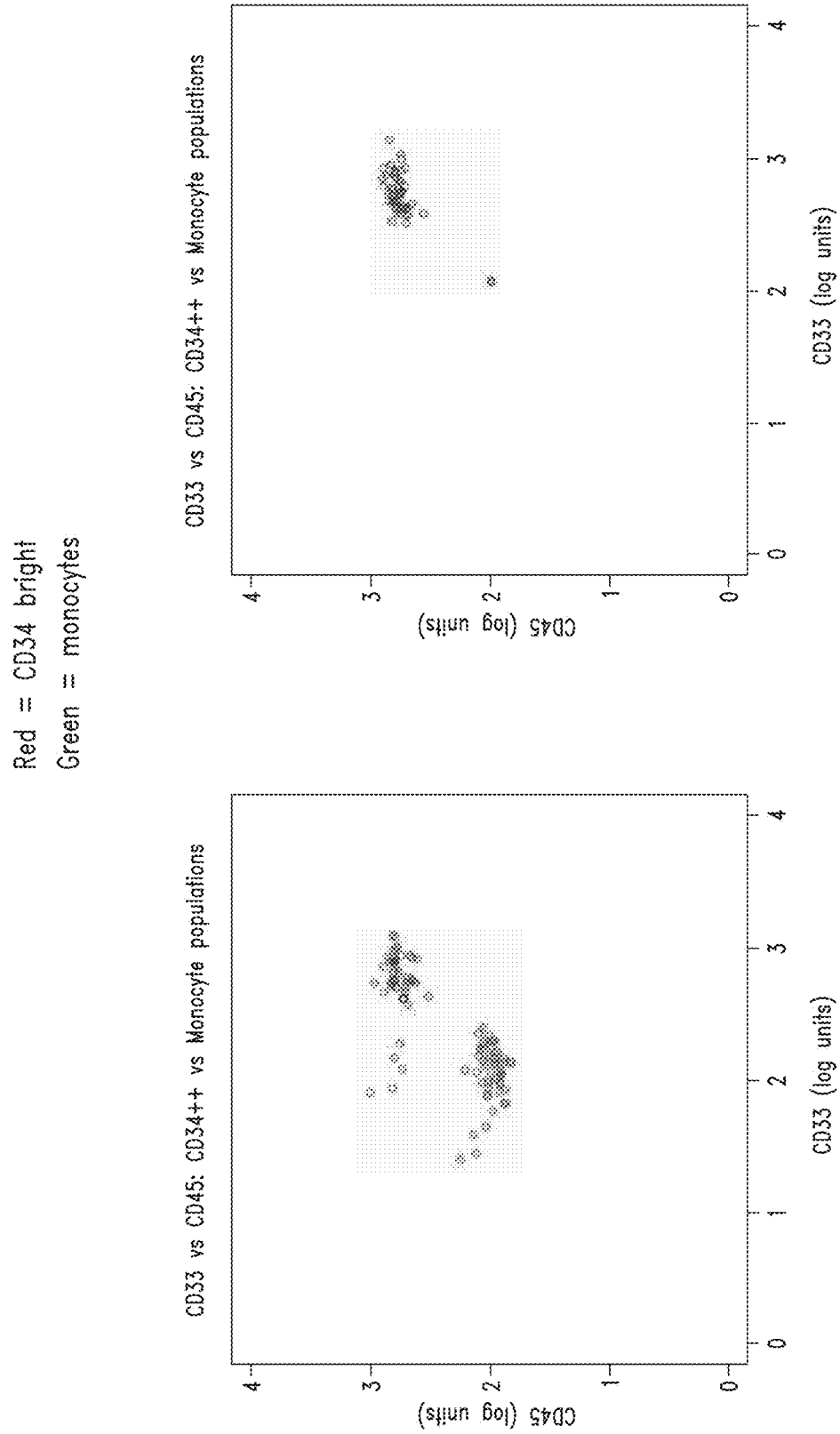
FIG. 83 is a representation of comparisons of cell populations.

In the representation in FIG. 83 on the left side, the monocytes (green) and the uncommitted progenitor cells (red) demonstrated a heterogeneous amount of CD33 (as well as lesser variability of CD45). This variability could be reduced by normalization of the data in a manner similar to that used for CD45/SSC performed previously using the mature lymphocytes as the reference population. In the right portion of FIG. 83, the position of the uncommitted progenitor cells was shifted to a single location with a concomitant shift in the position of the monocytes. This normalization resulted in tighter distribution of the monocyte population indicating that the ratio of amounts of CD33 between these cell populations was retained even if the absolute amounts varied from individual to individual. In this way, the individual variance could be reduced.

Some embodiments may take the form of or comprise computer program products. For example, according to one embodiment there is provided a computer readable medium comprising a computer program adapted to perform one or more of the methods or functions described above. The medium may be a physical storage medium such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some or all of the methods and/or functionality may be implemented or provided in other manners, such as at least partially in firmware and/or hardware, including, but not limited to, one or more application-specific integrated circuits (ASICs), digital signal processors, discrete circuitry, logic gates, standard integrated circuits, controllers (e.g., by executing appropriate instructions, and including microcontrollers and/or embedded controllers), field-programmable gate arrays (FPGAs), complex programmable logic devices (CPLDs), state machines, etc., as well as devices that employ RFID technology, and various combinations thereof.

As would be recognized by the skilled artisan, the above methods can be used in a number of settings, including but not limited to diagnostics and disease and treatment monitoring.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments have been described herein for purposes of illustration, various modifications may be made without deviating from the spirit and scope of the disclosure. The above examples are offered by way of illustration and not by way of limitation.

What is claimed is:

1. A method of characterizing a test set of biological cells in an n-dimensional space, comprising:
   exposing each cell in a normal set of biological cells to a plurality of four or more reagents;
   measuring a corresponding plurality of fluorescence intensities of each cell in the normal set of biological cells;
   mapping each cell in a normal set of biological cells to a corresponding point in an n-dimensional space based at least in part on the measured plurality of fluorescence intensities of the cell in the normal set of biological cells, wherein the corresponding points form a normal set of points in the n-dimensional space;
   defining a centroid line and radii for a set of reference clusters in the n-dimensional space based on the normal set of points in the n-dimensional space, wherein a cluster corresponds to a maturation level within a cell lineage;
   mapping each cell in a test set of biological cells to a corresponding point in the n-dimensional space, the corresponding points forming a test set of points;
   comparing the test set of points to the set of reference clusters, wherein the defining of the centroid line and radii for the set of reference clusters and the comparing the test set of points to the set of reference clusters, includes defining one or more multidimensional boundaries in the n-dimensional space using support vector machines; and
   diagnosing cancer based on the comparing of the test set of points to the set of reference clusters, wherein the method comprises:
   determining a standard reference mean for each reference population of a plurality of reference populations including a lymphocyte reference population and a monocyte reference population, the determining the standard reference mean for a reference population including:
      training at least one of the support vector machines to generate a multidimensional boundary in the n-dimensional space identifying a reference population of interest;
      for each normal patient in a set of normal patients, applying the generated multidimensional boundary to identify the reference population of interest for the normal patient, and determining a mean intensity of one or more parameters of the reference population by adding intensities of the population of interest for a given parameter and dividing by a total number of cells of the population of interest; and
      computing a standard reference mean for the reference population by determining a mean of all the mean reference intensities for each parameter of the reference population, wherein the standard reference mean is a vector; and
   normalizing the test set of points, the normalizing the test set of points including:
      identifying a lymphocyte reference population of the test set of points by applying to the test set of points the generated multidimensional boundary identifying the lymphocyte reference population of interest used to determine the standard reference mean;
      determining a mean intensity of one or more parameters of the lymphocyte reference population for the test set of points by adding intensities of the points for a given parameter in the lymphocyte reference population and dividing by a total number of cells of the lymphocyte reference population for the test set of points;

generating a normalization vector for the lymphocyte reference population of the test set of points by determining a difference between the mean parameter intensities for the lymphocyte reference population of the test set of points and the standard reference mean vector; and normalizing intensities of the points of each reference population of the test set of points based on the normalization vector generated for the lymphocyte reference population of the test set of points.

2. The method of claim 1 wherein the exposing each cell in the normal set of biological cells to a plurality of four or more reagents comprises staining a cell with a marker for CD10, a marker for CD19, a marker for CD20 and a marker for CD45.

3. The method of claim 1 wherein the exposing each cell in the normal set of biological cells to a plurality of four or more reagents comprises staining a cell with a marker for FSC, a marker for SSC, a marker for CD20 (FITC), a marker for CD10 (PE), a marker for CD45 and a marker for CD19.

4. The method of claim 1 wherein the exposing each cell in the normal set of biological cells to a plurality of four or more reagents comprises staining a cell with a marker for FSC, a marker for SSC, a marker for CD22 (FITC), a marker for CD34 (PE), a marker for CD45 and a marker for CD 19.

5. The method of claim 1 wherein the normal set of biological cells is a subset of a sample of normal biological cells.

6. The method of claim 1 wherein the normal set of biological cells comprises a plurality of subsets and each subset comprises a set of cells selected from a sample drawn from an individual.

7. The method of claim 1 comprising representing the defined set of reference clusters in the n-dimensional space in a Cartesian coordinate display.

8. The method of claim 7 wherein color is used to represent additional dimensions.

9. The method of claim 1 wherein the centroid line comprises a plurality of branches.

10. The method of claim 1 wherein the set of reference clusters comprises a set of hyperellipsoids in the n-dimensional space defined by the centroid line and radii.

11. The method of claim 1, comprising:
determining a normalization vector for a normal patient data set; and
adjusting the normal patient data set based on the determined normalization vector before training a support vector machine of the support vector machines.

12. The method of claim 11 wherein the reference population of interest is a monocyte population.

13. The method of claim 1, comprising:
assessing the multidimensional boundary; and
selectively adjusting the multidimensional boundary based on the assessment.

14. The method of claim 1, comprising:
classifying cells in a test set of cells based on a multidimensional boundary in the n-dimensional space generated using a support vector machine of the support vector machines.

15. The method of claim 14 wherein the multidimensional boundary in the n-dimensional space used to classify cells in the test set of cells is used to define the centroid line.

16. The method of claim 14 wherein the multidimensional boundary in the n-dimensional space is used to define the radii.

17. The method of claim 14, comprising:
filtering classified cells of a test set of cells.

18. The method of claim 1, comprising:
determining a mean reference intensity of a population of interest of a patient identified using a support vector machine of the support vector machines.

19. The method of claim 18 wherein the patient is one of a normal patient and a test patient.

20. The method of claim 1, comprising:
determining a radius based on the determined standard reference mean.

21. The method of claim 1, comprising:
determining a normalization vector for a reference population of a test patient data set; and
adjusting the test patient data set based on the determined normalization vector before comparing the test patient data set to the set of reference clusters.

22. The method of claim 1, comprising:
determining a normalization vector for a test patient data set; and
adjusting the test patient data set based on the determined normalization vector before comparing the test patient data set to the set of reference clusters.

23. The method of claim 1, comprising:
determining, for each data point of each normal patient data set corresponding to a reference population, a tangential intersection point between the respective data point and the centroid line on the centroid line;
determining, for each data point of each normal patient data set corresponding to a reference population, a unidimensional distance between the data point and the respective tangential intersection point on the centroid line;
determining, for a combined normal patient reference population data set, standard deviations of respective parameter values for each cluster;
performing z-score transformations on the unidimensional distances determined for each normal patient data set based on the determined standard deviations of each cluster, generating scaled positions for each data point;
determining multidimensional Euclidian distances between the scaled position of each data point and the respective tangential intersection point; and
determining a mean and standard deviation of the multidimensional Euclidean distance for each cluster.

24. The method of claim 1, comprising:
generating a vector having a component corresponding to one or more parameters of a cell or data point.

25. The method of claim 1, comprising:
generating a vector having a component corresponding to parameters of a reference population.

26. The method of claim 1, comprising:
determining, for each data point of each normal patient data set corresponding to a reference population, a tangential intersection point between the respective data point and the centroid line on the centroid line;
determining, for each data point of each normal patient data set corresponding to a reference population, a unidimensional distance between the data point and the respective tangential intersection point on the centroid line;

performing z-score transformations on the unidimensional distances determined for each normal patient data set based on a normal radii for each cluster;

determining multidimensional Euclidian distances between the scaled position of each data point and the respective tangential intersection point;

determining, for each cluster of each normal patient data set, respective mean Euclidean distances between data points of the cluster and the centroid line;

determining, for each normal patient data set, a respective frequency of cells in the clusters of the normal patient data set;

determining a mean and standard deviation of data points in each cluster of a combined normal patient data set based on the determined respective mean Euclidean distances; and determining a mean distribution of cells in each cluster of a combined normal patient data set based on the determined respective distributions of cells.

27. The method of claim 26, comprising determining the normal radii.

28. The method of claim 26, comprising retrieving the normal radii.

29. The method of claim 1, comprising:

determining, for each data point of a test patient data set corresponding to a reference population, a tangential intersection point between the respective data point and the centroid line on the centroid line;

determining, for each data point of the test patient data set corresponding to a reference population, a unidimensional distance between the data point and the respective tangential intersection point on the centroid line;

performing z-score transformations on the unidimensional distances determined for the test patient data set based on a normal radii for each cluster;

determining multidimensional Euclidian distances between the scaled position of each data point and the respective tangential intersection point;

determining, for each cluster of the test patient data set, respective mean Euclidean distances between data points of the cluster and the centroid line;

determining a respective distribution of cells in clusters of the test patient data set; and generating an image indicative of at least one of:
 a range of normal distances of each cluster to the centroid line;
 an expected distribution of cells to each cluster;
 distances of data points of a test patient data set from the centroid line; and
 a distribution of cell frequencies in clusters of the test patient data set to a distribution of cell frequencies in clusters of the normal patient data set.

30. The method of claim 29 wherein determining a distribution of cells in a cluster of the test patient data set comprises determining a percentage of cells in the test patient data set which are classified as being in the cluster.

31. The method of claim 29, comprising determining the normal radii.

32. The method of claim 1, comprising:

determining, for each data point of a test patient data set corresponding to a reference population, a tangential intersection point between the respective data point and the centroid line on the centroid line;

determining, for each data point of the test patient data set corresponding to a reference population, a unidimensional distance between the data point and the respective tangential intersection point on the centroid line;

performing z-score transformations on the unidimensional distances determined for the test patient data set based on a normal radii for each cluster;

determining multidimensional Euclidian distances between the scaled position of each data point and the respective tangential intersection point;

determining a filtering component of a radius;

identifying data points to include in a digital image representative of the test patient data set based on the determined filtering component; and generating an image representative of the test patient data set based on the identified data points.

33. The method of claim 32, comprising:

scaling the determined filtering component by a subtraction vector; and identifying data points to include in the digital image based on the scaled filtering component.

34. The method of claim 33, comprising:

excluding from the identified data points data points in the test patient data set having a value less than the scaled filtering component.

* * * * *